US009549245B2

(12) United States Patent
Frater

(10) Patent No.: US 9,549,245 B2
(45) **Date of Patent: *Jan. 17, 2017**

(54) SPEAKERPHONE AND/OR MICROPHONE ARRAYS AND METHODS AND SYSTEMS OF USING THE SAME

(71) Applicant: Robert Henry Frater, Lindfield (AU)

(72) Inventor: Robert Henry Frater, Lindfield (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/793,474

(22) Filed: Jul. 7, 2015

(65) Prior Publication Data

US 2016/0007114 A1 Jan. 7, 2016

Related U.S. Application Data

(63) Continuation of application No. 12/926,376, filed on Nov. 12, 2010, now Pat. No. 9,113,264.
(Continued)

(51) Int. Cl.
*A61F 11/06* (2006.01)
*H04R 1/40* (2006.01)
(Continued)

(52) U.S. Cl.
CPC ........... *H04R 1/406* (2013.01); *G10L 21/0232* (2013.01); *H04R 1/02* (2013.01); *H04R 3/005* (2013.01);
(Continued)

(58) Field of Classification Search
CPC ......... H04R 3/005; H04R 1/406; H04R 1/342; H04R 2201/401; H04R 2227/001; H04R 1/02; H04R 27/00; H04R 2201/403; H04R 2410/01; H04R 2430/25; H04R 2499/11; G10L 21/0232; G10L 2021/02082; G10L 2021/02166
USPC ........... 381/94.1, 94.3, 66, 56, 332, 92, 122; 379/388.01, 420.03, 420
See application file for complete search history.

(56) References Cited

U.S. PATENT DOCUMENTS 5,121,426 A 6/1992 Baumhauer
5,524,059 A 6/1996 Zurcher
(Continued)

FOREIGN PATENT DOCUMENTS

CN 1839663 A 9/2006
EP 0652686 8/2002
(Continued)

OTHER PUBLICATIONS

International Search Report dated Jan. 27, 2011 for PCT/AU2010/001516 (co-pending related application).
(Continued)

*Primary Examiner* — Vivian Chin
*Assistant Examiner* — Ammar Hamid
(74) *Attorney, Agent, or Firm* — Jones Day

(57) ABSTRACT

The present disclosure is directed to devices, methods and systems for microphone arrays wherein enhancing performance of directional microphone arrays is provided. Enhanced performance of speaker phones is also provided. In certain embodiments, the housing of the device is configured to support the at least three microphones and the loudspeaker in a substantially first orientation; and the at least three microphones and the loudspeaker are arranged in a spatial relationship such that appropriate phase and delay characteristics achieve a substantial null response in the at least three microphones and in the loudspeaker in a substantial vertical direction away from the substantially first orientation over a desired audible range of frequencies and the device is able to provide a response to sounds over a range of first oriented elevations.

8 Claims, 49 Drawing Sheets

Related U.S. Application Data

(60) Provisional application No. 61/272,862, filed on Nov. 12, 2009.

(51) Int. Cl.

| | |
|---|---|
| ***H04R 27/00*** | (2006.01) |
| ***G10L 21/0232*** | (2013.01) |
| ***H04R 1/02*** | (2006.01) |
| ***H04R 3/00*** | (2006.01) |
| *G10K 11/16* | (2006.01) |
| *G10L 21/0208* | (2013.01) |
| *G10L 21/0216* | (2013.01) |

(52) U.S. Cl.

CPC ..... *H04R 27/00* (2013.01); *G10L 2021/02082* (2013.01); *G10L 2021/02166* (2013.01); *H04R 2201/401* (2013.01); *H04R 2201/403* (2013.01); *H04R 2227/001* (2013.01); *H04R 2227/007* (2013.01); *H04R 2410/01* (2013.01); *H04R 2430/25* (2013.01); *H04R 2499/11* (2013.01)

(56) References Cited

U.S. PATENT DOCUMENTS

| | | | | |
|---|---|---|---|---|
| 7,325,004 | B2 * | 1/2008 | Sastry | G06F 17/30286 |
| 7,702,111 | B2 | 4/2010 | Gunnarsson | |
| 7,925,004 | B2 * | 4/2011 | Hodges | H04R 27/00 379/388.01 |
| 7,970,151 | B2 * | 6/2011 | Oxford | H04M 1/6008 381/122 |
| 8,111,838 | B2 * | 2/2012 | Tokuda | H04M 1/6033 381/92 |
| 8,155,926 | B2 * | 4/2012 | Taenzer | H04R 3/005 702/116 |
| 2005/0232441 | A1 | 10/2005 | Beaucoup | |
| 2005/0271221 | A1 * | 12/2005 | Cerwin | H04R 1/406 381/92 |
| 2009/0106021 | A1 * | 4/2009 | Zurek | G10L 21/0208 704/226 |
| 2010/0202628 | A1 * | 8/2010 | Meyer | H04R 1/406 381/92 |

FOREIGN PATENT DOCUMENTS

| | | |
|---|---|---|
| EP | 2154907 | 2/2010 |
| GB | 2066620 | 7/1981 |
| WO | WO 97/40645 | 10/1997 |
| WO | WO 2008/040991 | 4/2008 |

OTHER PUBLICATIONS

Communication pursuant to Article 94(3) EPC for European Application No. 10829363.0 dated Jan. 28, 2015.

* cited by examiner

Placement of microphones "2 Stage 5+1"

Placement of microphones "Circular 5"

Phase relationship between microphones 197
64
66, 65
66
65
12
13
50
15
A
B
202-2345671
1 2 3
4 5 6
7 8 9
* 0 #

Digital transmission echo canceller using digital subtraction

SPEAKERPHONE AND/OR MICROPHONE ARRAYS AND METHODS AND SYSTEMS OF USING THE SAME

CROSS REFERENCE TO RELATED APPLICATION

This application is a continuation of U.S. application Ser. No. 12/926,376, filed Nov. 12, 2010, which claims the benefit of priority from U.S. Provisional Application No. 61/272,862, filed Nov. 12, 2009. The foregoing related U.S. applications and the following documents are incorporated herein, in their entirety, by reference: International Telecommunications Union (ITU) Recommendations ITU-T G.168, ITU-T G.165, ITU-T G.164, ITU-T G.131, and ITU-T G.114.

TECHNICAL FIELD

The present disclosure relates to devices, methods and systems for microphone arrays. The present disclosure also relates to devices, methods and systems for enhancing the performance of directional microphone arrays. The present disclosure also relates to methods and systems for enhancing the performance of speakerphones.

BACKGROUND

The use of speech systems is commonplace. For example, in teleconferencing systems, participates typically gather in an office or meeting room and are seated at various locations about the room. The room used is typically not equipped with special sound tailoring materials, and echoes of both near and far-end voices add to the noise level. If the room is large enough, some participates may be seated away from the conference table, distancing themselves from the microphones. Some participates may not actively speak, or may contribute only occasionally. Their presence, however, adds to the number of sources of room noise as pencil tapping, paper rustling, and side conversations develop. These noise sources further degrade the sound quality experienced by the far-end parties.

The majority of speech systems have microphones deployed at one, two, or at most three locations. The microphones are typically positioned on the surface of a conference table, distributed in a manner that provides the best pickup of the most significant contributors to the meeting. This selection of microphone positions may make some of the contributors difficult to hear. Occasional participants are frequently forced to move closer to a microphone when they speak, creating additional room noise as they switch seats or move chairs.

Microphone arrays are generally designed as free-field devices and in some instances are embedded within a structure. A problem with prior art microphone arrays is that the beam width decreases with increasing frequency and sidelobes become more problematic. This results in significant off axis "coloration" of the signals. As it is impossible to predict when a talker will speak, there is necessarily a period time during which the talker will be off axis with consequential "coloration" degraded performance.

Microphones with "pancake directivity" for use in speech systems are known. For example, arrangements of directional microphones covering 360 degrees in the horizontal plane exist in the telecom and conference speaker phone art. In order to make conference speakerphones effective people have used various arrays of microphones. Systems that provide directivity in microphone are expensive and complex and they do not provide a consistent beam shape over the frequency range of use. Directional microphones are known for use in speech systems to minimize the effects of ambient noise and reverberation. It is also known to use multiple microphones when there is more than one talker, where the microphones are either placed near to the source or more centrally as an array. Moreover, systems are also known for selecting which microphone or combination to use in high noise or reverberant environments. For example, in teleconferencing applications, it is known to use arrays of directional microphones associated with an automatic mixer. The limitation of these systems is that they are either characterized by a fairly modest directionality or they are of costly construction.

Another issue is the speakerphone type systems can manifest different types of echoes. For example, acoustic echo from feedback in the acoustic path between the speaker of the phone and its microphone. Another example is line echo that originates in the switched network that routes a call between stations. Acoustic feedback is a problem in speakerphones and known systems often incorporate some type of expensive electronic circuitry adapted to suppress, cancel, or filter out unwanted acoustic echo during use.

It would useful to have a microphone array that is less expensive, less complex and provides more consistent performance over the appropriate range of verbal frequencies in certain environments such as, but not limited to, teleconferencing. Accordingly, there is a long-felt but as yet unsatisfied need in the field for a speakerphone design that inherently reduces the amount of acoustic echo present in the phone, thereby resulting in the need for less complex, and hence, less costly echo cancellation circuitry, and one that also provides better low-frequency sound definition and high-frequency sound dispersion by the loudspeaker of the phone. There is also a need for devices, methods and systems for microphone arrays that allow for greater flexibility in the placement in the microphone. There is also a need for devices, methods, and systems for speakerphones that have improved echo cancellation, better sound performance and dispersion, and require a substantially smaller footprint than speakerphones of the prior art.

Further limitations and disadvantages of conventional and traditional approaches will become apparent to one of ordinary skill in the art through comparison of such systems with the present disclosure as set forth in the present application with reference to the drawings.

DETAILED DESCRIPTION

Certain embodiments provide a device comprising: a plurality of microphone elements arranged in a spatial relationship such that appropriate phase and delay characteristics achieve a substantial null response in the substantial vertical direction over the desired audible range of frequencies and with the facility to provide a response to sounds in the horizontal direction. In certain aspects the array will have at least three microphones. In certain aspects the device will include at least one loudspeaker arranged in relationship to the microphone array such that the audio from the speaker is also cancelled, or substantially cancelled, in part by the microphone array.

Certain embodiments provide a device comprising: a plurality of microphone elements arranged such that appropriate phase and delay characteristics achieve a substantial zone of insensitivity in a vertical direction over the audible range of frequencies and with the facility to provide a response to sounds in the horizontal direction. In certain aspects the array will have at least three microphones. In certain aspects the device will include at least one loudspeaker arranged so that the audio from the speaker is also cancelled by the microphone array.

Certain embodiments provide a device comprising: a directional microphone array, a housing and a loudspeaker arranged within the housing such that the speaker is disposed in a zone of insensitivity of the microphone array and radiates sound away from the microphone array and towards a surface upon or against which the housing is abutted, such as a desktop or a vertical wall surface. The speaker has a sound radiation axis that is disposed generally perpendicularly to the abutting surface.

Certain embodiments provide a device comprising: a least three microphone elements configured to provide appropriate phase and delay characteristics so as to achieve at least one axis of sensitivity defining a zone of microphone sensitivity, and at least one axis of insensitivity defining a zone of insensitivity of the microphone over the 300 Hz to 3.3 KHz frequency range.

Certain embodiments provide device for use in audio and/or visual telecommunications comprising: a plurality of microphone elements arranged in an array such that the microphone array is configured with appropriate phase and delay characteristics so as to achieve a substantial null response in the substantial vertical direction over the audible range of frequencies; and with the facility to provide a response to sounds in the horizontal direction and at least three microphone.

In certain embodiments, the microphone array will be substantially horizontal, substantially vertical or combinations thereof.

In certain embodiments, where the microphone array is substantially vertical the array will be made up of at least two microphones and at least one speaker.

Certain embodiments provide a device for use in telecommunications, comprising: at least three microphone elements arranged in an array to provide a certain phase and delay so as to achieve a null response in the vertical direction over a broad range of audio frequencies and with the facility to provide a response to sounds in the horizontal direction; and at least one loudspeaker arranged so that the audio from the speaker is substantially cancelled by the microphone array.

Certain embodiments provide a microphone array that is configured such that individual transfer functions are such that when the output signals are summed there is a null response in the vertical direction.

Certain embodiments provide a microphone array where the null response may vary from minus 10 db to 40 db with respect to the horizontal input response.

Certain embodiments provide an audio device: comprising at least three acoustic transducer elements arranged such that in use the audio device achieves substantially a null response in a substantially vertical direction over a range of audio frequencies ranging from 100 Hz to 10 KHz wherein the device provides a substantially flat response to input sounds in the horizontal direction for sounds ranging from 100 Hz to 10 KHz; and at least one speaker arranged such that the out put from the speaker is delivered in substantially equal levels to the at least three acoustic transducer elements such that in use the output from the speaker is sufficiently reduced to prevent acoustic feedback.

Certain embodiments provide an audio device wherein the loudspeaker is arranged so as to deliver substantially equal level signals to the microphone elements so that we the signals are combined the loudspeaker signal will be substantially reduced.

Certain embodiments provide an audio device with at least three microphones arranged in a substantially horizontal plane such that the microphones are configured to produce a substantially flat response to input sounds in the horizontal direction for sounds ranging from 100 Hz to 10 KHz; and at least one speaker arranged such that the out put from speaker is sufficiently reduced to prevent acoustic feedback. In certain aspects, the audio device will achieve a cancellation process such that the sound output from the speaker is substantially reduced in the out put of the microphone system in order to reduce the possibility of acoustical feedback.

Certain embodiments provide an audio device with a microphone array made up of at least three microphones wherein the array is configured such that when the signals from the microphone array are appropriately phased, weighted and summed the resultant signal is zero in the vertical direction but additive in the horizontal direction. In certain aspects, the microphone array can be further characterized such at that the frequency response in the horizontal direction falls of from high to low frequencies at a multiple of 20 dB per decade.

BRIEF DESCRIPTION OF THE DRAWINGS

Various aspects of the present disclosure will now be illustrated and further described with reference to the accompanying figures in which:

FIG. 2(*b*) shows a J-Tek All-Pass Filter Designer output parameters that may be used in certain embodiments;

FIG. 3(*b*) shows crossed pairs with a gain ratio of 2:1 with the elements placed on an ellipse with a 2:1 axes ratio;

FIG. 5(*b*) shows the response obtained by summing the four microphone elements shown in FIG. 5(*a*);

FIG. 19(*b*) show the phase relationship of the array illustrated in FIG. 19(*a*);

Figure 1:
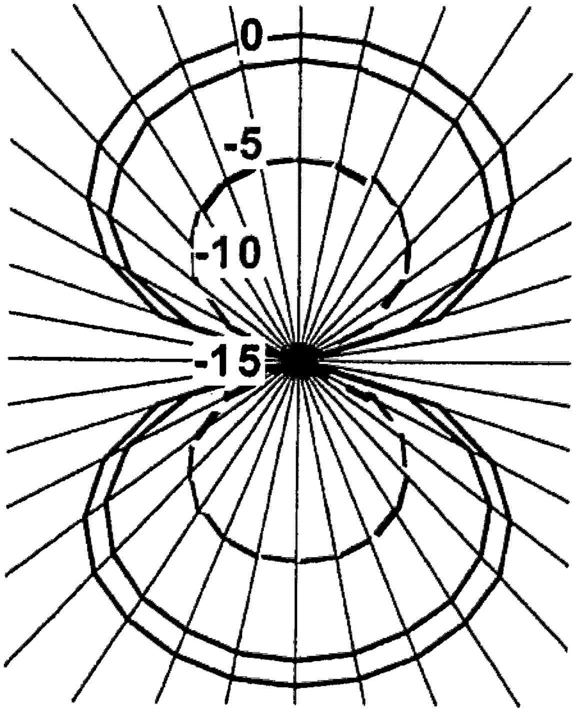
FIG. 1 shows the response given by a pair of equal sensitivity omni-directional microphones according to certain embodiments.

Various microphones may be used in the present disclosure, including but not limited to, dynamic microphones, electrostatic microphones, electret microphones, piezoelectric microphones, or combinations thereof. The microphone elements, may be omni-directional, bi-directional, uni-direction or combinations thereof. The desired combination of microphone elements may vary depending on what is to be accomplished in a particular embodiment or design configuration. In certain embodiments, the microphone elements will be configured to be in a circular, or substantially circular placement and evenly spaced, or substantially evenly spaced relative to each other. In certain embodiments, the loudspeaker will be centered in the circle created by the microphone elements. For example, this may be done with omnidirectional microphones placed in various diameters with a centered in the circumference created by the microphone elements. In certain embodiments, the diameter of the circle created by the microphone elements may be, for example, 20 mm, 30 mm, 40 mm, 50 mm, 60 mm, 70 mm, 80 mm, 90 mm, 100 mm, 110 mm, 120 mm, 130 mm, 140 mm, 150 mm, 160 mm, 170 mm, 180 mm or some other desired diameter.

The microphone elements may also be placed in an elliptical configuration resulting in an elliptical response in azimuth for the microphone system. Other configurations and arrangements of the microphone elements are possible.

In certain embodiments the loudspeaker and microphone elements are configured such that the path length from the loudspeaker to each of the microphone elements is equal, or substantially equal, so that the loudspeaker signal is cancelled, or substantially cancelled, in the output of the microphone system. It is of course possible in certain configurations to have one or more of the microphone elements having a different path length if this is desired or necessary for a particular application, as for example in a system configured to fit within a mobile phone case. In this case, if desired, conventional cancellation means may be employed in the signal processing circuitry of the microphone system. However, this may not be needed and will depend on the particular application and desired end result.

Certain embodiments shown satisfy the condition that the vector sum of the signals received by the individual elements is zero or there is high attenuation in the vertical direction or in a direction orthogonal to the plane in which the system is mounted. It will be apparent to those skilled in the art that many arrangements can be made in the position of a set of elements in a horizontal plane while retaining the high attenuation in the vertical direction. Embodiments are described which provide narrower, or substantially narrower, beam in azimuth. Other embodiments may be devised which provide high attenuation in certain azimuthal directions while others show examples of other azimuthal beam shapes. It will be apparent that some of the embodiments can be contained within a disk of 60 mm diameter and 5 to 10 mm high depending on the size of the loudspeaker and batteries chosen. In certain embodiments, the function that is achieve is a vertical, or substantial vertical, null in the direction away from the plane in which the microphones and loudspeaker are located and a substantially constant response in the desired azimuthal directions over the design frequency range, typically 300 Hz to 3 KHz or 200 Hz to 5 KHz. The shape of the structure with bi-directional microphones is typically small circular structures containing a loudspeaker and the electronics and battery.

Various speakers may be used with the present disclosure, including dynamic and piezoelectric types. In certain applications, it may be desirable for the speaker to be disposed within a zone of insensitivity. In other applications the speaker may be located outside the zone of insensitivity. In other applications the speaker may be located both partial in the zone of insensitivity and partial in a zone of sensitivity. In certain applications it may be desirable to locate the speaker so as to minimize acoustic echo within the system.

Certain embodiments described herein may be characterized in their uncompensated form, as a peak response at a frequency where the separation of oppositely phased microphones is approximately half a wavelength. These systems may require compensation for the fall-off in response below this frequency at 6 dB per octave or 12 dB per octave depending on the order and the particular embodiment. This may result in a constant, or substantial constant, beamwidth performance across the operation frequency range. In the systems described as "first order", this separation is equal, or substantially equal, to the diameter of a circle on which the elements are placed and the oppositely placed microphones have a phase difference of 180 degrees. In certain embodiments sometimes referred to as "second order", this separation is equal, or substantially equal, to the radius of a circle on which the microphone elements are placed. In these embodiments oppositely placed microphones are in phase but microphones placed at 90 degrees on the circuit have a phase shift of 180 degrees with respect to the first oppositely placed pair. In certain embodiments a centered microphone and/or cluster of microphones has a phase shift of 180 degrees with respect to the first oppositely placed pair.

Various families or embodiments are disclosed herein and it would be appreciated that combinations of members from different families or embodiments allow the realization of a variety of steerable directional beams. Certain embodiments retain the characteristic of a region of low sensitivity in the direction perpendicular to the plane of the arrays, or in the case of certain embodiments, in line with the array elements.

For certain embodiments (such as second order systems) disclosed herein, the sensitivity at an elevation angle of 45 degrees is 6 dB less than at an elevation of 0 degrees. For a microphone with a circular azimuth pattern, this will advantageously reduce the sensitivity to a person sitting at the side of a rectangular table due to the higher elevation of the mouth with respect to the speakerphone.

Certain aspects of the present disclosure are directed to microphones and/or microphone arrays that have pancake directivity for use in teleconferencing or other applications requiring rejection of vertical signals are described. These microphone systems have a certain amount of response null in the vertical direction.

Certain embodiments may be characterized as null in the vertical direction, and thus reducing reflections from the ceiling and reducing the echo sounds received by the system.

In certain application, the axis of sensitivity of the microphone can be oriented at an angle of from about 0 degrees (i.e., perpendicularly) to about 45 degrees relative to the horizontal surface. However, the 0 degrees arrangement is better adapted to a conference room table type speakerphone device.

In certain embodiments, when the signals from an array of microphones are appropriately phased, weighted and summed the resultant signal is zero, or substantially zero, in the vertical direction but additive, or substantially additive in the horizontal direction. Typically, in certain classes of systems the frequency response in the horizontal direction falls of from high to low frequencies at approximately multiples of 20 dB per decade depending on the design.

In certain embodiments, when the signals from an array of microphones are appropriately phased, weighted and summed the resultant signal is zero, or substantially zero, in the vertical direction but additive, or substantially additive in the horizontal direction. Typically, in certain classes of systems the frequency response in the horizontal direction falls of from high to low frequencies at approximately multiples of 40 dB per decade depending on the design.

In certain disclosed embodiments, the devices, methods and/or systems may be characterized in part having a vertical null response, a substantial vertical null response, a sufficient vertical null response, or an acceptable vertical null response over a bandwidth such as 300 Hz to 3.3 KHz, 300 Hz to 3 Khz, 300 Hz to 5 Khz, 300 Hz to 3.5 Khz or 150 Hz to 7.2 KHz.

In certain disclosed embodiments, the devices, methods and/or systems may be characterized in part by the fact that they have elevation responses that approximate Cosine (elevation angle) referred to as first order systems and $\text{Cosine}^2$(elevation angle) referred to as second order systems.

In certain embodiments the n microphones may have their signals combined so that the sum of the vectors representing the phase and amplitude of each elements contribution is equal to zero, or substantially equal to zero, over a desired bandwidth.

In certain embodiments the n microphones may have their signals combined so that the sum of the vectors representing the phase and amplitude of each elements contribution is equal to zero, or substantially equal to zero, over a desired bandwidth. In certain aspects, by n microphones we mean 2, 3, 4, 5, 6, 7, 8, 9, 10, 11, 12, 13, 14, 15 or 16. In certain aspects, by n microphones we mean at least 2, 3, 4, 5, 6, 7, 8, 9, 10, 11, 12, 13, 14, 15 or 16. In certain aspect, the sum of the vectors representing the phase and amplitude of each elements contribution is 4 db, 5 db, 6 db, 7 db, 10 db, 12 db, 14 db, 16 db, 18 db, 20 db, 22 db or 30 db less than the response in the desired direction over a desired bandwidth. In certain aspect, the sum of the vectors representing the phase and amplitude of each elements contribution in the vertical direction is 4 db, 5 db, 6 db, 7 db, 10 db, 12 db, 14 db, 16 db, 18 db, 20 db, 22 db or 30 db less than the response in the horizontal direction over a desired bandwidth. In certain aspects, by vertical direction we mean angles between 90 degrees and the angle from the vertical of a reflected sound wave from a person speaking in a conference situation. In certain aspects by vertical direction we mean angles between 90 degrees and the angle from the vertical of a reflected sound wave from a person speaking in a conference situation of up to 30 degrees. In certain embodiments, if the angle of arrival of the sound reflected from an above surface is greater than 45 degrees from the horizontal, then the attenuation of 6 db relative to the direct sound will be achieved in addition to path length attenuation. In certain embodiment, the amount of perceived reverberation received at the microphone may be reduced by 6 dB.

In certain arrangements, sound arising from a source that is equidistant from the microphone elements will be cancelled, or substantially cancelled, in the combined output of the microphone system. This allows for the positioning a loudspeaker in a position where its sound is cancelled, or significantly reduced, if desired. In certain arrangements, sound arising from a source that is equidistant from the microphone elements will be cancelled, or substantially cancelled, in the combined output of the microphone system. This allows for the positioning a loudspeaker in a position where its sound is cancelled, or significantly reduced, if desired. In certain aspects, sound arising from a source that is substantially equidistant from an array of at least two microphones substantial prevents oscillation. Thus feedback is reduced to the extent that oscillation is prevent creating greater echo cancellation. The combined signal output may be reduced by 10 dB or 20 dB or 30 dB from that of a single microphone element.

In general there are least four families disclosed herein. The first two have the additional characteristic that the microphone elements are arranged equi-spaced on a circle. A loudspeaker placed above or below these may be arranged to have equal path lengths to all elements. The combined output is thus not responsive to sound from that source. The different properties and characteristics of these families may be combined in various ways to achieve the desired properties or characteristics.

Within each family of embodiments its is possible to configure the microphones such that they have a high frequency section operating for example from 1 KHz to 5 KHz and a larger diameter (or longer) section operating from 200 Hz to 1 KHz. See for one example, FIG. 18 and another FIG. 43. This will permit improved signal to noise ratios.

In certain embodiments, the devices, methods and/or systems may have the same phase shift between elements at over all or many of the desired frequencies. The required phase shift for each element may be arranged by combining a “sine” component and a “cosine” component. This may be done by controlling the amplitude of the signals fed to the “0 degree” and “90 degree” inputs of a Hilbert Network for each element. In certain aspects, the gain between the two axes may be controlled by arranging the elements on an ellipse rather than a circle. A 2:1 ratio for family one or 2:1.4 for family two will result in a gain ratio of 2:1. Other arrangements are also contemplated, for example, where the gain between the two axes may be controlled by adjusting the differential gain between the “sine” component and the “cosine” component.

In certain disclosed embodiments, the phases and amplitudes of n elements in a horizontal plane are chosen so that they add to zero, or close to zero, in the vertical direction. Circularly symmetric systems may be designed where a delay is added to a symmetric group or a group may be physically offset. In certain implementations a vertical array may be arranged where the signals from individual elements are delayed and combined to produce a null response, or a substantially null response, in the vertical direction.

One useful calculation for reverberation time in rooms can be calculated by the Sabine formula: $RT_{60}=0.161\times V/A$ at 20° C.

Where V=room volume in $m^3$, $A=\alpha\cdot S$=equivalent absorption surface or area in $m^2$, $RT_{60}$=reverberation time in seconds, S=absorbing surface in $m^2$—more absorbency leads to lower reverberation times. If the area of surface of a room “seen” by a microphone is restricted, this may lead to a reduction in the reverberation time in the signal received by the microphone. This leads to improved clarity for the listener. Certain embodiments of the present disclosure use a wideband response “nulls”, resulting in responses in elevation and azimuth that are frequency independent, or substantially frequency independent. Additionally, reduction of the shorter time reflections leads to improved intelligibility.

Certain disclosed embodiments have a set of n microphones with the same, or substantially the same, sensitivity that are arranged in a plane, or substantially in a plane, and phase shifts are applied to the microphones such that these phase shifts sum to a multiple of 360 degrees, or approximately 360 degree. In these embodiments the sum will be zero, or substantially zero, in a direction perpendicular, or substantially perpendicular, to the plane.

Figure 11:
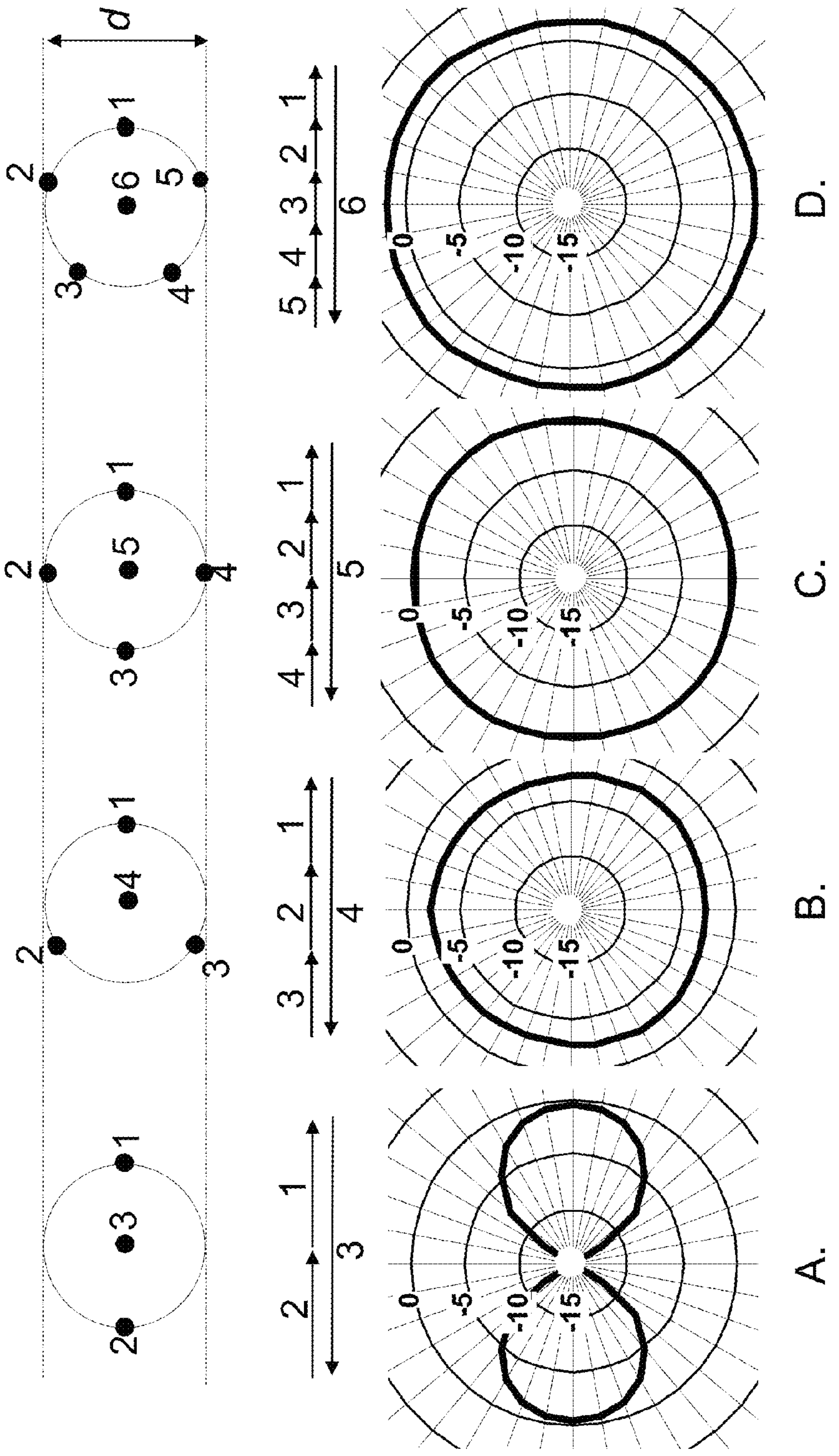
FIG. 11 illustrates a layout of elements for the certain embodiments with vector diagrams showing the phase relationship between the elements and the azimuth beam shapes.

In certain embodiments, a set of n/2 microphones in a plane with the same, or substantially the same, sensitivity have their signals added. This resultant signal is then subtracted from the combined signal from another set of n/2 microphones in the same plane or from a single microphone with n times the gain. If n is 3 or greater, the arrangement of the microphones on circles provides an approximation to circular symmetry in this system. FIGS. 11(*b*), (*c*) and (*d*) shows an arrangement of 5+1 microphones as an implementation of this approach. The middle row in FIG. 11 illustrates the phase relationship between the microphones while the bottom row shows the azimuth response. The frequency response of this system falls from high to low frequencies at 40 dB per decade giving rise to increased low frequency noise when the low frequency signals are amplified to give an overall flat, or substantially flat, response. It will be understood that in certain configurations, multiple microphones with might replace the centre group in this case if noise is a significant consideration.

Figure 17:
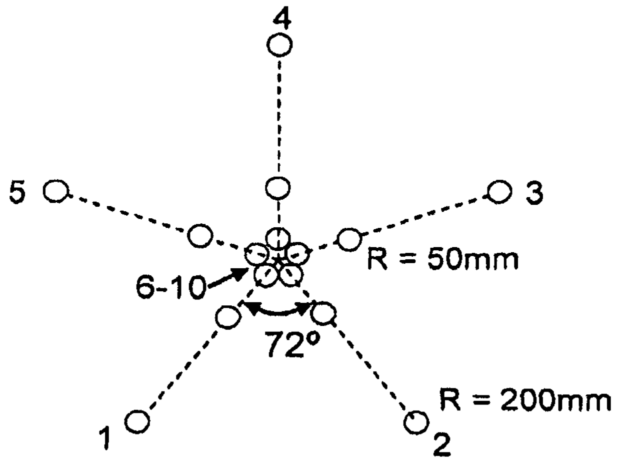
FIG. 17 illustrates a two stage five plus 1 array, according to certain embodiments.
Figures 18A, 18B:
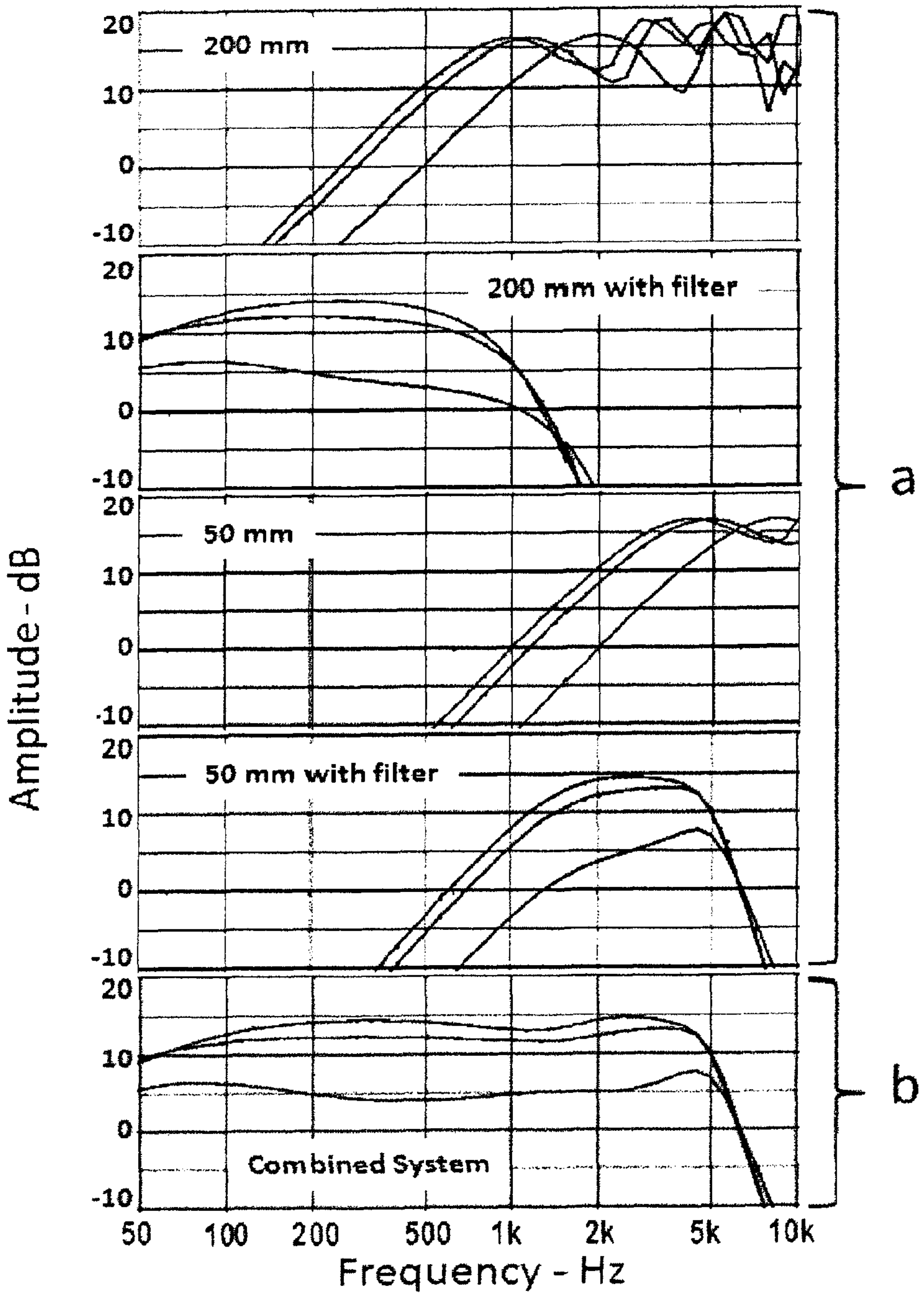
FIGS. 18(*a*) and (*b*) show the frequency response curves of the array illustrated in FIG. 17 with the effect of filtering and the combined response of the overall system.

For example, as illustrated in FIG. 17, this microphone array has two arrays of 5 microphone capsules, one equally, or substantially equally, placed on a circle of approximately 50 mm radius, the other equally spaced, or substantially equally spaced, on a circle of approximately 200 mm radius and a cluster of five capsules in a small circle in the centre. In this illustrated embodiment, five are used rather than one to preserve the signal/noise ratio. However, it would be possible to use one in certain applications. The 200 mm system is filtered with H(s)=100/((S+1)(S+1)) normalized to 100 Hz compensating for the 12 dB/octave and utilizing the resulting fall-off around 1 KHz. The 50 mm system is filtered with H(s)=(4+S)(4+S)/(S+1)(S+1) normalized to 1 KHz. The two responses are then subtracted. This is illustrated in FIG. 18*a* for the individual sections and 18*b* for the overall response.

In certain embodiments, a set of n microphones in a plane where each successive microphone has its signal phase shifted by approximately 360/n degrees. The phase shifted signals are combined to give the overall response. The phase shifting may be performed by using pairs of circuits giving Hilbert Transform approximations. The frequency response of this system falls from high to low frequencies at approximately 20 dB per decade.

Figure 19A:
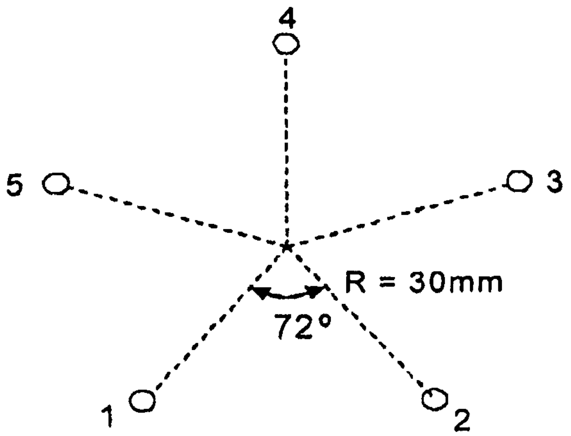
FIG. 19(*a*) illustrates placement of microphone in another array, according to certain embodiments.
Figure 19B:
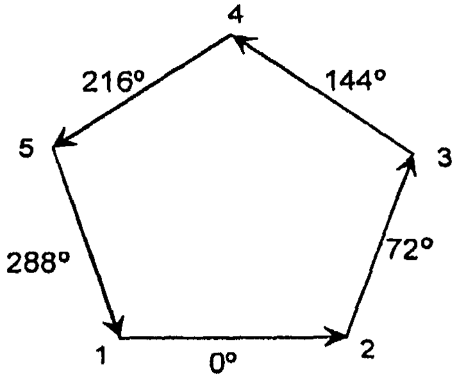
Figure 20:
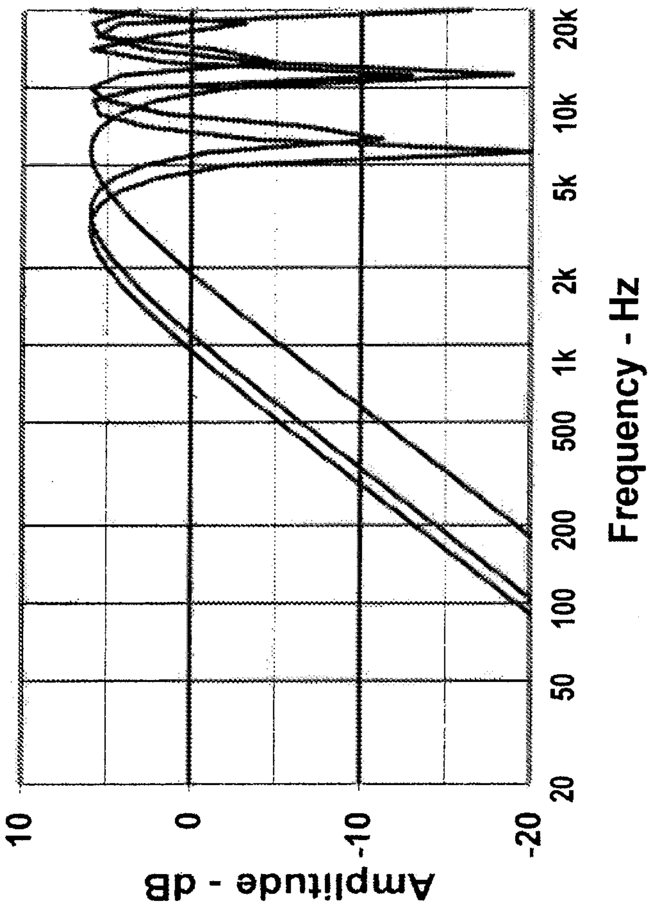
FIGS. 20(*a*) and (*b*) show the frequency response curve of the array illustrated in FIG. 19.
Figure 20:
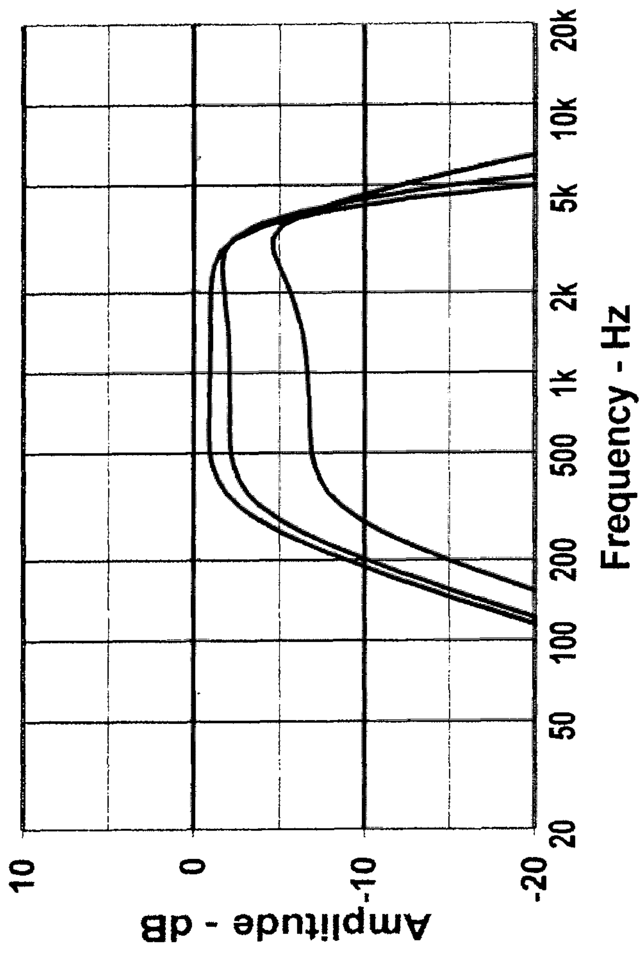
Figure 21:
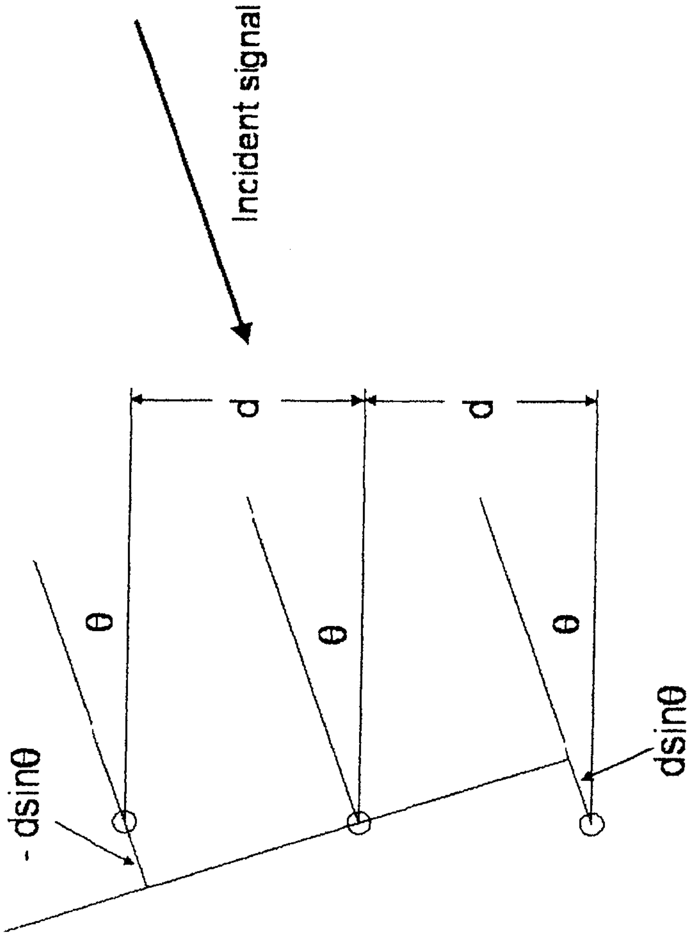
FIG. 21 illustrates the geometry of line microphone, according to certain embodiments.

For example, uniformly, or substantially uniformly, spaced circular arrays are configured where the phases of the microphones add to a multiple of 360 degrees. Where that sum is 360 degrees the slope of the response is approximately 20 dB per decade. If the sum is 2×360=720 degrees, then the slope is approximately 40 dB per decade. In the example illustrated in FIG. 19(*a*) the phases are summed to 360 degrees and the placement of microphone array is shown. FIG. 19(*b*) show the phase relationship of the array illustrated in FIG. 19(*a*). FIG. 20(*a*) shows the response before and FIG. 20(*b*) shows the response after filtering with simple correction circuit. It should be noted that this only attempts to cover one decade for the speech range.

Figure 16:
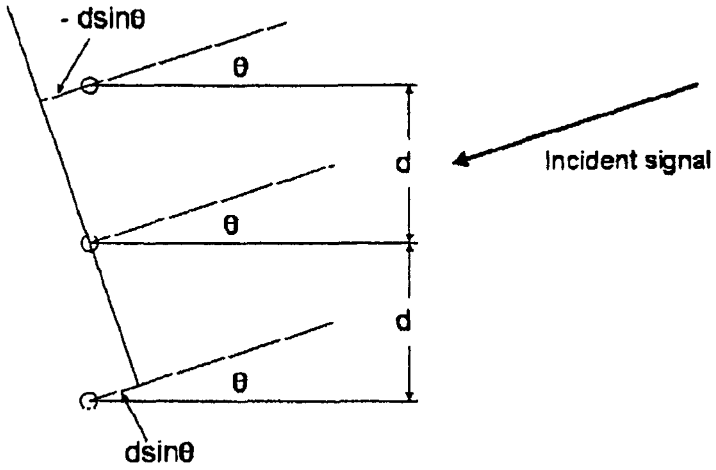
FIG. 16 illustrates the signals from three microphones which have been appropriately delayed and combined with appropriate amplitudes so as to produce a null in the vertical direction.

In certain embodiments, the signals from at least three microphones are appropriately delayed and combined with appropriate amplitudes so as to produce a null, or substantial null, in the vertical direction, or substantially in the vertical direction. FIG. 16 illustrates the signals from an exemplary three microphones arrangement which have been appropriately delayed and combined with appropriate amplitudes so as to produce a null in the vertical direction. These microphones may be equally, or substantially equally spaced. However, that may also be configured with other spacing arrangements.

For example, in certain applications, the two microphones may be used when mounted close to a reflecting plane so that the third is produced by reflection.

Figure 2A:
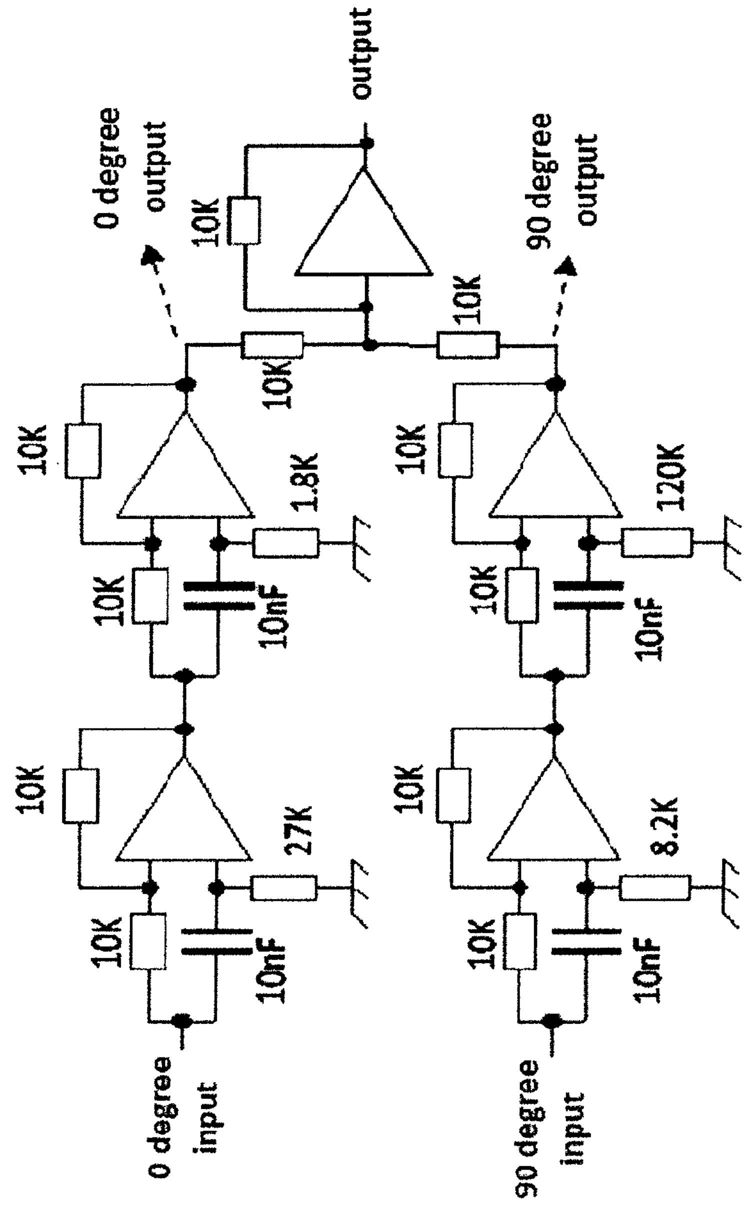
FIG. 2(*a*) shows a Hilbert circuit that may be used in certain embodiments.
Figure 2B:
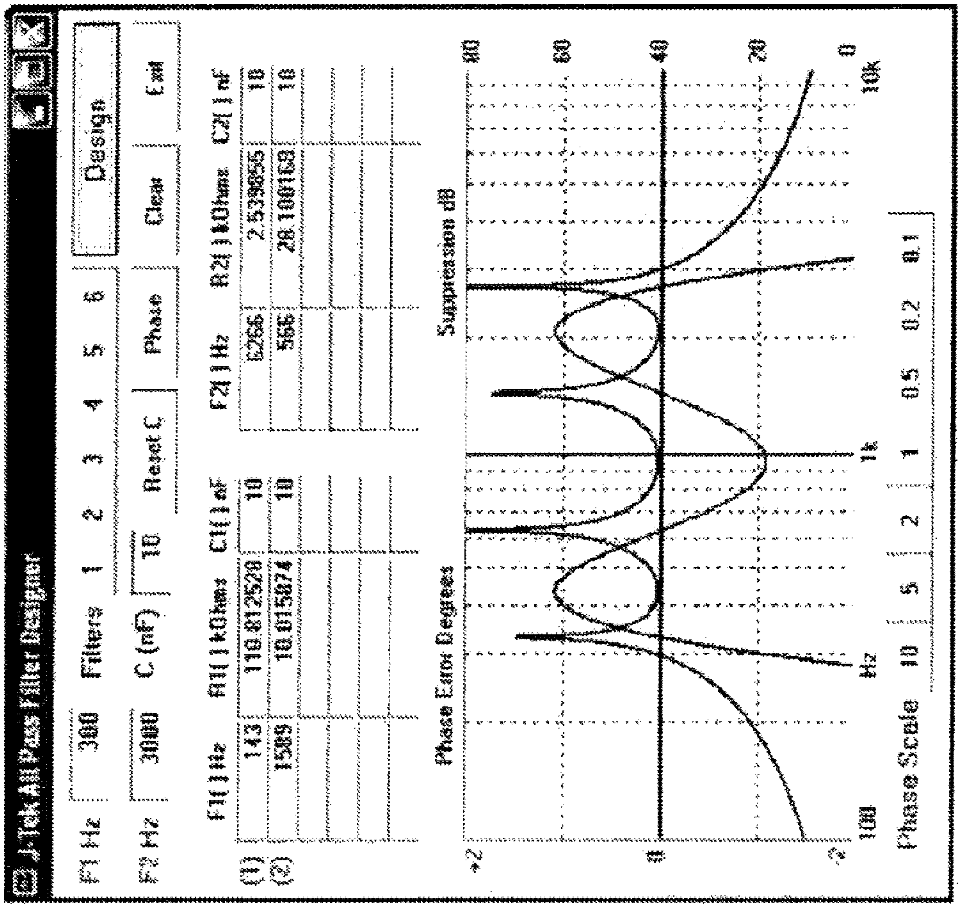
Figure 3:
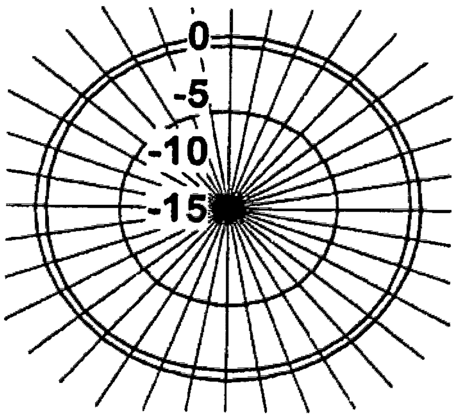
FIG. 3(*a*) shows a response of "crossed pairs" at 0° elevation (outer circle), 30° (next circle), 60° (inner circle), in accordance with certain embodiments.
Figure 3B:
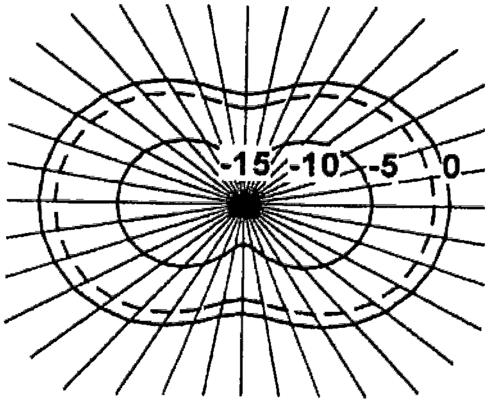
Figure 8:
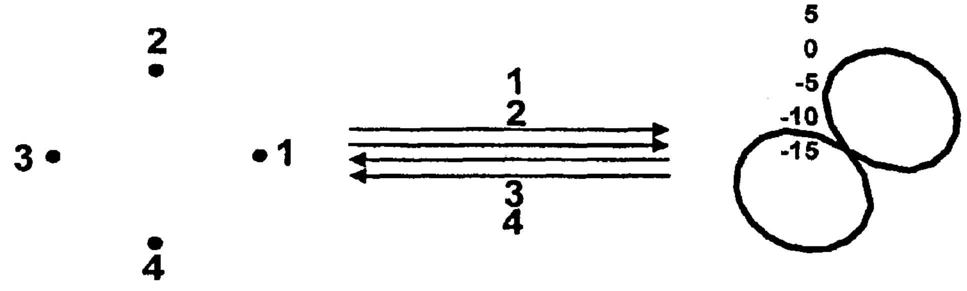
FIG. 8 illustrates an example of a steerable "FIG. 8" type beam at 45 degrees.

In certain embodiments, a pair of equal sensitivity, or substantially equal omni-directional microphones set apart by a distance d in a horizontal plane and in anti-phase gives rise to a bi-directional figure eight type response with a maximum amplitude response at the frequency $F_{max}$ where d=wavelength/2 and a response that falls off at 6 dB per octave at lower frequencies. See FIG. 1, which shows a typical figure eight pattern for a pair of microphone elements in anti-phase. A compensation circuit with a response that rises at 6 dB per octave over the desired frequency range results in a flat response up to $F_{max}$. In the horizontal plane this response is proportional to the cosine of the azimuth angle. The elevation response is also proportional, or substantially proportional, to the cosine of the elevation angle, having a null response in the vertical direction, or substantial vertical direction. A second pair of compensated microphones may be added in the horizontal plane with their axis at right-angles, or substantially at right angles, to the first pair and they will typically show a bi-directional response. If the signals from these microphones are now combined through a circuit that phase shifts one with respect to the other by 90 degrees (a Hilbert Network as shown in FIG. 2) the resulting system of "crossed pairs" has a uniform response, or substantially uniform response, at the azimuth (horizontal) angles but a elevation (vertical) response proportional to the cosine of the elevation see FIG. 2(*a*). Such microphone embodiments are characterized at least in part by low sensitivity to signals from higher elevation angles and results in a reduction in reverberation time. In certain situations this may be of useful if, for example, the ceiling is very reflective and the conference table is also very reflective. In certain embodiment, adjustments to the gain of one microphone pair relative to the one at right-angles result initially in an elliptical azimuth beam which gradually changes to the FIG. 8 pattern of a single microphone pair. This allows the system to be adjusted to have a gain ratio of approximately 2:1 between the two axes. FIG. 3(*a*) shows a response of "crossed pairs" at 0° elevation (outer circle), 30° (next circle), 60° (inner circle), according to certain embodiments. FIG. 3(*b*) shows crossed pairs with a gain ratio of 2:1. The direction finding properties may be used to enhance the performance of systems where there are multiple speakerphone systems. If two speakerphones are placed towards either end of a long table, the direction finding characteristic will allow the selection of the microphone closest to the person speaking and the at least partial suppression of the other in order to reduce noise and reverberation. This is a selection process where measurements are used rather than a feedback process determined by the relative amplitudes of the signals received by the two systems.

In certain embodiments the speakerphone may be configured to "learn" the optimum gain for a particular direction and person speaking so that this setting can be restored whenever the person speaks.

In certain embodiments the sensitivity of the speakerphones may be adjusted with azimuth angle to allow equal total signal levels for various positions around the table.

If desired, the table dimensions and speakerphone locations may be set up with appropriate computer software. However, in certain applications a number of presets may be provided.

Furthermore, it is understood that the principles disclosed herein may be extended to three or more speakerphones in a predetermined arrangement.

Figures 4A, 4B:
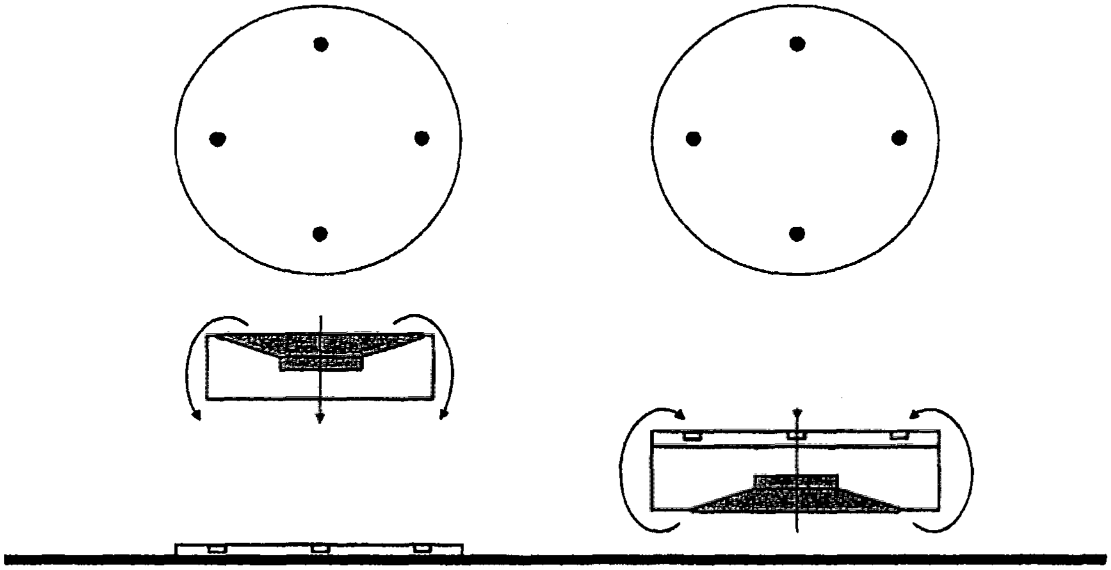
FIGS. 4(*a*) and (*b*) shows a loudspeaker that may be mounted above or below the microphone arrays, in accordance with certain embodiments.
Figures 26A, 26B:
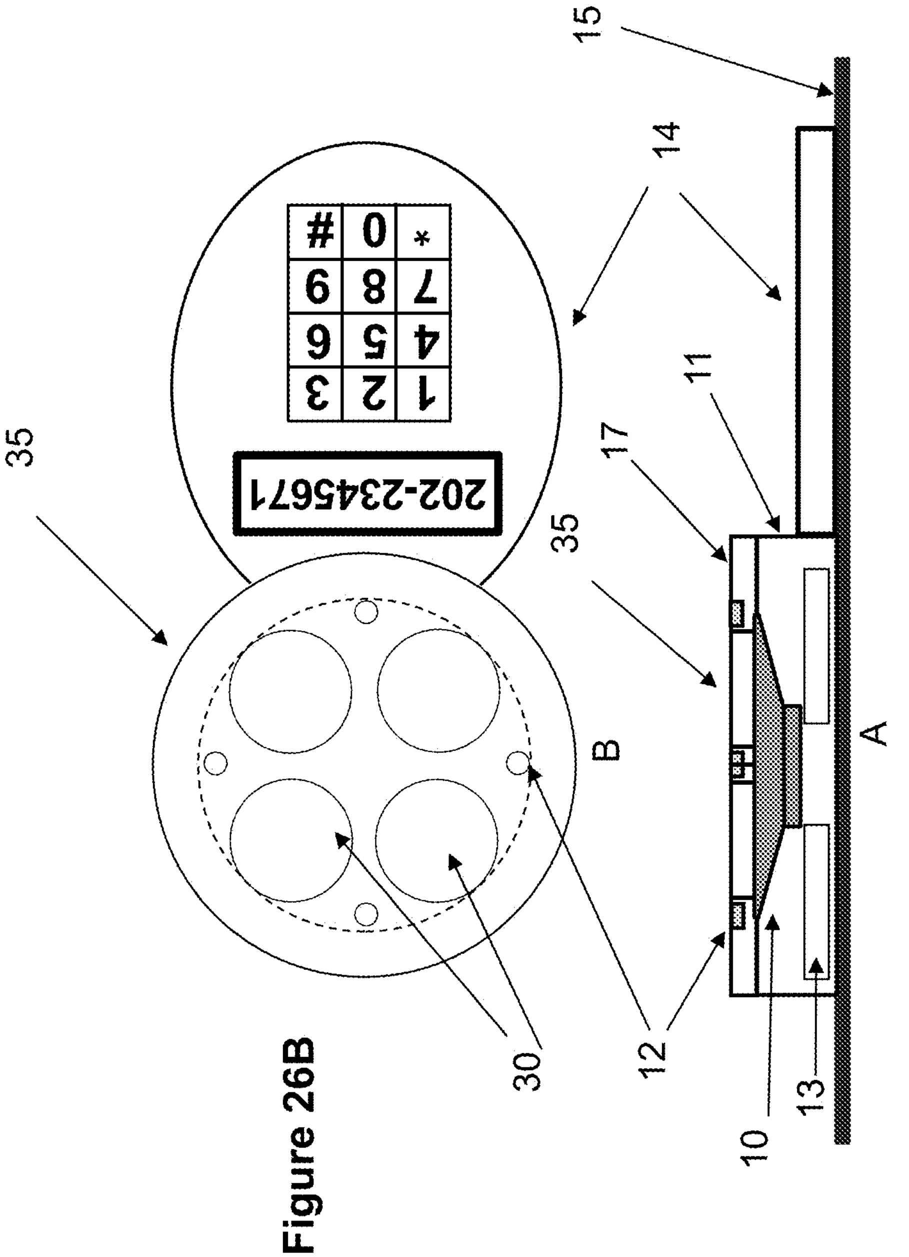
FIGS. 26(*a*) and (*b*) illustrate a schematic for speakerphone device in side view and top view in accordance with certain embodiments.
Figures 32A, 32B:
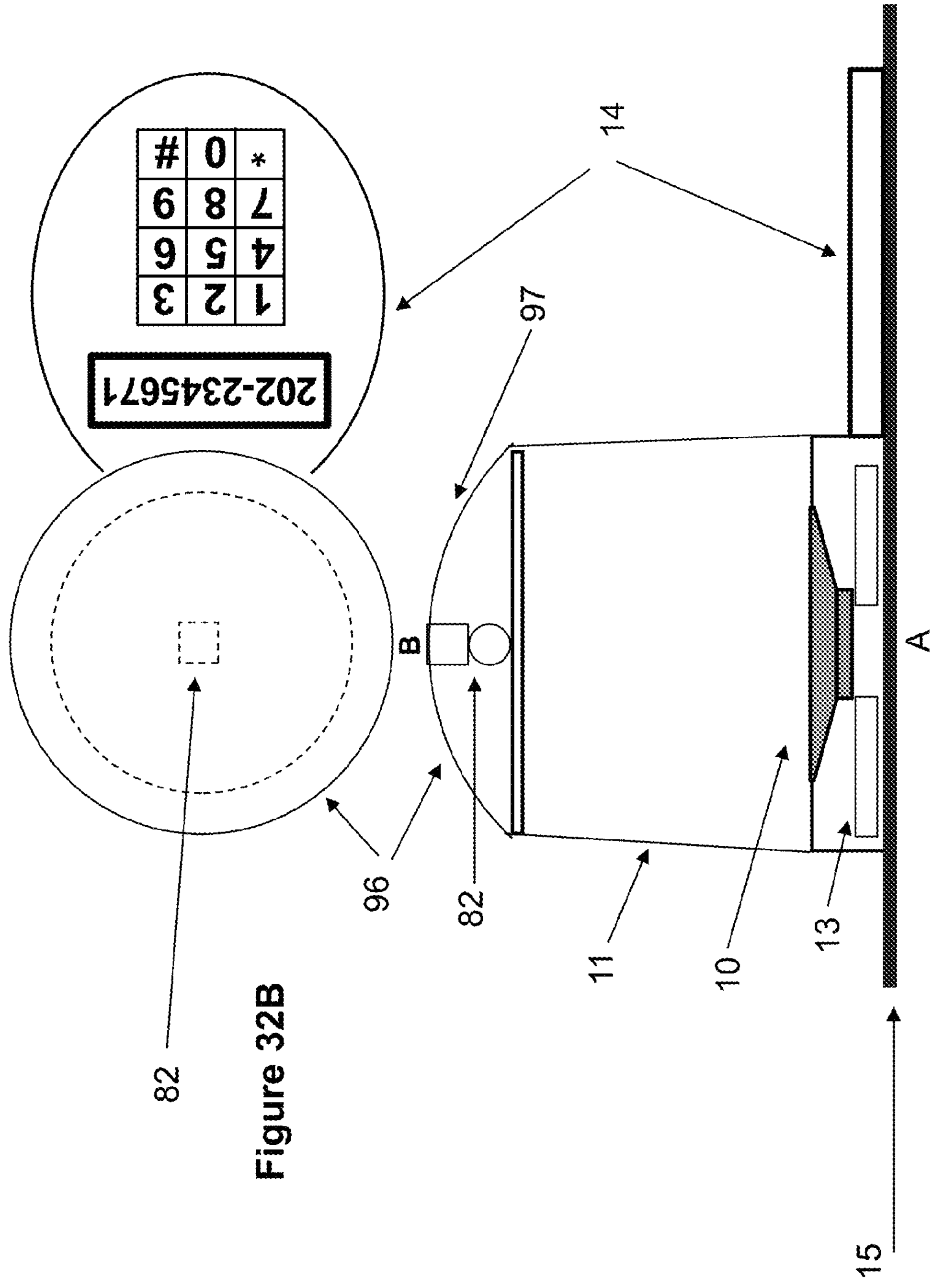
FIGS. 32(*a*) and (*b*) illustrate a schematic for speakerphone device in side view and top view in accordance with certain embodiments.

In certain embodiments, the direction finding approach here may beneficially be used to determine phasing for other types of beam forming arrays used in these environments. In certain embodiments, it is possible to place a loudspeaker in positions where it is equally distant, or substantially equal distant, from all microphones. The combined signal from these microphones will then be zero, or substantially zero. For example, as shown in FIG. 4, if the microphones are placed on a circle concentric, or substantially concentric with the outer rim of a mounting surface, a loudspeaker placed centrally below the mounting surface will satisfy the equidistance criterion. A loudspeaker placed centrally above would also satisfy this condition. Various arrangements of symmetric holes through the mounting surface can also be seen to satisfy this condition. In FIG. 26 and FIG. 32, a set of four holes provide this symmetry. In FIG. 40, where there are six microphones, 6 holes provide the necessary symmetry. In a variant of this in FIG. 30 the microphones are incorporated into a mobile phone. Two slots at the side allow for equal distances from a centrally placed loudspeaker element to each of the microphones.

In certain embodiments or configurations, the systems of microphone elements where n microphone elements with equal sensitivity, or substantially equal sensitivity, can be arranged equi-spaced, or approximately equi-spaced, around a horizontal circle. If the phase (in degrees) of each element relative to element 1 is equal, or approximately equal, to its angle from element 1 in degrees then the sum of the signals from all microphone elements will be approximately zero in the vertical direction. Thus, using the disclosed microphone arrays it is possible to construction a device and/or system of microphones with the characteristic of a broadband null in the vertical direction.

Figure 5A:
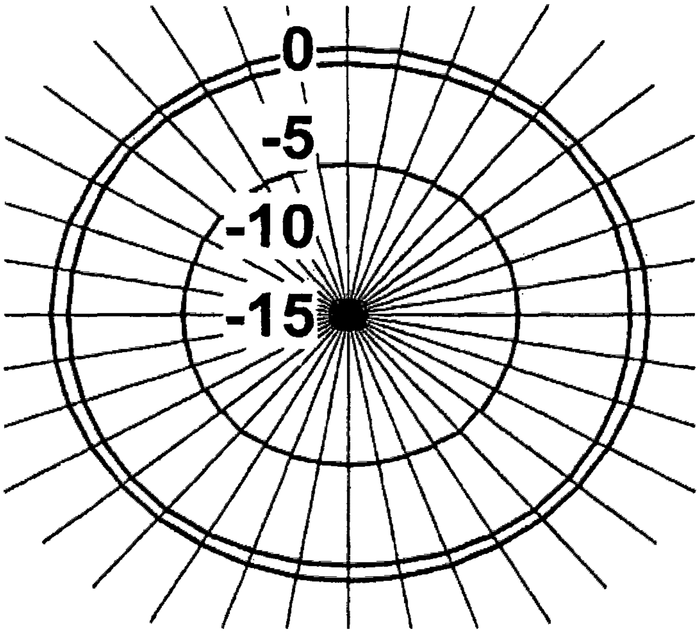
FIG. 5(*a*) shows the "crossed pairs" response at elevation angles of 0°, 30°, 60° of devices in accordance with certain embodiments.
Figure 5B:
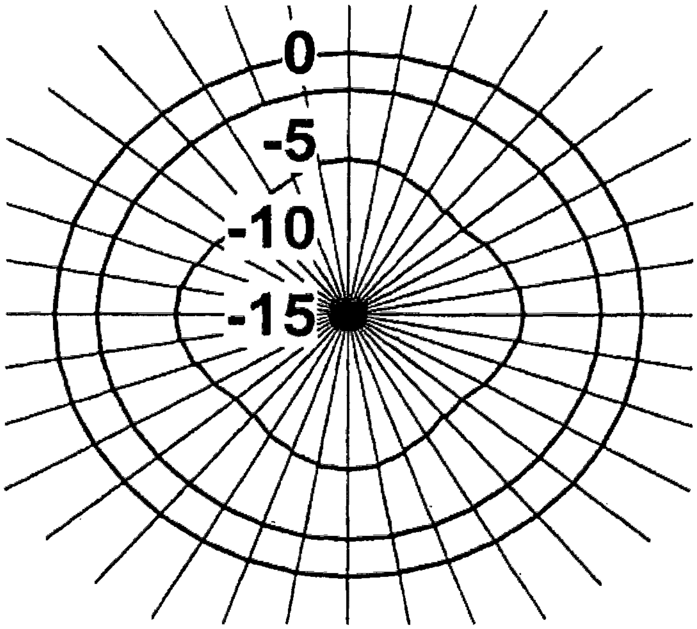

In certain embodiments, directional finding properties may also be present. For example, if the signals from the two outputs of the Hilbert Circuit are multiplied by a signal formed by summing the signals from the four microphone elements which is then passed through one section matching, for example, the 0 degree side of the original Hilbert Circuit, the resulting products are the sine and cosine of the azimuth angle for the current person speaking. Thus, the direction of a single person speaking is uniquely identified in a single measurement averaged over a period of one, two or even five seconds. In certain aspects, to preserve a satisfactory level of accuracy, a filter, or other means, may be used to restrict the maximum frequency of the signal used in this calculation to less than half $F_{max}$. Under these circumstances, the azimuth response of the summed microphone elements is circular. For example, see FIG. 5. FIG. 5(*a*) illustrates "crossed pairs" response at elevation angles of 0°, 30° and 60°. FIG. 5(*b*) illustrates the response obtained by summing the four microphone elements. The outer circle shows the horizontal response for the reference signal obtained from the summed microphones at a frequency Fmax/3. The next circle is Fmax/2 and the inner cruciform response is at Fmax. The phase difference between the normally processed "crossed pairs" signal and the summed signal is equal to the azimuth angle.

In certain embodiments, a microphone array is provided wherein the system is configured for direction finding where a reference signal is multiplied by a sine and cosine component from the cross figure eight pairs. For the reference signal, a system using the existing four elements plus a centre element (see FIG. 11(*c*)) could be used. This measurement could be made over a restricted frequency range around 1 KHz, or could be from 800 Hz up to 3 KHz, or could operate over the range of 300 Hz to 3 KHz range.

Figure 6:
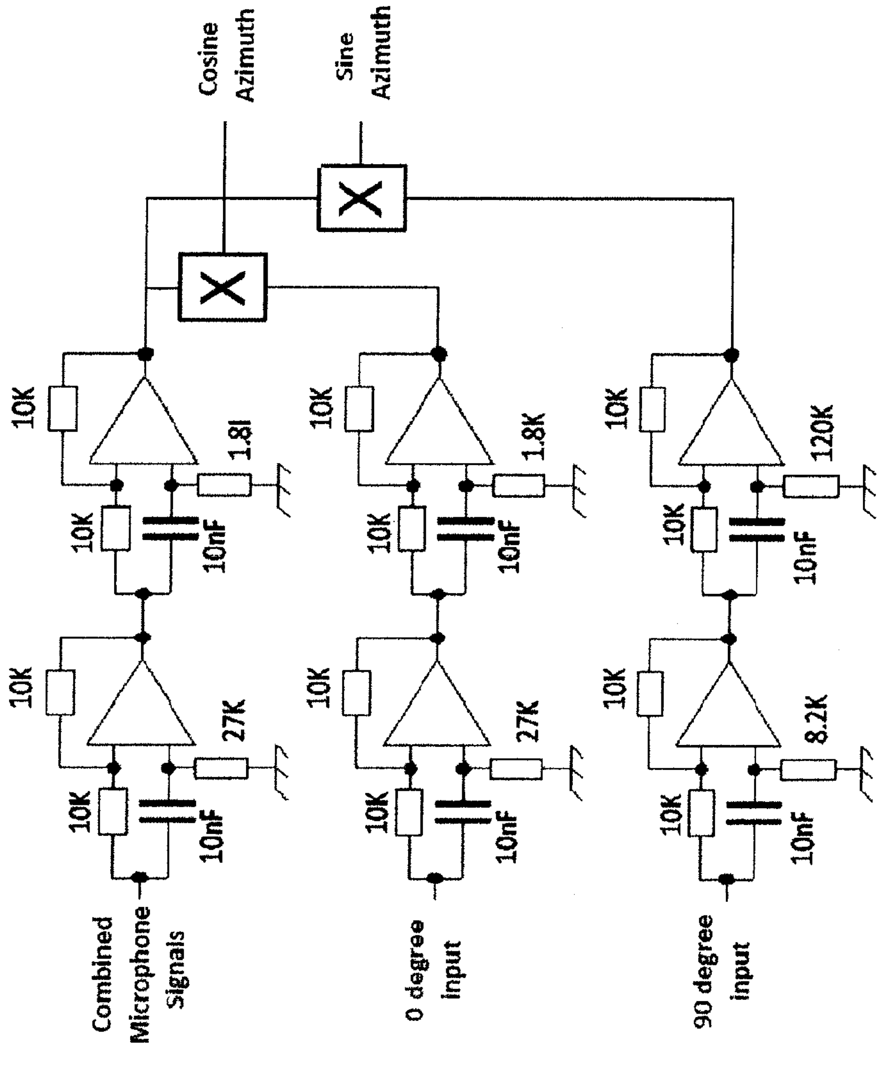
FIG. 6 shows a circuit that may be used to obtain the directional information, in accordance with certain embodiments.

FIG. 6 illustrates a circuit that may be used to obtain the directional information in accordance with certain embodiments.

Figure 7:
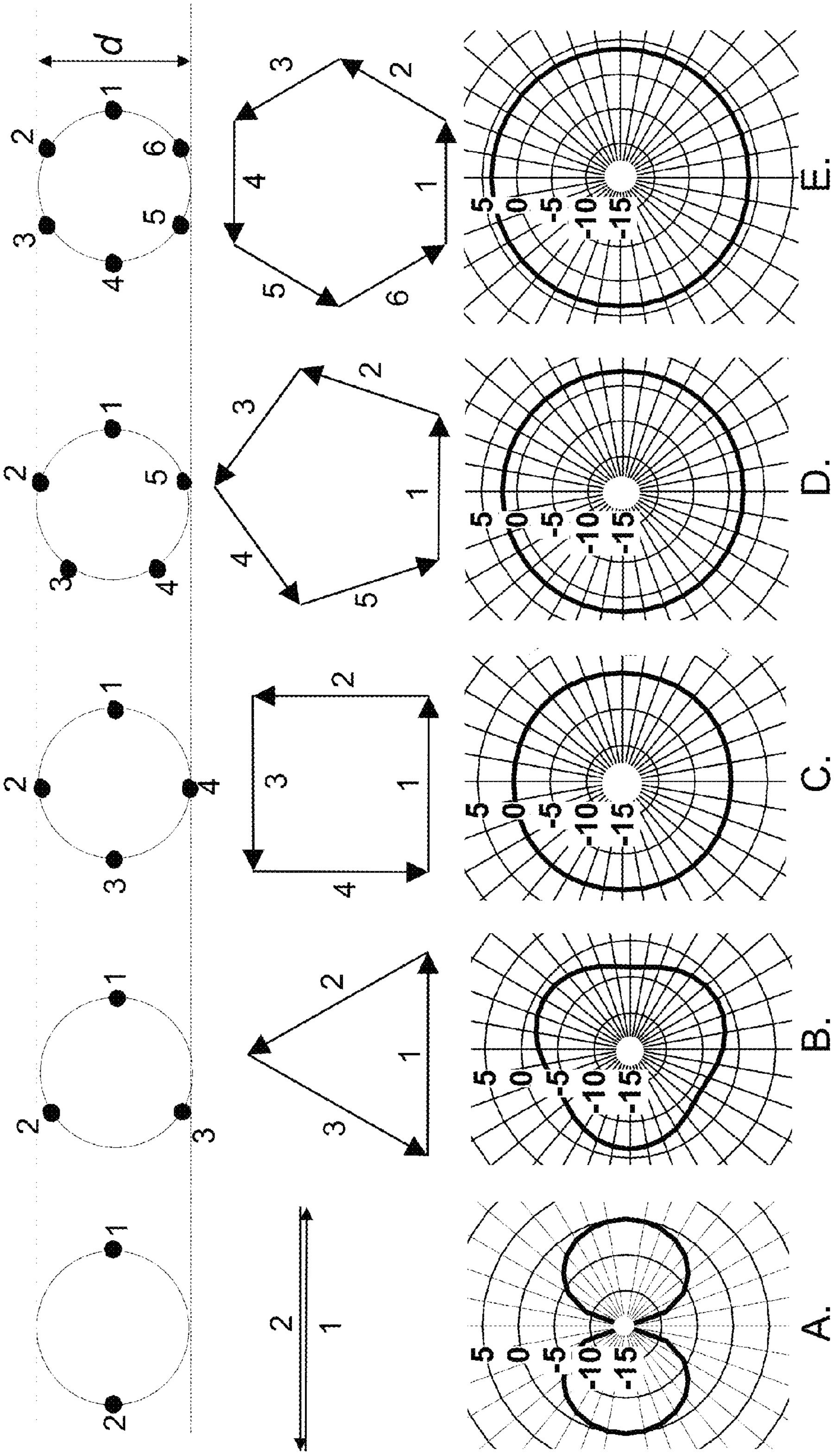
FIG. 7 illustrated the layout of elements for certain embodiments with vector diagrams showing the phase relationship between the elements and the azimuth beam shapes.

The configuration and arrangement of the microphone can vary. In general terms certain embodiments permit the construction of microphone systems or devices that consist of n microphones of equal gain, or substantially equal gain, arranged on a horizontal, or substantially horizontal plane, in a circle type configuration of diameter d where d is equal to half a wavelength at the desired highest frequency of operation of the system. The first microphone is placed on a reference line (x axis). The phase of each successive microphone is equal to its angle from the x axis. FIG. 7 illustrates some of the possible layouts of elements according to certain embodiments with vector diagrams showing the phase relationship between the elements and the possible azimuth beam shapes. In FIG. 7, the type A arrangements are similar in response to a bi-directional microphone (e.g. a ribbon microphone). The type C are similar in characteristic to crossed bi-directional microphones but with a broadband 90 degree phase shift between the two bi-directional pairs. In certain embodiments, a similar result could be achieved using two bi-directional microphones such as ribbon microphones, each connected to an input of a Hilbert network. They would not, however be in the one plane. In the types D and E arrangements, the phase for each element is provided by determining a "sine" and "cosine" component for the phase for each element and adding these to the respective inputs of the Hilbert circuit. The same direction finding capabilities apply to the signals at the output of the Hilbert circuit in these cases. The gain difference between the two axes can be controlled by adjusting the gain of one input of the Hilbert Network.

In certain embodiments, using the configurations illustrated in C of FIG. 7, it is possible to arrange the relative phases of elements 1 and 3 at approximately 0 and 180 degrees and elements 2 and 4 are also set to approximately 0 and 180 degrees, an azimuth beam shape similar to A but rotated by 45 degrees. This is further illustrated in FIG. 8. Using the illustrated configurations, the beam may be rotated to an arbitrary or desired angle by combining a proportion of the signal from 1 and 3 proportional to the cosine of the desired angle and a proportion of 2 and 4 proportional to the sine. Thus, in certain embodiments a "steerable" figure eight beam may be created. In certain embodiments, the measured sound direction may be used to adjust the axis of this bi-directional system. Thus, the disclosed figure eight patterns may be rotated and may used on its own as a directional system. Additional, such configurations will substantially reduce the amount of interfering noise as the area of the room and therefore the proportion of the reflected sound "seen" by the microphone array is reduced.

Figure 9:
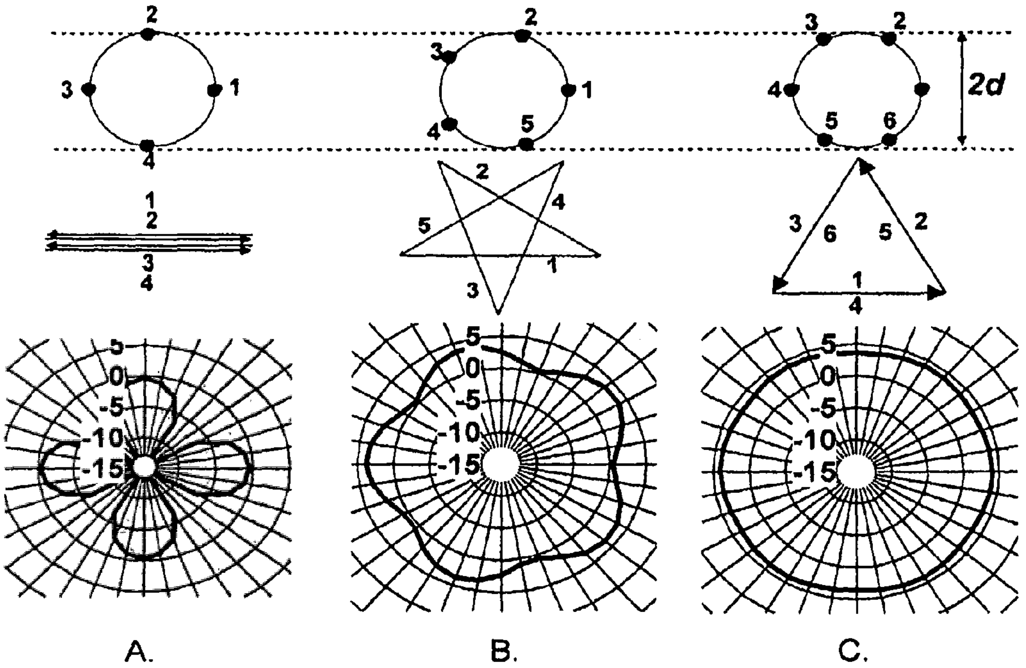
FIG. 9 illustrates the layout of elements for the certain embodiments with vector diagrams showing the phase relationship between the elements and the azimuth beam shapes.

In certain embodiments, microphone arrays may be configured that comprise at least three microphones of equal gain, or substantially equal gain, arranged on a horizontal plane, or substantially horizontal plane, in a circle of diameter 2d where d is approximately equal to half a wavelength at the desired highest frequency of operation of the system. The first microphone is placed on a reference line (for example, on an x axis). The phase of each successive microphone is equal to twice its angle from the x axis. For example, in certain embodiments, the three element configuration with phase steps of 240 degrees (or minus 120 degrees) is similar in characteristics to that shown in FIG. 7(*b*) with reversed phases. FIG. 9 illustrate layouts of the elements for the certain embodiments with vector diagrams showing the phase relationship between the elements and the azimuth beam shapes.

Figure 10:
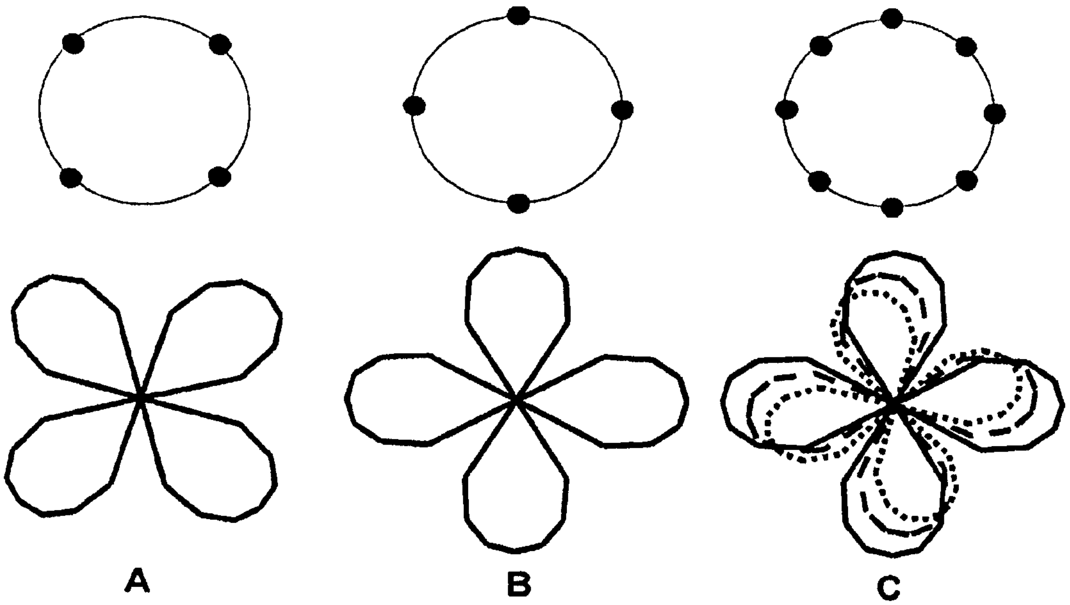
FIG. 10 illustrates a response for FIGS. 9(*a*) with (*b*) showing the result for a set of microphone elements displaced by 45° and the beam rotation obtained by combining proportions of (a) and (b)

This system has a response with a maximum amplitude response at the frequency $F_{max}$ where d=wavelength and a response that falls off at approximately 12 dB per octave at certain lower frequencies. A compensation circuit with a response that rises at 12 dB per octave over the desired frequency range results in a flat response up to $F_{max}$. In the horizontal plane this response is proportional to the cosine squared of the azimuth angle. The approximate 12 dB per octave fall off results in a substantial loss of signal/noise ratio, i.e., the S/N ratio at 300 Hz is 40 dB worse than at 3 KHz. The four element embodiment illustrated in FIG. 9(*a*) may be used as part of a directional microphone system. FIG. 10 illustrates the response for the embodiments shown in FIGS. 9(*a*) with (*b*) and illustrates the results for a set of microphone elements displaced by 45° and the beam rotation obtained by combining proportions of (a) and (b). This particular embodiment would have approximately a 3 dB drop in level at 22.5°.

Certain disclosed embodiments may consist of n microphones of equal gain and equal phase arranged on a substantially horizontal plane in a circle of diameter 2d where d is approximately equal to half a wavelength at the desired highest frequency of operation of the system and an additional microphone at the centre of the circle with gain n times that of the other elements and a phase shift of 180 degrees. FIG. 11 illustrates the layout of elements for certain embodiments with vector diagrams showing the phase relationship between the elements and the azimuth beam shapes. Thus, certain embodiments have a response with a maximum amplitude response at the frequency $F_{max}$ where d=wavelength and a response that falls off at approximately 12 dB per octave at lower frequencies. A compensation circuit with a response that rises at 12 dB per octave over the desired frequency range results in a substantially flat response up to $F_{max}$. In the substantially horizontal plane this response is approximately proportional to the cosine squared of the azimuth angle. It will be seen that a loudspeaker may be placed below the microphone array with appropriately placed holes in the baffle so that the phase of the signals received by the centre microphones equals that received by the outer microphones thus achieving similar cancellation to the earlier systems. Furthermore, the embodiments illustrated in FIG. 10(*a*) may be useful in directional microphone systems.

Figure 14:
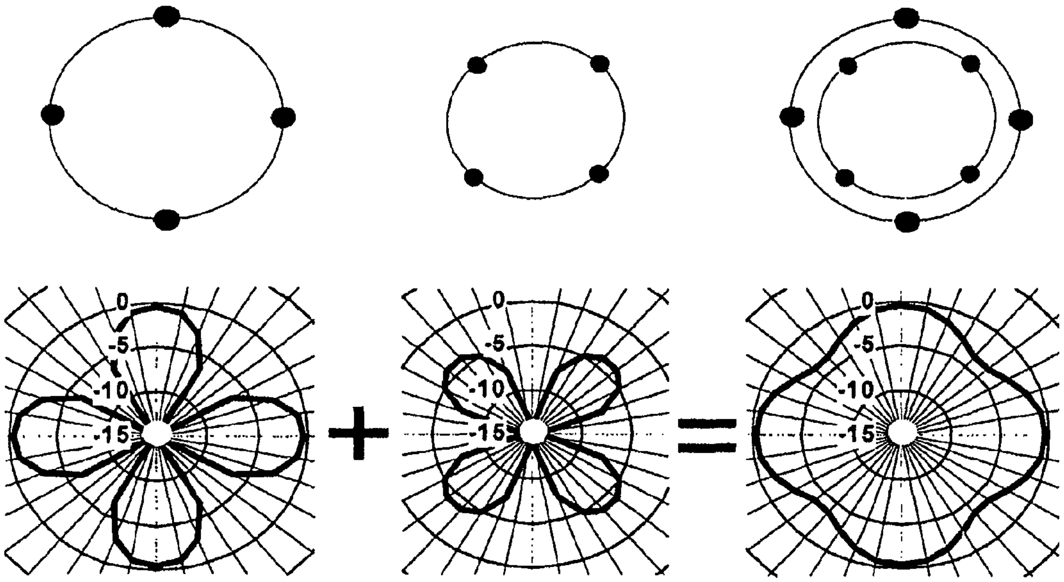
FIG. 14 illustrates the effect of combining the embodiment illustrated in FIG. 9*a* with a rotated similar embodiment with a smaller diameter to provide a "square" beam.
Figure 15:
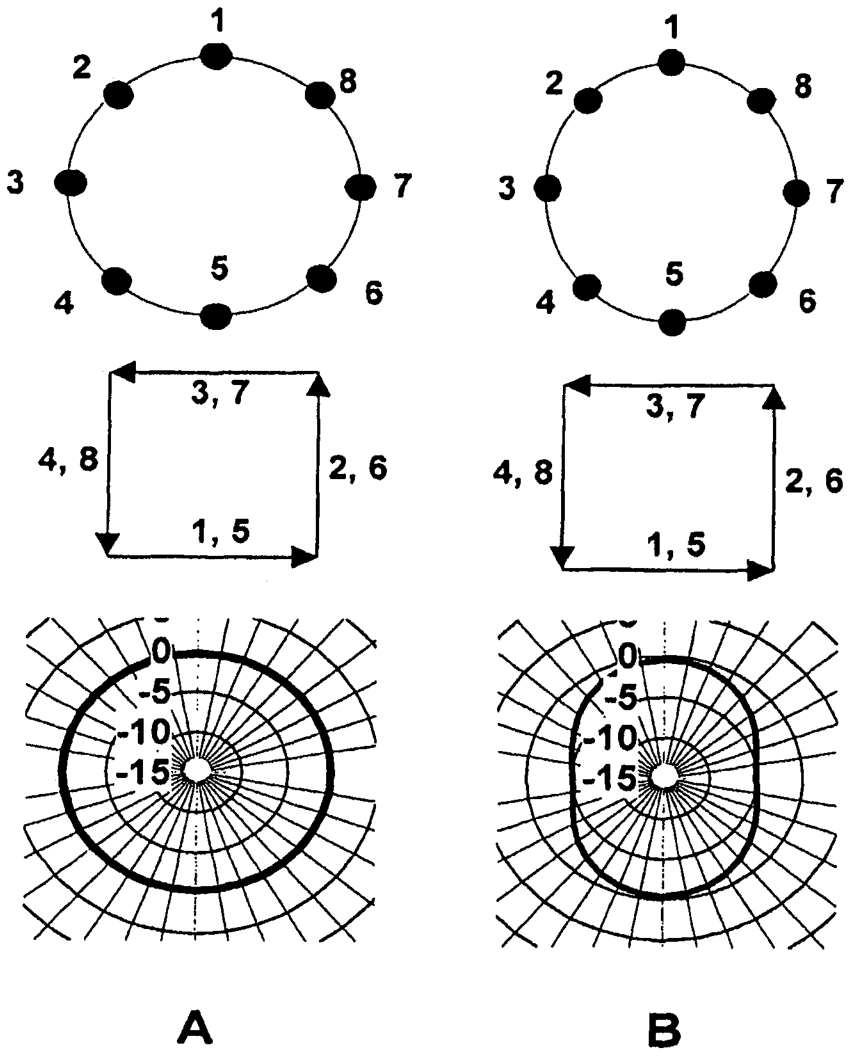
FIG. 15 illustrates the azimuthal beam shape resulting from the placement of the microphones on an ellipse with axis ratio of 0.75.

In certain embodiments, the azimuthal response characteristics of the microphones arrays may be varied for example by arranging the microphones on an ellipse rather than a circle, which can be shown to provide different gain on the two axes. In certain embodiments, such as those of FIG. 7 and FIG. 11, this may be achieved by adjusting gains of different microphones. FIG. 15, illustrates the case where the elements are arranged on an ellipse with a axis ratio of 0.75. Such arrangements make it more difficult to arrange cancellation of the loudspeaker signal in the combined system. FIG. 14, illustrates a system that provides a "square" beam that may be useful for large square conference tables.

Certain embodiments may be constructed from at least one vertical array of microphones wherein the signal from the individual microphones is appropriately adjust to give a broadband null, or substantial null, in the vertical direction. In these embodiments, the microphone array system has a response with a maximum amplitude response at the frequency $F_{max}$ where d=wavelength/2 and a response that falls off at approximately 12 dB per octave at lower frequencies. For example, in the range of $F_{max}/100$ to $F_{max}$. A compensation circuit may be used with a response that rises at approximately 12 dB per octave over the desired frequency range results in a flat response up to $F_{max}$. In the substantially vertical plane this response is proportional to the cosine squared of the elevation angle.

Figure 22:
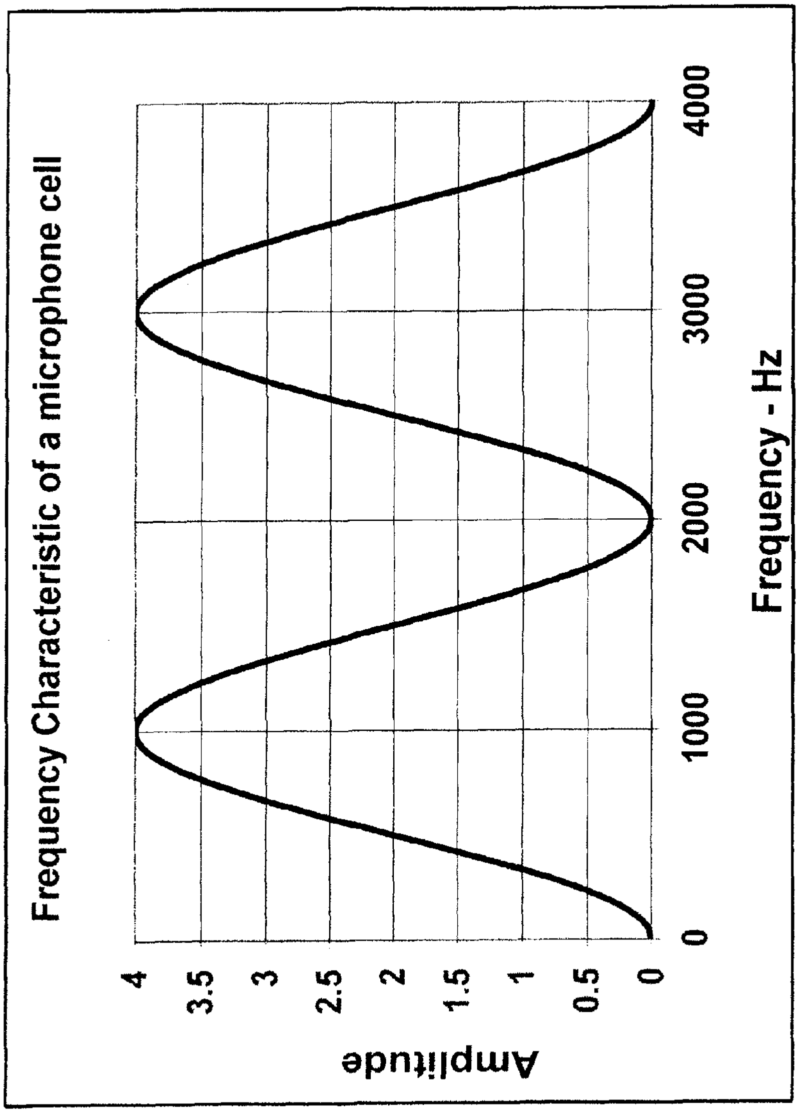
FIG. 22 illustrates the linear amplitude, linear frequency characteristics of a microphone cell with 150 mm between microphones, according to certain embodiments.
Figure 23:
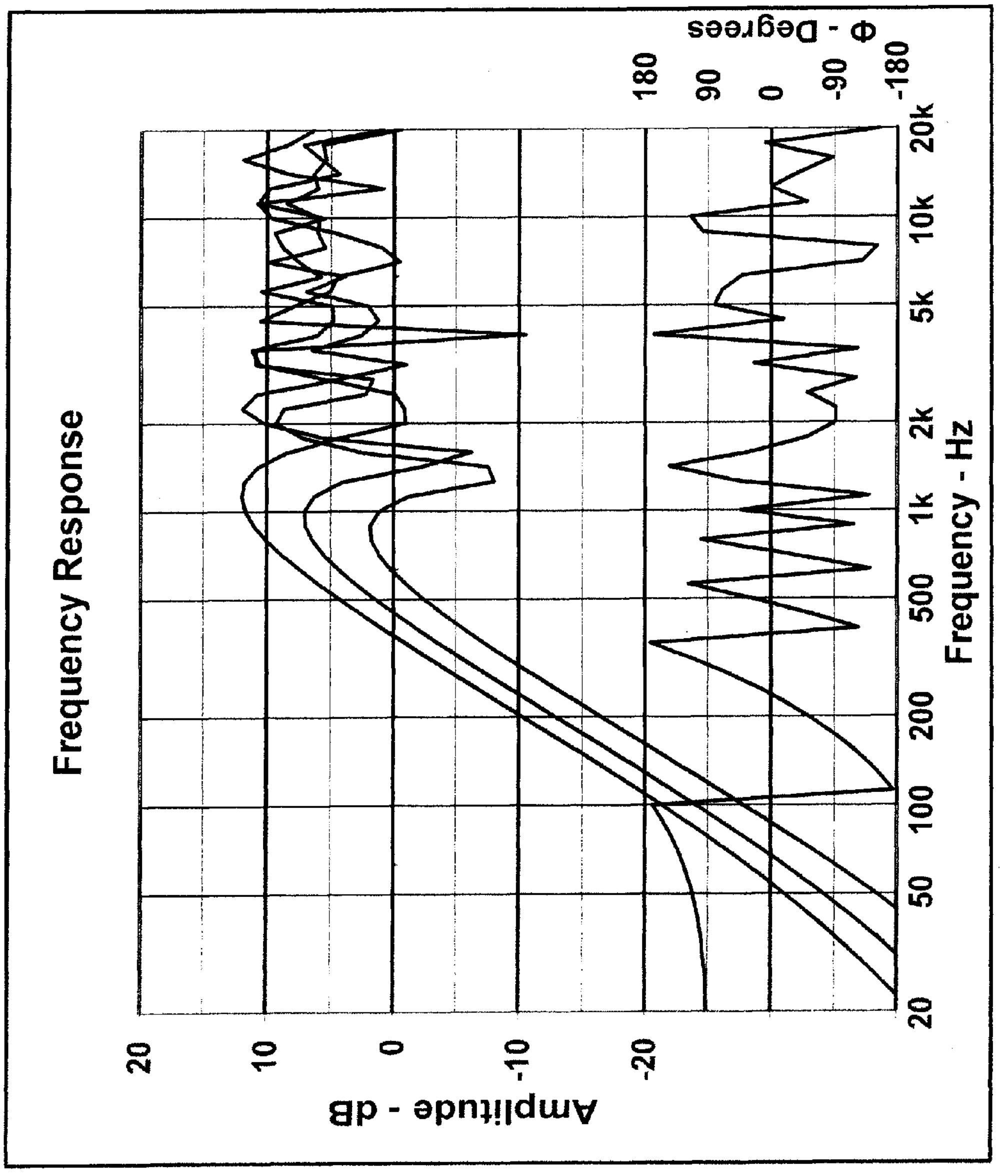
FIG. 23 illustrates frequency response for a system with 150 mm between microphones, according to certain embodiments.

In certain embodiments, the microphone array will consist of at least three microphones substantially equal-spaced in a line with a distance d between them. FIG. 22 illustrates the frequency response shown with a linear amplitude scale and a linear frequency scale the frequency response of an exemplary system where the distance is 150 mm between microphones. FIG. 23 illustrates in conventional form the frequency response of an exemplary system where the distance is 150 mm between microphones. The spacing d corresponds to a delay which can be calculated as (d/v) where v is the velocity of sound. The signals from the outer microphones are amplified and combined together. They are then passed through a delay system that delays the signal by a time (d/v). We call this result signal A. The signal from the centre microphone is amplified and split into two components. One component is delayed by a time (2d/v). The two components are then combined to form signal B. If an audio signal arrives from a direction on the axis of the at least three microphones, and we describe this signal as sin (ωt) at the first microphone where ω is angular frequency in radians per second and t is time, the following signals arise from the microphones:

Signal A may consist of a component from each of the microphones with a delay of (2d/v) arising from the fact that the signal arrives first at one microphone and then, after a delay (2d/v), at the other; this signal can be represented as (sin(ωt)+sin(ωt+2d/v)); the delay system further delays this signal by (d/v) to give, (sin(ω(t+d/v))+sin(ω(t+3d/v))); and Signal B consists of a signal arriving at the centre microphone (d/v) later than that arriving at the first microphone which can be represented as sin(ω(t+d/v)), combined with a copy of this signal which is delayed by (2d/v) as described for the centre microphone above sin(ω(t+3d/v)); and the combined signal is thus (sin(ω(t+d/v))+sin(ω(t+3d/v))).

Signals A and B are seen to be identical, or substantially identical. If they are now subtracted, the resultant signal from the axial direction is zero, or substantially zero, at all, or most of the desired, frequencies.

Next we look at the response of the microphone cell to signals at approximately right angles, or right angles, to the axis. Signals from this direction arrive simultaneously, or substantially simultaneously, at all of the at least three microphones. The signal at the microphones is again represented as sin(ωt). Signal A is now the sum of two identical components, or substantially identical components, one from each of the outer microphones. This represented as 2 sin(ωt). This is then delayed to produce 2 sin(ω(t+d/v)). Signal B is the sum of sin(ωt) and a delayed version sin(ω(t+2d/v)), giving: sin(ωt)+sin(ω(t+2d/v)). We now subtract Signal A from Signal B, giving:

$$
\begin{aligned}
&2\sin(\omega(t+d/v)) - (\sin(\omega t) + \sin(\omega(t+2d/v))) = \\
&\quad 2\sin(\omega(t+d/v)) - 2\sin(\omega(t+d/v))\cos(\omega d/v) = \\
&\quad\quad 2(1-\cos(\omega d/v))\sin(\omega(t+d/v)).
\end{aligned}
$$

The frequency response of the microphone cell is given by the amplitude of the signal 2(1−cos(ωd/v)). Examination of this response shows that it is zero, or substantially zero, at zero frequency and when (ωd/v) is a multiple of 2π and has a value 2 at π, 3π, etc. Now ω=2πf where f is frequency in cycles per second. When ωd/v=π, we have a maximum response of value 4. So 2πfd/v=π. Thus the frequency of maximum response, f, is given by f=v/2d. Now v=340.3 meters per second, so if d=170.15 mms then f=1000 Hz.

The shape of the response determined by the amplitude term 2(1−cos(ωd/v)) is such that at 500 Hz and 1500 Hz, the amplitude is half, or approximately half, the maximum.

$$
\begin{aligned}
\text{Signal } A &= \sin(\omega(t - d/v\sin\Theta + d/v)) + \sin(\omega(t + d/v\sin\Theta + d/v)) = \\
&\quad 2\sin(\omega(t+d/v)) \times \cos(\omega d/v\sin\Theta)
\end{aligned}
$$

$$
\text{Signal } B = \sin(\omega t) + \sin(\omega(t+2d/v)) = 2\sin(\omega(t+d/v)) \times \cos(\omega d/v)
$$

$$
\text{Signal } A - \text{Signal } B = 2\sin(\omega(t+d/v))(\cos(\omega d/v\sin\theta) - \cos(\omega d/v)).
$$

In certain embodiments, with appropriate filtering, a cell can be used over a frequency range of between 3 to 1 and 5 to 1 depending on the noise performance of the microphone insert used. Three to one involves of signal to noise loss of approximately 2 times or approximately 6 dB while 5 to 1 involves signal to noise loss of approximately 4 times or approximately 12 dB. Separate cells may be combined to provide the desired frequency coverage. In certain embodiments, with appropriate filtering, a cell can be used over a frequency range of between 300 Hz and 3 KHz, 300 Hz to 3.3 KHz, 200 Hz to 3 KHz, 300 Hz to 5 KHz, 200 Hz to 5 KHz, or 150 Hz to 6 KHz depending on the noise performance of the microphone insert used.

The examples disclosed herein have typically used analogue filtering means to achieve the broadband 90 degree phase shift required by some cases. It will be apparent to those of ordinary skill in the art that all these circuits may be replicated using a combination of A/D converters for each microphone elements and various well known digital processing means like digital filtering or convolution approaches or Fourier Transform approaches to achieve the same end. In certain situations, it may be beneficial to use a combination of analogue filtering approaches and digital approaches, for example, where the desired output signal is to be digital.

Figure 48:
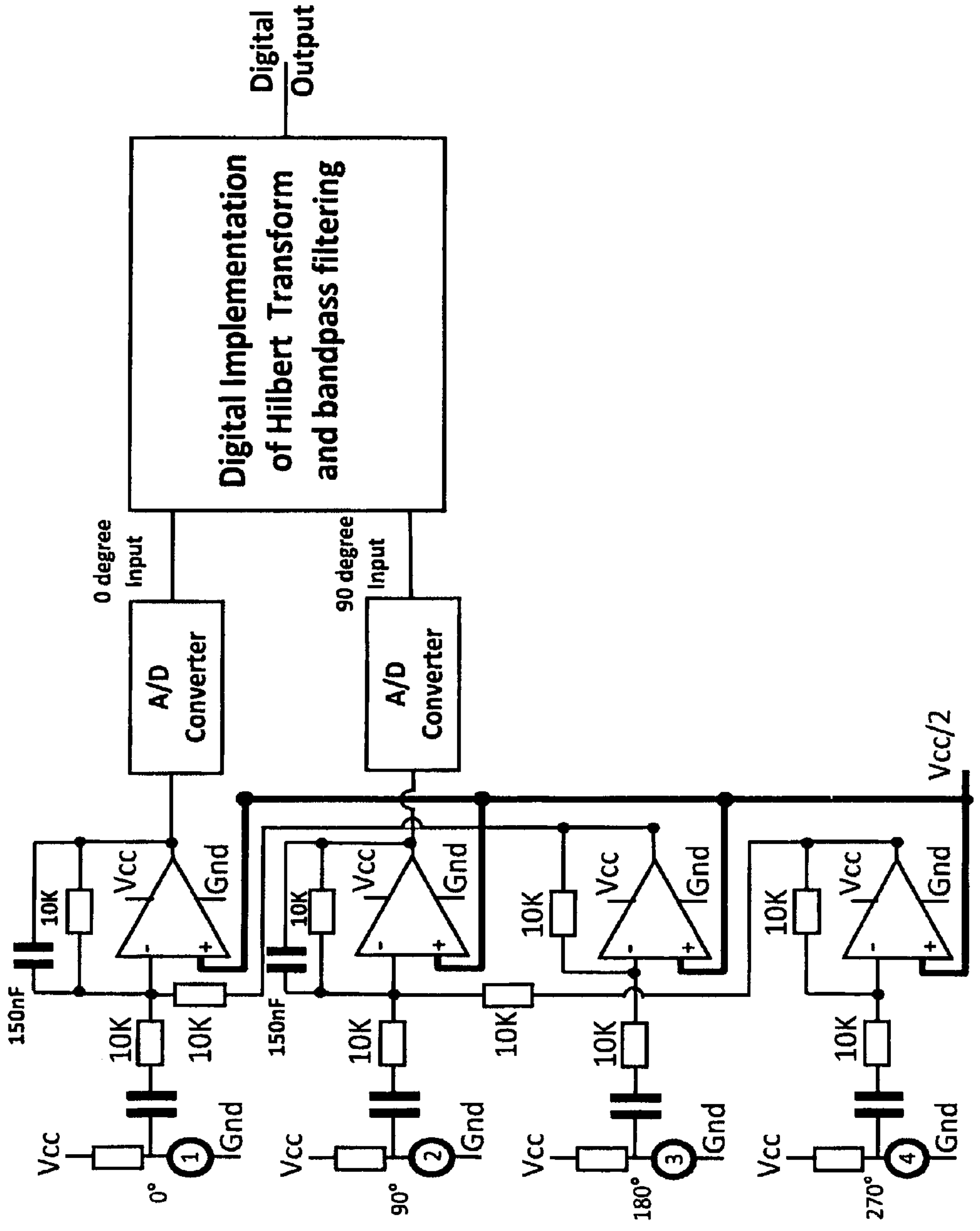
FIG. 48 illustrates a circuit according to certain embodiments.

It will be apparent to those of ordinary skill in the art that in those embodiments using Hilbert circuits, it may be advantageous to use analog means or approaches to combine the input signals for the 0 degree and 90 degree inputs as this may reduce the dynamic range requirements on the A/D converters (see, for example, FIG. 48). Similarly, in certain embodiments where the output signal is the difference between the sum of groups of microphone elements, it may be advantageous to digitize after combining signals by analogue means.

In certain applications, it may be useful to include commonly used signal processing means or approaches to cancel the signal received by the microphones from the loudspeaker and the various echoes emanating within the room. It will be apparent to those of ordinary skill in the art that digital means may be employed to satisfy the requirements such as those set out by the ITU in recommendation ITU-T G.168.

Figure 49:
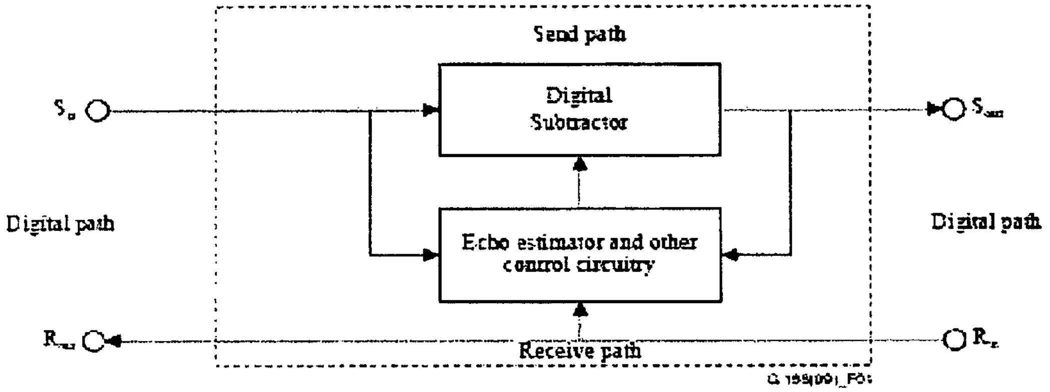
FIG. 49 illustrates an echo canceller according to certain embodiments.

Certain digital network echo cancellers may be voice operated devices placed in the 4-wire portion of a circuit (which may be an individual circuit path or a path carrying a multiplexed signal) and may be used for reducing the echo by subtracting an estimated echo from the circuit echo (see FIG. 49). Functionally, similar to a digital echo canceller (DEC) interfaces at 64 kbit/s. However, 24 or 30 digital echo cancellers, for example, may be combined corresponding to the primary digital hierarchy levels of 1544 kbit/s or 2048 kbit/s, respectively. This may be applicable to the design of echo cancellers using digital techniques, and intended for use in circuits where the delay exceeds the limits specified by ITU-T G.114 and ITU-T G.131. It may be desirable for echo control devices used on international connections to be compatible with each other. Echo cancellers designed to this recommendation may be compatible with each other, with echo cancellers designed in accordance with ITU-T G.165, and with echo suppressors designed in accordance with ITU-T G.164. In certain applications, compatibility may be defined as follows: 1) that a particular type of echo control device (say Type I) has been designed so that satisfactory performance may be achieved when practical connections are equipped with a pair of such devices; and 2) that another particular type of echo control device (say Type II) has been likewise designed. Then the Type II may be said to be compatible with Type I, if it is possible to replace an echo control device of one type with one of the other type, without degrading the performance of the connection to an unsatisfactory level. In this sense, compatibility does not imply that the same test apparatus or methods can necessarily be used to test both Type I and Type II echo control devices.

Variation may be permitted in design details not covered by the requirements. This recommendation is for the design of digital echo cancellers and defines tests that ensure that echo canceller performance is adequate under wider network conditions than specified in ITU-T G.165, such as performance on voice, fax, residual acoustic echo signals and/or mobile networks.

Figure 50:
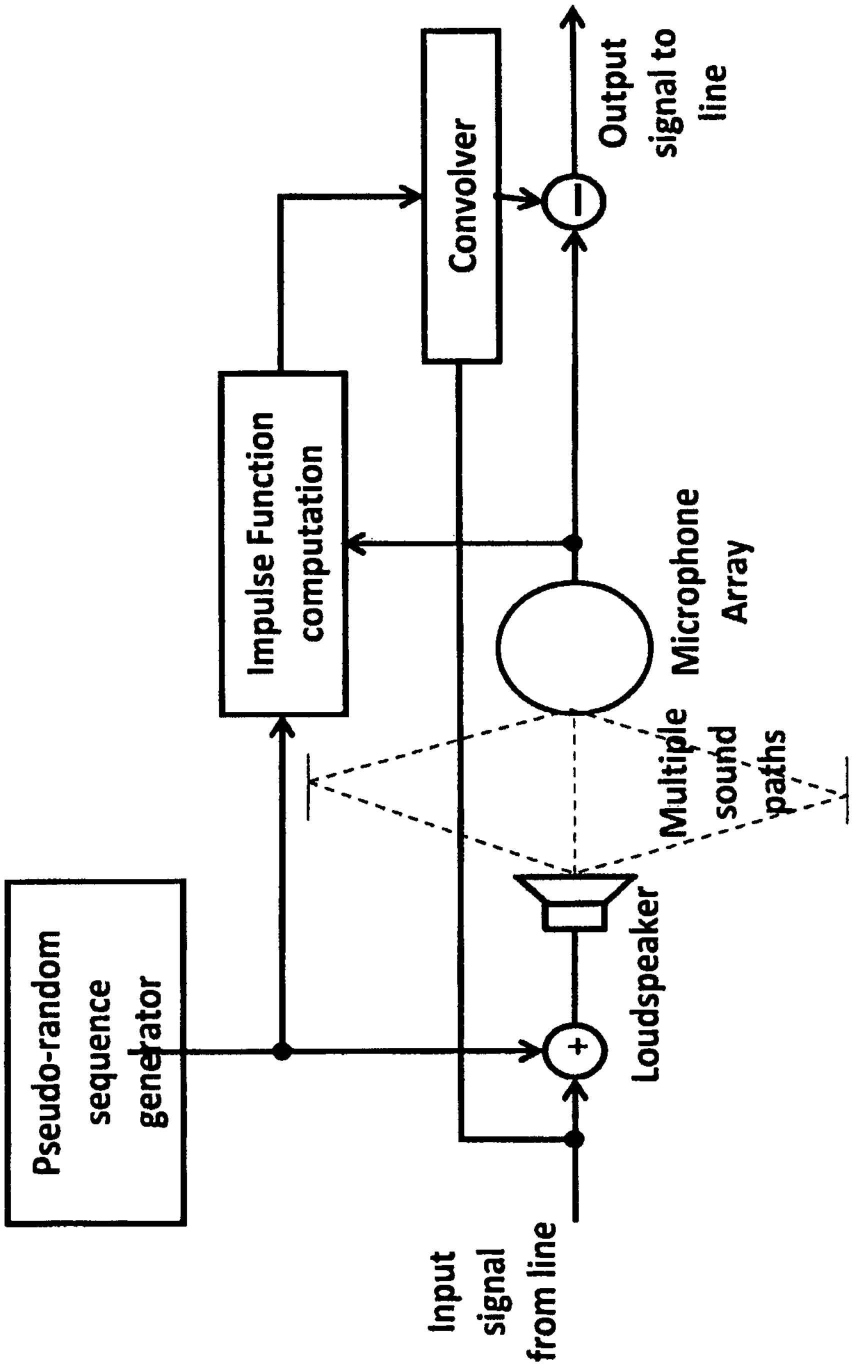
FIG. 50 illustrates an approach to cancelling speaker signal and echo in a microphone array, according to certain embodiments.

It will be apparent to those of ordinary skill in the art that the impulse response of the speaker microphone system may be determined by means or approaches such as injecting a pseudo-random sequence at the loudspeaker and computing the correlation function of this with output signal from the microphone. This impulse response, which may typically be 100-200 msecs in length, may now be convolved with the loudspeaker input signal and the result subtracted from the microphone output signal, thus cancelling the echoes. See, for example, FIG. 50. Such a system in certain applications may be used stand alone for calibration or used in conjunction with other processing related to ITU-T G.168.

In certain applications, it will be useful to include commonly used signal processing means to cancel the signal received by one speakerphone system from another. Where half duplex systems are used, such cancellation means may be omitted but for full duplex it will be desirable to provide some suppression of the signal from other speakerphones. Means may be provided to hold an existing state of the direction finding system or prevent changes in the presence of a signal above a determined threshold from the speaker of the speakerphone.

Figure 12:
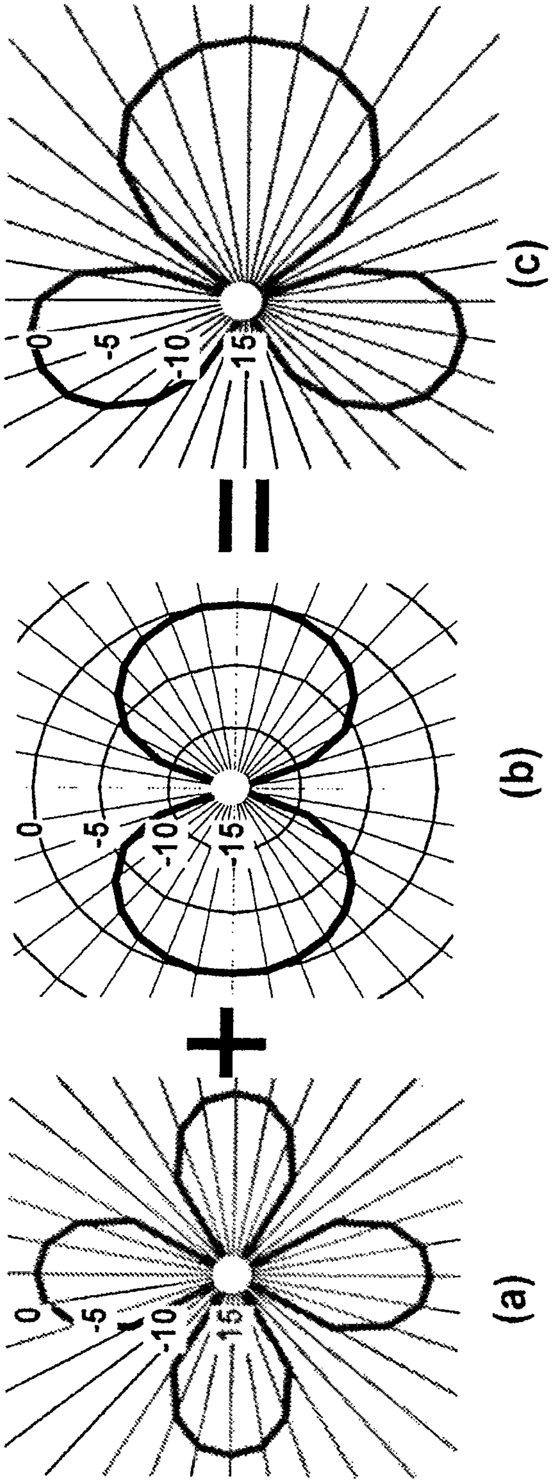
FIG. 12 illustrates the effect of combining certain embodiments with other embodiments to provide a steerable beam.

In certain embodiments, combinations of certain microphone array configurations provide steerable directional characteristics. For example, as illustrated in FIG. 12, embodiments of the types shown in FIG. 9(*a*) and embodiments of the types shown in FIG. 7(*a*) may be combined in appropriate proportions to provide a steerable beam array. A combination of 0.4 times the response of FIG. 9(*a*) and 0.6 times the response of FIG. 7(*a*) gives a response with two lobes at approx −6 dB. The beam is steerable following the principles outlined and in FIG. 10 and FIG. 8 and the related discussion herein. Microphone arrays of the configuration illustrated in FIG. 12 may provide a substantial reduction in unwanted sound. In certain embodiments, the reduction in unwanted sound will be greater then 5%, 10%, 20%, 25%, 30%, 40%, 50%, 60%, or 70%. In certain embodiments, the reduction in unwanted sound will be about 5%, 10%, 20%, 25%, 30%, 35%, 40%, 45%, 50%, 55%, 60%, or 70%. The microphone array system illustrated in FIG. 12 has the cancellation properties in relation to the loudspeaker signal.

Figure 13:
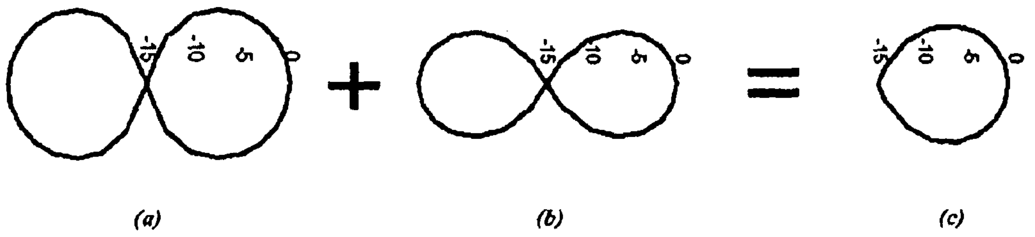
FIG. 13 illustrates the effect of combining certain embodiments with other embodiments to provide a steerable beam.

Another example is illustrated in FIG. 13. Embodiments of the types shown in FIG. 7(*a*) and FIG. 11(*a*) are combined to give a wider beam than the previous case but negligible side lobes. For the embodiments illustrated in FIG. 13(*a*), the beam is steerable using the principles outlined in FIG. 8. For the embodiments illustrated in FIG. 13(*b*) and disclosed herein, the microphone elements are arranged at approximately 45° intervals and will provide increments of 45°. Proportions of adjacent pairs, e.g. 0°/180° and 45°/225° can be mixed to provide various angles from 0° to 45°.

The microphone arrays disclosed herein can be used in a number of different applications. For example, certain configurations may be used for speaker phone systems that can be used in conference room settings, or to provide superior cell phone conferencing capability.

Figure 24A:
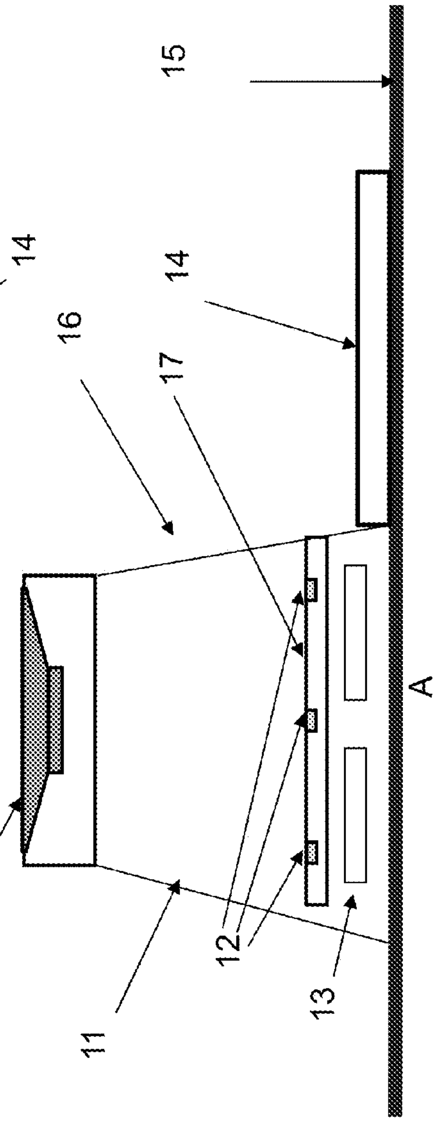
FIGS. 24(*a*) and (*b*) illustrate a schematic for speakerphone device in side view and top view in accordance with certain embodiments.
Figure 24B:
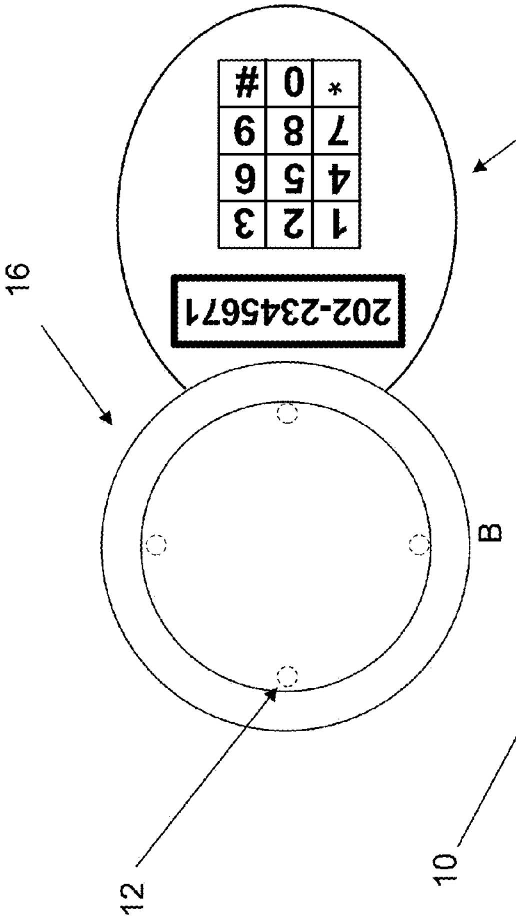

A speaker phone device 16 is illustrated in FIG. 24 in accordance with certain embodiments. FIG. 24 illustrates microphone elements 12 that are evenly spaced, or substantially evenly spaced, around a circle. That circle defines a vertical axis away from the plane that the microphone elements are situation on and is concentric, or substantially concentric, with the loudspeaker axis and the mounting structure for both the loudspeaker and the microphones. Thus the path length for sound signals coming from a point on the vertical axis to each of the microphone elements is equal, or substantially equal. The path lengths differ for sound sources of that vertical axis. The phasing of the microphone elements is such that signals arriving from a source with equal path lengths are cancelled, or substantially cancelled. FIG. 24(*a*) show the device in side view and FIG. 24(*b*) shows the device in top view. This speaker phone has an up-firing loudspeaker 10 locate above the four microphones 12. The speaker phones loudspeaker 10 is disposed in the housing 11 to radiate sound in a generally upward and/or outward direction relative to a surface 15 against or upon which the speaker phone is disposed in a generally horizontal, upward-facing surface, in the case of a desktop-mounting speakerphone. However, it is to be understood that these speaker phones may mounted or placed on a table, wall or other useful surfaces or orientations depending on the particular application. The microphone elements 12 are equally spaced, or substantially equally spaced, on a circle of about 60 mm in diameter within an acoustically transparent support structure 11. The microphones 12 are typically distributed around the periphery of the speaker phone to receive, speech or other sounds uttered by one or more participants situated in front of or circumferentially around the phone and engaged in a teleconference with one or more far-end conversationalists. The microphones are ideally ones having a wide dynamic range so that the loudspeaker signals received by the microphones are not unduly distorted before the cancellation circuits. The microphones 12 are ideally spaced away from the output of the speaker 10 by a distance D, typically not less than about 12.5-15.0 cm but may be less if the dynamic range of the microphones will allow it. In certain aspects the microphones will be spaced as far away from the output of the speaker 10 as is practical to minimize the amount of sound coupled from the speaker to the microphones during operation, i.e., resulting in acoustic echo that may not be cancelled in the combined signal and minimize the dynamic range requirements for the microphones. In this embodiment the microphone elements are shown to be mounted in a support structure 17. However, how the microphone elements are mounted in the speaker phone may vary. It is to be understood that the number of microphone elements may vary from 4 to 16 or even more if desired. Furthermore, in general terms the greater the number of microphone elements the better the signal to noise ration will be for the device. Also shown in schematic form in FIG. 24(*a*) are the circuit, battery, Wi-Fi, and/or bluetooth components 13. Not shown in FIG. 24, the speakerphone may also be hard wired for plugging into a wall type outlet or other electrical connection in order to power the device. FIG. 24 does not show the wiring between the sections, however, the wiring of such a device is within the skill of those in the speaker phone art. Also illustrated is a multi-button set 14 of manually actuated dialing and signaling switches, and a liquid crystal alphanumeric display.

Figures 25A, 25B:
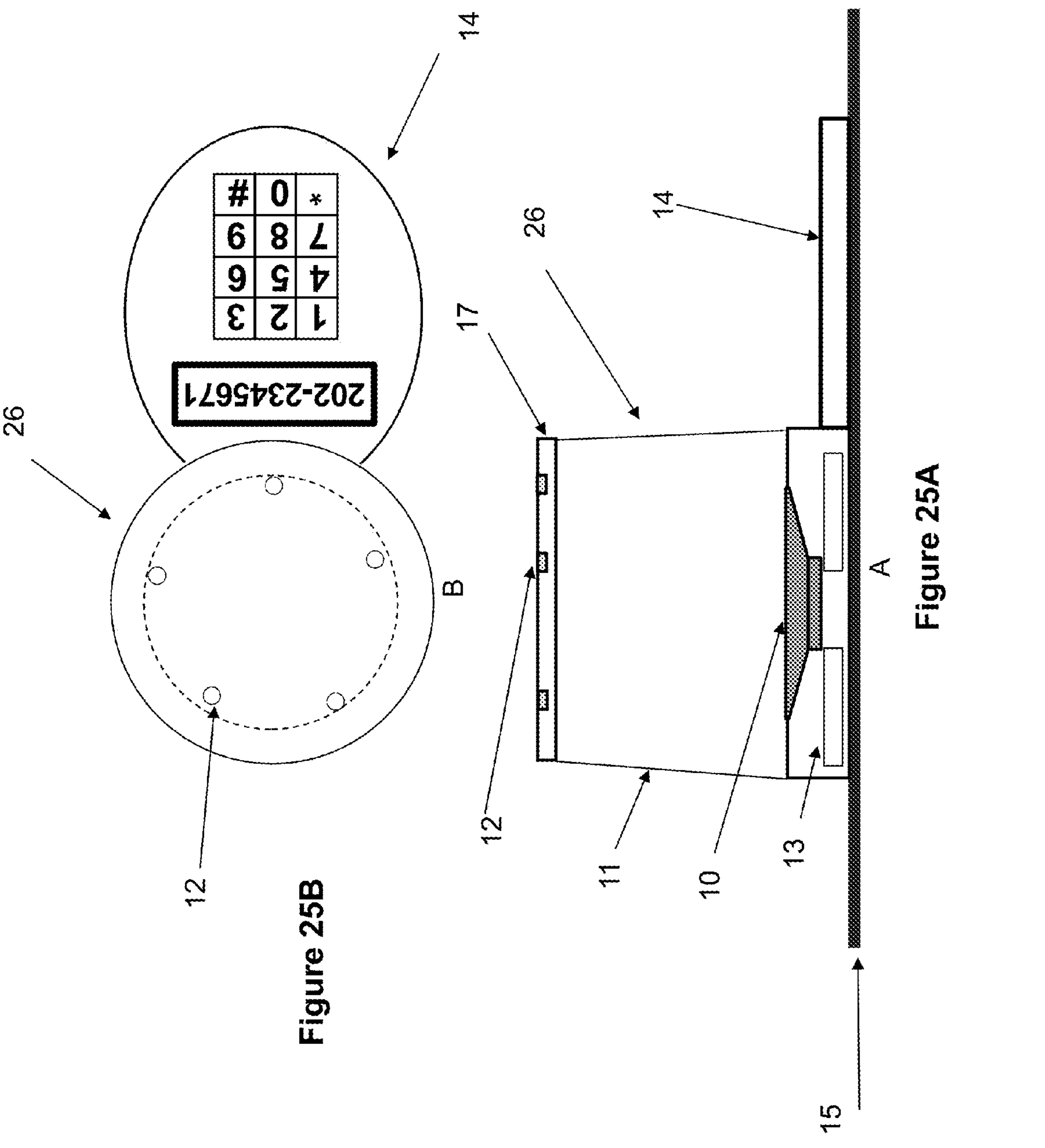
FIGS. 25(*a*) and (*b*) illustrate a schematic for speakerphone device in side view and top view in accordance with certain embodiments.

FIG. 25 illustrates another device 26 in accordance with certain embodiments. FIG. 25 illustrates five microphone elements 12 that are evenly, or substantially evenly, spaced around a circle. That circle defines a vertical axis away from the plane that the microphone elements are situation on and is concentric, or substantially concentric, with the loudspeaker axis and the mounting structure for both the loudspeaker and the microphones. Thus the path length for sound signals coming from a point on the vertical axis to each of the microphone elements is equal, or substantially equal. The path lengths differ for sound sources of that vertical axis. The phasing of the microphone elements is such that signals arriving from a source with equal path lengths are cancelled, or substantially cancelled. FIG. 25(*a*) show the device in side view and FIG. 25(*b*) shows the device in top view. This device has an up-firing loudspeaker 10 locate below the five microphones 12. The loudspeaker 10 is disposed in the housing 11 that is sufficiently acoustically transparent to radiate sound in a generally upward and/or outward direction relative to a surface 15 against or upon which the device is disposed in a generally horizontal, upward-facing surface, in the case of a desktop-mounting device. The microphone elements 12 are equally spaced, or substantially equally spaced, on a circle of about 60 mm in diameter within an acoustically transparent support structure 11. The microphones 12 are typically distributed around the periphery of the device to receive, speech or other sounds uttered by one or more participants situated in front of or circumferentially around the phone and engaged in a teleconference with one or more far-end conversationalists. The microphones are ideally ones having a wide dynamic range so that the loudspeaker signals received by the microphones are not unduly distorted before the cancellation circuits. The microphones 12 are typically spaced away from the output of the speaker 10 by a distance D, typically not less than about 10.0-15.0 cm. In certain aspects, the microphones are spaced as far away from the output of the speaker 10 as is practical to minimize the amount of sound coupled from the speaker to the microphones that must be cancelled during operation, i.e., acoustic echo. In this embodiment the microphone elements are shown to be mounted in a support structure 17 that is situation at the upper end of the support structure 11. Also shown in schematic form in FIG. 25(*a*) are the circuit, battery, Wi-Fi, and/or bluetooth components 13. Not shown in FIG. 25 the speakerphone may also be hard wired for plugging into a wall type outlet or other electrical connection in order to power the device. FIG. 25 does not show the wiring between the sections, however, the wiring of such a device is within the skill of those in the speaker phone art. Also shown illustrated is a multi-button set 14 of manually actuated dialing and signaling switches, and a liquid crystal alphanumeric display.

FIG. 26 illustrates another speakerphone device 35 in accordance with certain embodiments. FIG. 26 illustrates four microphone elements 12 that are evenly spaced around a circumference. That circumference defines a vertical axis away from the plane that the microphone elements are situation on and is concentric, or substantially concentric, with the loudspeaker axis and the mounting structure 11, 17 for both the loudspeaker and the microphones. Thus the path length for sound signals coming from a point on the vertical axis to each of the microphone elements is equal, or substantially equal. The path lengths differ for sound sources of that vertical axis. The phasing of the microphone elements is such that signals arriving from a source with equal path lengths are cancelled, or substantially cancelled. FIG. 26(*a*) show the device in side view and FIG. 26(*b*) shows the device in top view. This speakerphone has an up-firing loudspeaker 10 locate below the four microphones 12. The loudspeaker 10 is disposed in the housing 11 that is sufficiently acoustically transparent to radiate sound in a generally upward and/or outward direction relative to a surface 15 against or upon which the speakerphone is disposed in a generally horizontal, upward-facing surface, in the case of a desktop-mounting speakerphone. As can be seen in FIG. 26(*b*), the upper surface of the device has circular holes 30 in the baffle to allow the sound to flow from the loudspeaker. These holes in the baffle provide an alternate equal, or substantially equal pathway from the loudspeaker to each of the microphone elements. The microphones are ideally ones having a wide dynamic range so that the loudspeaker signals received by the microphones are not unduly distorted before the cancellation circuits. The microphone elements 12 are equally spaced, or substantially equally spaced, on a circle of about 60 mm in diameter within an acoustically transparent support structure 11. The microphones 12 are typically spaced away from the output of the speaker 10 by a distance D, typically not less than about 2 cm, that is as far away from the output of the speaker 10 as is practical to minimize the amount of sound coupled from the speaker to the microphones that must be cancelled during operation, i.e., acoustic echo. In this embodiment the microphone elements are shown to be mounted in a support structure 17 that is situation at the upper end of the support structure 11.

Figure 44B:
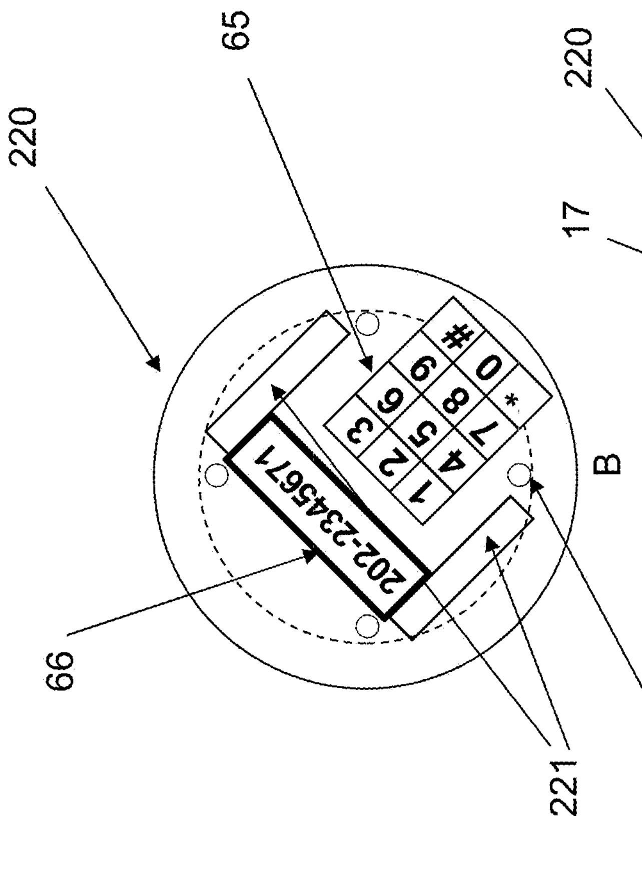
FIGS. 44(*a*) and (*b*) illustrate a schematic for speakerphone device in side view and top view in accordance with certain embodiments.
Figure 44A:
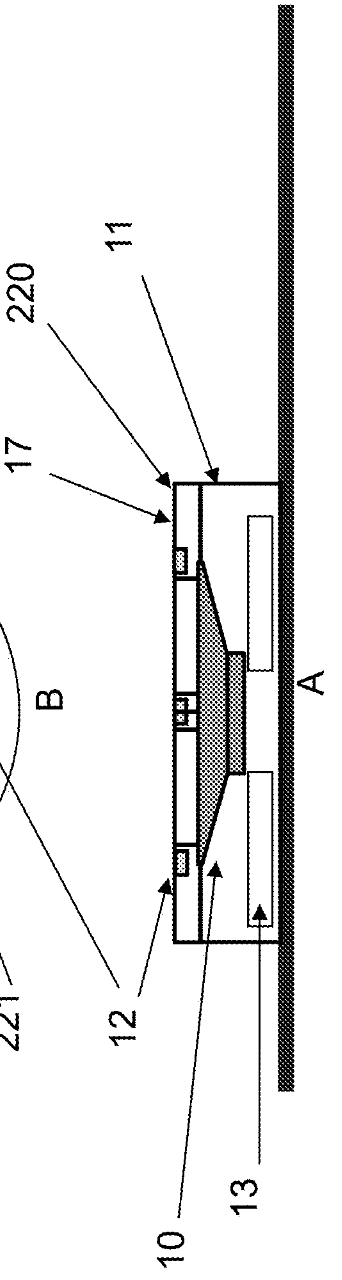

FIGS. 44(*a*) and (*b*), illustrates another speakerphone device 220 in accordance with certain embodiments. FIG. 44 is similar to the device illustrated in FIG. 26. Except, as can be seen in FIG. 44(*b*), the upper surface of the device has rectangular slots 221 or holes in the baffle to allow the sound to flow from the loudspeaker. These holes in the baffle provide an alternate equal, or substantially equal pathway from the loudspeaker to each of the microphone elements. Also in this embodiment a multi-button set 65 of manually actuated dialing and signaling switches, and a liquid crystal alphanumeric display 66 are mounted on the upper surface of the device above the microphone.

Figures 27A, 27B:
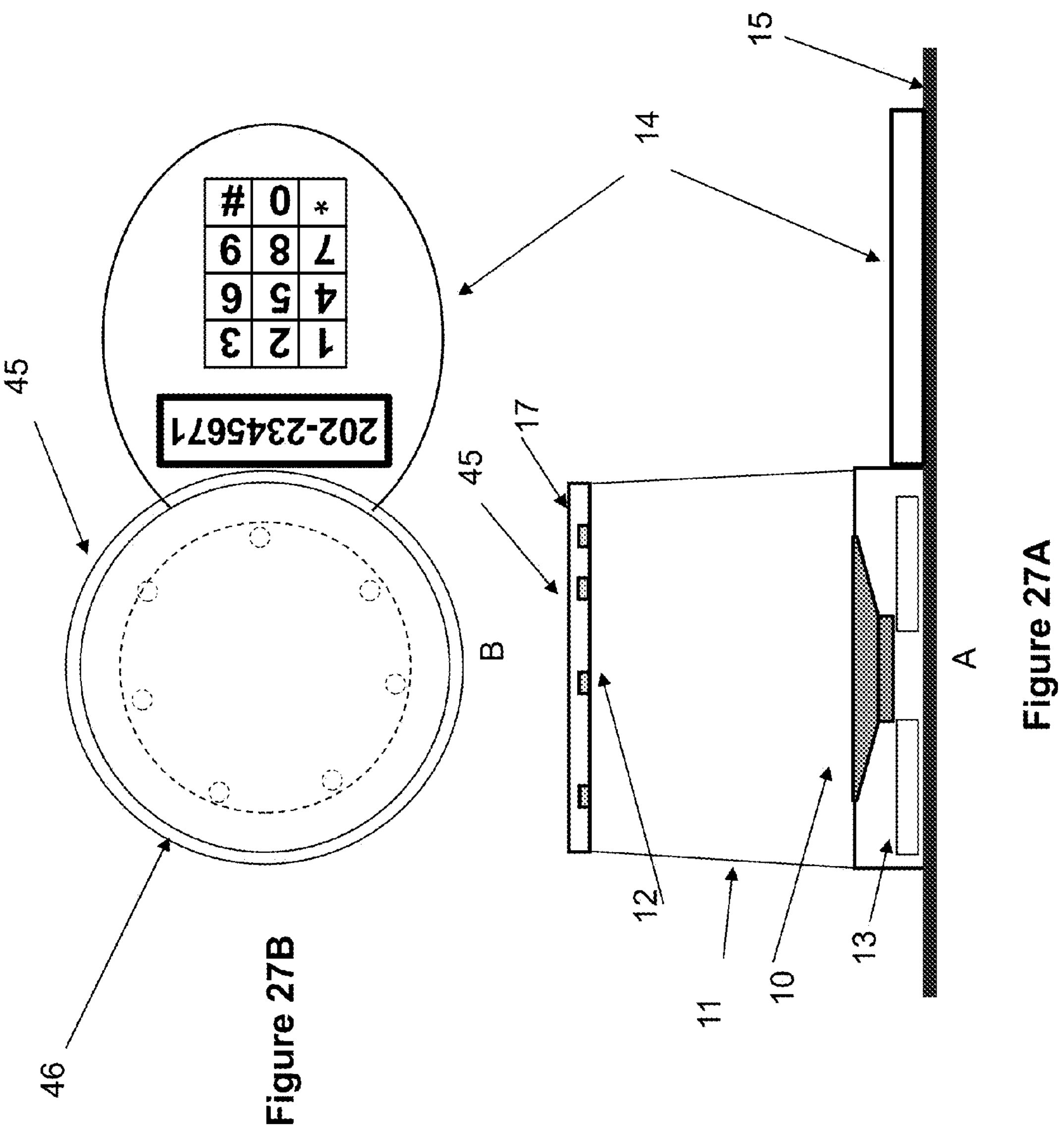
FIGS. 27(*a*) and (*b*) illustrate a schematic for speakerphone device in side view and top view in accordance with certain embodiments.

FIG. 27 illustrates another speakerphone device 45 in accordance with certain embodiments. FIG. 27 illustrates seven microphone elements 12 that are evenly, or substantially evening, spaced around a circle. That circle defines a vertical axis away from the plane that the microphone elements are situation on and is concentric, or substantially concentric, with the loudspeaker axis and the mounting structure for both the loudspeaker and the microphones. Thus the path length for sound signals coming from a point on the vertical axis to each of the microphone elements is equal, or substantially equal. The path lengths differ for sound sources of that vertical axis. The phasing of the microphone elements is such that signals arriving from a source with equal path lengths, or substantially equal path lengths are cancelled, or substantially cancelled. FIG. 27(*a*) shows the device in side view and FIG. 27(*b*) shows the device in top view. This speakerphone has an up-firing loudspeaker 10 locate below the five microphones 12. The speakerphones loudspeaker 10 is disposed in the housing 11 that is sufficiently acoustically transparent to radiate sound in a generally upward and/or outward direction relative to a surface 15 against or upon which the speaker phone is disposed in a generally horizontal, upward-facing surface, in the case of a desktop-mounting speakerphone. The microphones are ideally ones having a wide dynamic range so that the loudspeaker signals received by the microphones are not unduly distorted before the cancellation circuits. The microphone elements 12 are equally spaced, or substantially equally spaced, on a circle of about 60 mm in diameter within an acoustically transparent support structure 11. The microphones 12 are typically distributed around the periphery of the speaker phone to receive, speech or other sounds uttered by one or more participants situated in front of or circumferentially around the phone and engaged in a teleconference with one or more far-end conversationalists. The microphones 12 are typically spaced away from the output of the speaker 10 by a distance D, typically not less than about 10-15.0 cm that is as far away from the output of the speaker 10 as is practical to minimize the amount of sound coupled from the speaker to the microphones that must be cancelled during operation, i.e., acoustic echo. In this embodiment the microphone elements are shown to be mounted in a support structure 17 that is situation at the upper end of the support structure 11.

Figures 28A, 28B:
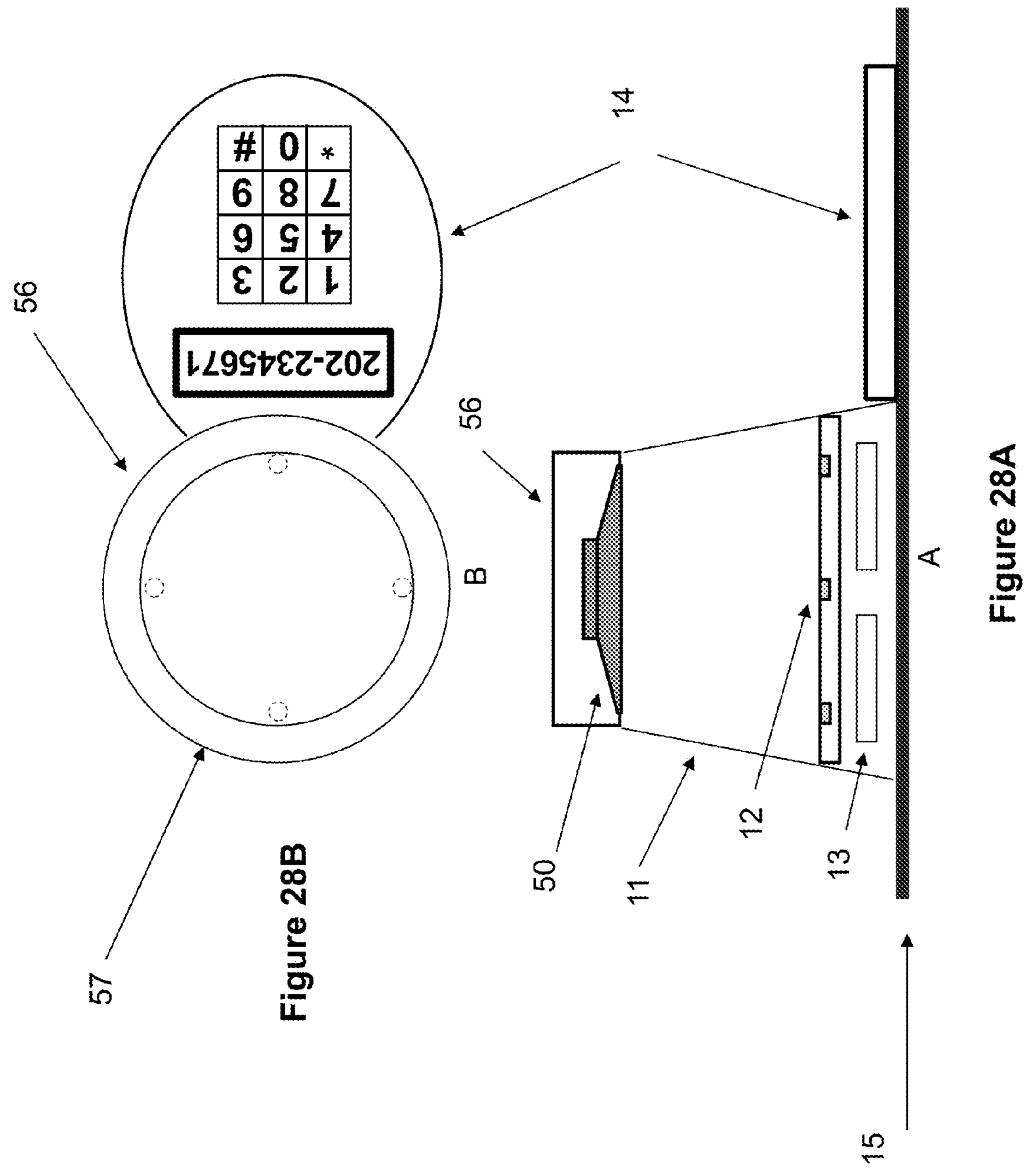
FIGS. 28(*a*) and (*b*) illustrate a schematic for speakerphone device in side view and top view in accordance with certain embodiments.

A speakerphone device 56 is illustrated in FIG. 28, in accordance with certain embodiments. FIG. 28 illustrates microphone elements 12 that are evenly spaced around a concentric, or substantially concentric, configuration. The phasing of the microphone elements is such that signals arriving from a source with equal path lengths are cancelled, or substantially cancelled. FIG. 28(*a*) shows the device in side view and FIG. 28(*b*) shows the device in top view with the circumference 57 of the device being illustrated. This speakerphone has an down-firing loudspeaker 50 locate above the four microphones 12. Otherwise this embodiment is similar to that shown in FIG. 24. The microphone elements 12 are equally spaced, or substantially equally spaced, on a circle of about 60 mm in diameter within an acoustically transparent support structure 11.

Figures 29A, 29B:
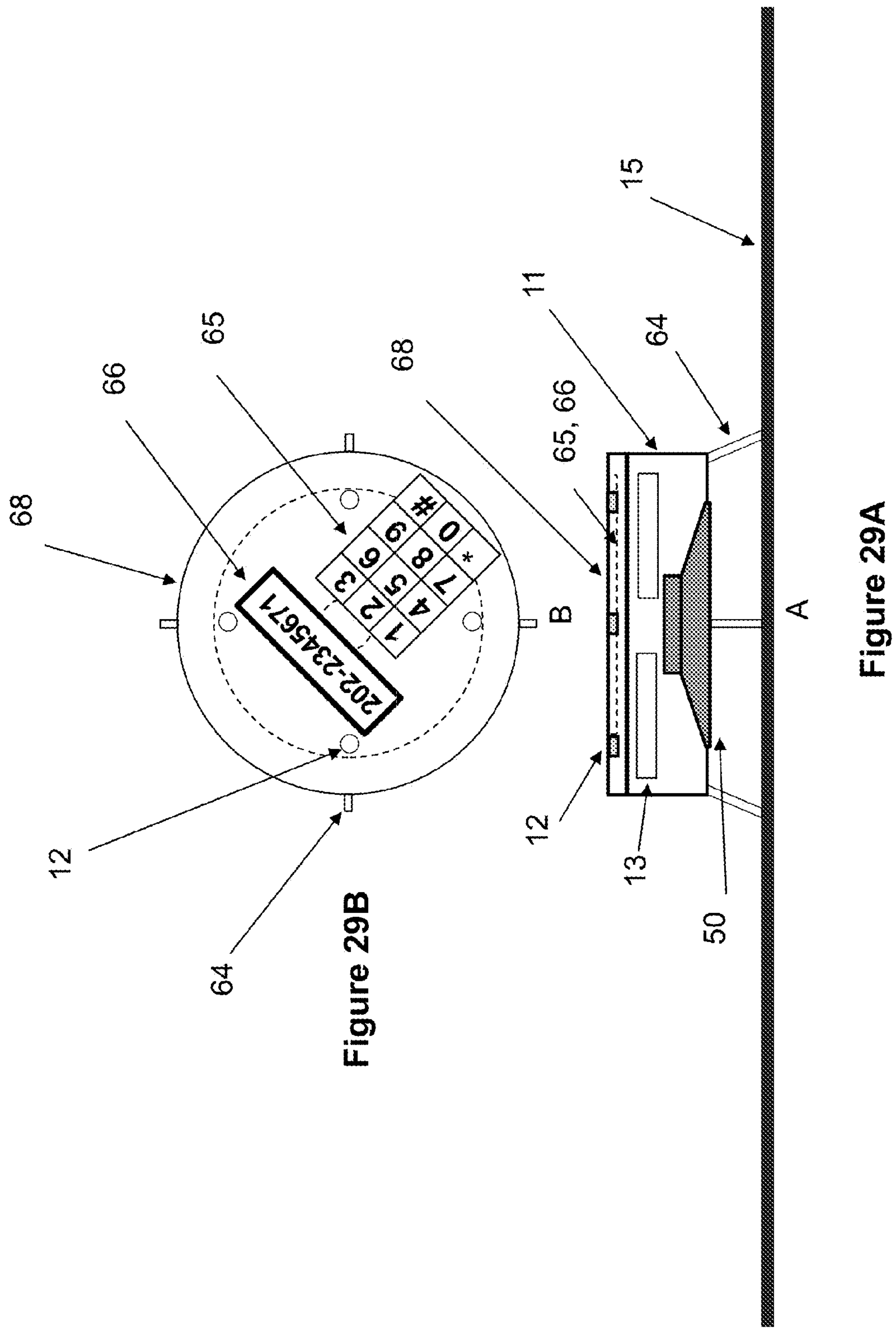
FIGS. 29(*a*) and (*b*) illustrate a schematic for speakerphone device in side view and top view in accordance with certain embodiments.

FIG. 29 illustrates another speakerphone device 68 in accordance with certain embodiments. FIG. 26 illustrates four microphone elements 12 that are evenly spaced around a circumference. Here the microphones 12 are located above the down firing speaker 50. FIG. 29(*a*) show the device in side view and FIG. 29(*b*) shows the device in top view. Here the loudspeaker 50 is disposed in the housing 11 that is sufficiently acoustically transparent to radiate sound. In addition, the device is support by four legs 64 above the surface 15. Also in this embodiment a multi-button set 65 of manually actuated dialing and signaling switches, and a liquid crystal alphanumeric display 66 are mounted on the upper surface of the device above the microphone.

Figure 30:
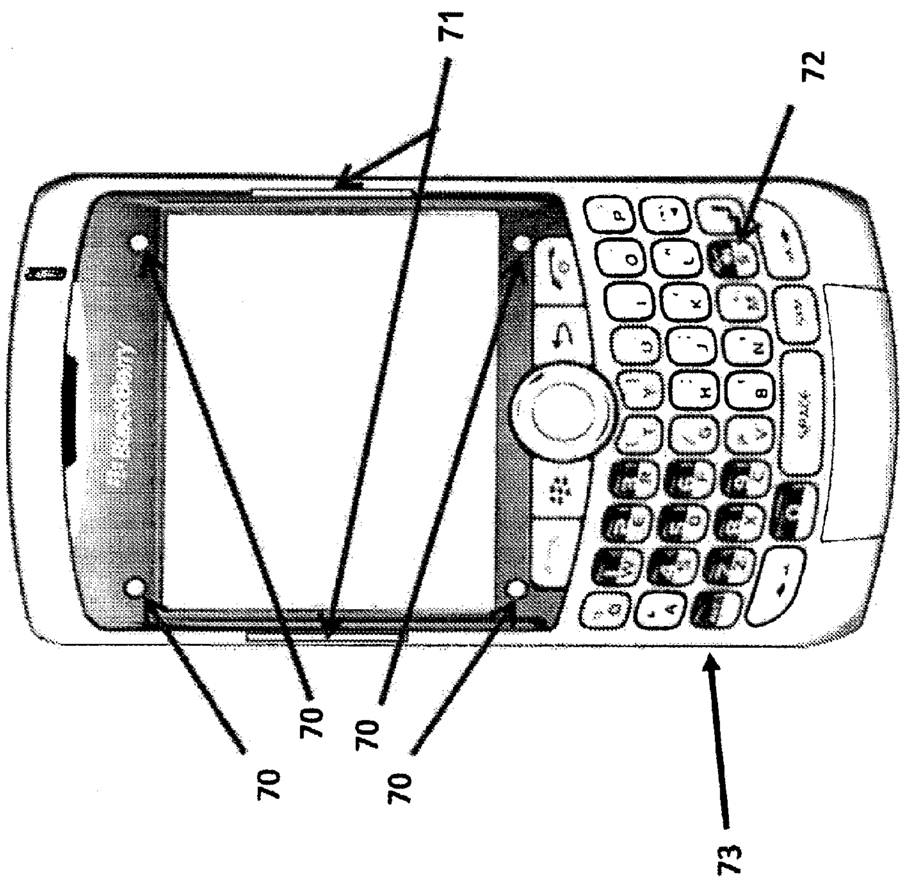
FIG. 30 illustrates a speakerphone located within a handset device in accordance with certain embodiments.

FIG. 30 illustrates another speakerphone device incorporated in to a mobile phone 73. The four microphone elements 70 are place equal distance, or substantially equal distance around a 60 mm circumference. Slots or rectangular openings 71 are provided to allow sound to travel from the speaker not shown and located within the phone. A key 72 is provided to actuated the speakerphone mode. Although this could also being carried out from the device interface without a key actuator.

Figures 31A, 31B:
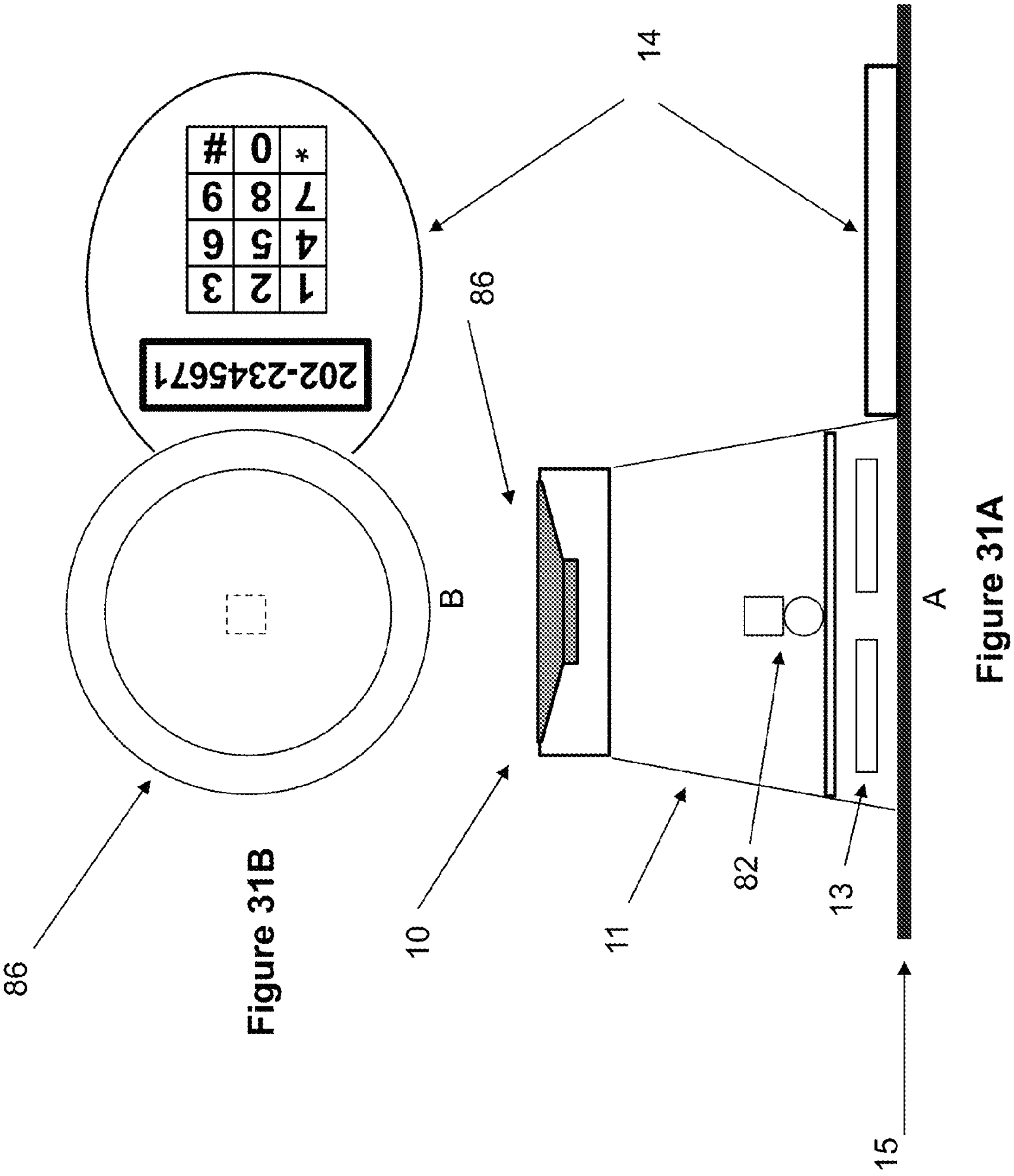
FIGS. 31(*a*) and (*b*) illustrate a schematic for speakerphone device in side view and top view in accordance with certain embodiments.

A speakerphone device 86 is illustrated in FIG. 31 in accordance with certain embodiments. FIG. 31 illustrates crossed bi-directional microphone elements 82 that are place in the center of or substantial close to the center of the circumference the structure. This circle defines a vertical axis away from the plane that the microphone elements are situation on and is concentric, or substantially concentric, with the loudspeaker axis and the mounting structure for both the loudspeaker and the microphones. Thus the path length for sound signals coming from a point on the vertical axis to each of the microphone elements is equal, or substantially equal. The path lengths differ for sound sources of that vertical axis. The phasing of the crossed bi-directional microphone elements is such that signals arriving from a source with equal path lengths are cancelled, or substantially cancelled. FIG. 31(*a*) show the device in side view and FIG. 31(*b*) shows the device in top view. This speakerphone has an up-firing loudspeaker 10 locate above the microphones elements 82. The loudspeaker 10 is disposed at the upper end of the housing 11 to radiate sound in a generally upward and/or outward direction relative to a surface 15. In this configuration, the microphone elements 82 are stacked on top of each. The microphones elements 82 are spaced away from the output of the speaker 10 by a distance D, typically not less than about 5-15.0 cm that is as far away from the output of the speaker 10 as is practical to minimize the amount of sound coupled from the speaker to the microphones that must be cancelled during operation, i.e., acoustic echo. In this embodiment the microphone elements are shown to be mounted near the lower end of the support structure.

FIG. 32 shows another variation of the arrangement using crossed bi-directional microphone elements in accordance with certain embodiments. Here the device 96 is illustrated with crossed bi-directional microphone elements 82 that are place in the centered of, or substantial close to the center of, the circumference the structure. Here the microphone elements are place in the upper portion of the device and are covered by a dome 97 that is sufficiently acoustically transparent. Here a dome is used to shield the microphones but any acceptable covering may be used or not used depending on the particular application. The phasing of the crossed bi-directional microphone elements is such that signals arriving from a source with equal path lengths are cancelled, or substantially cancelled. FIG. 32(*a*) show the device in side view and FIG. 32(*b*) shows the device in top view. Here the up-firing loudspeaker 10 is located in the lower portion of the device.

Figures 33A, 33B:
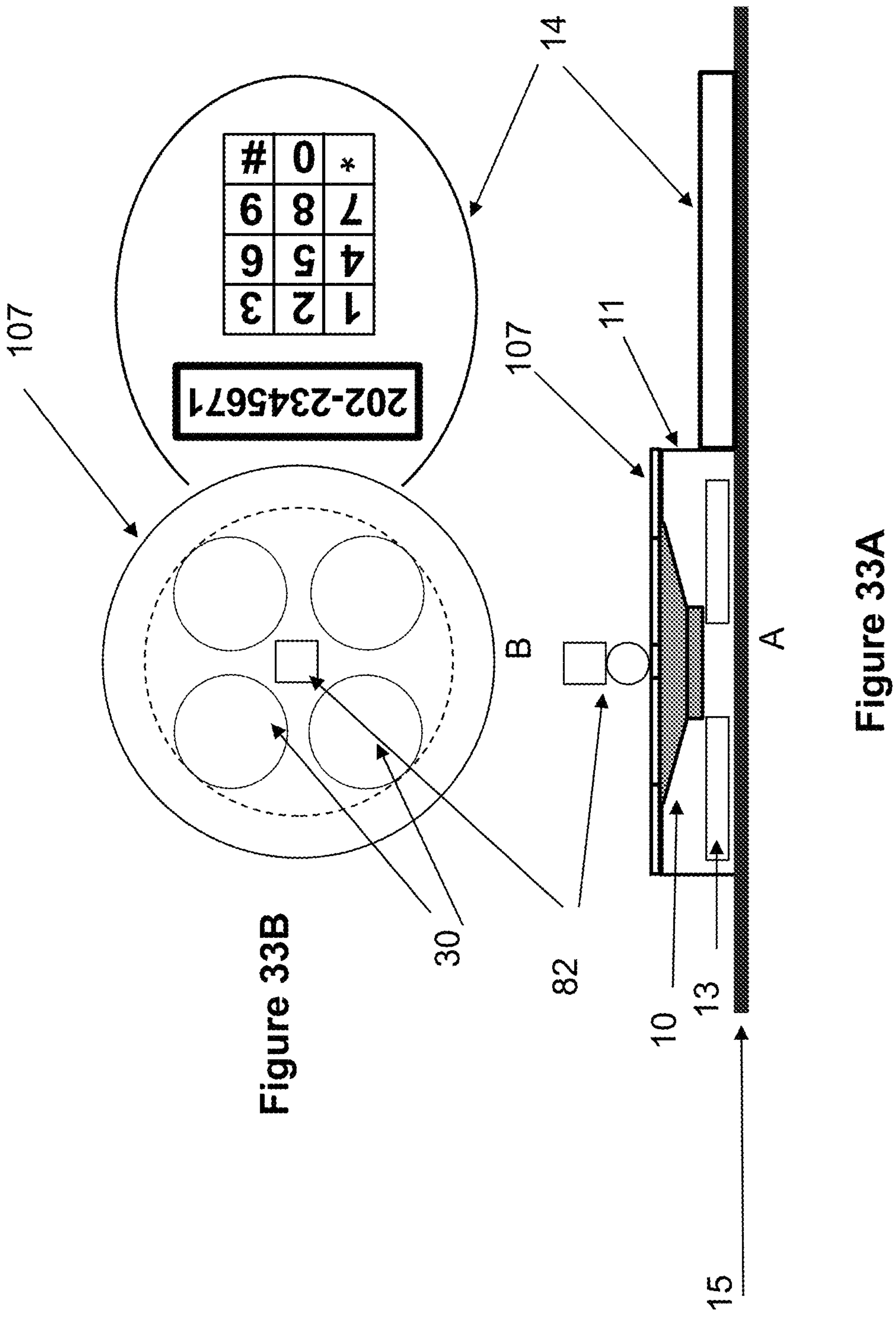
FIGS. 33(*a*) and (*b*) illustrate a schematic for speakerphone device in side view and top view in accordance with certain embodiments.

FIG. 33 shows another variation of the configuration of the speakerphone device 107 using bi-directional microphone elements in accordance with certain embodiments. Here the microphone elements 82 are stack near to and above the speaker 10. Holes 30 in the baffle are used to direct the sound from the up-firing loudspeaker.

Figures 34A, 34B:
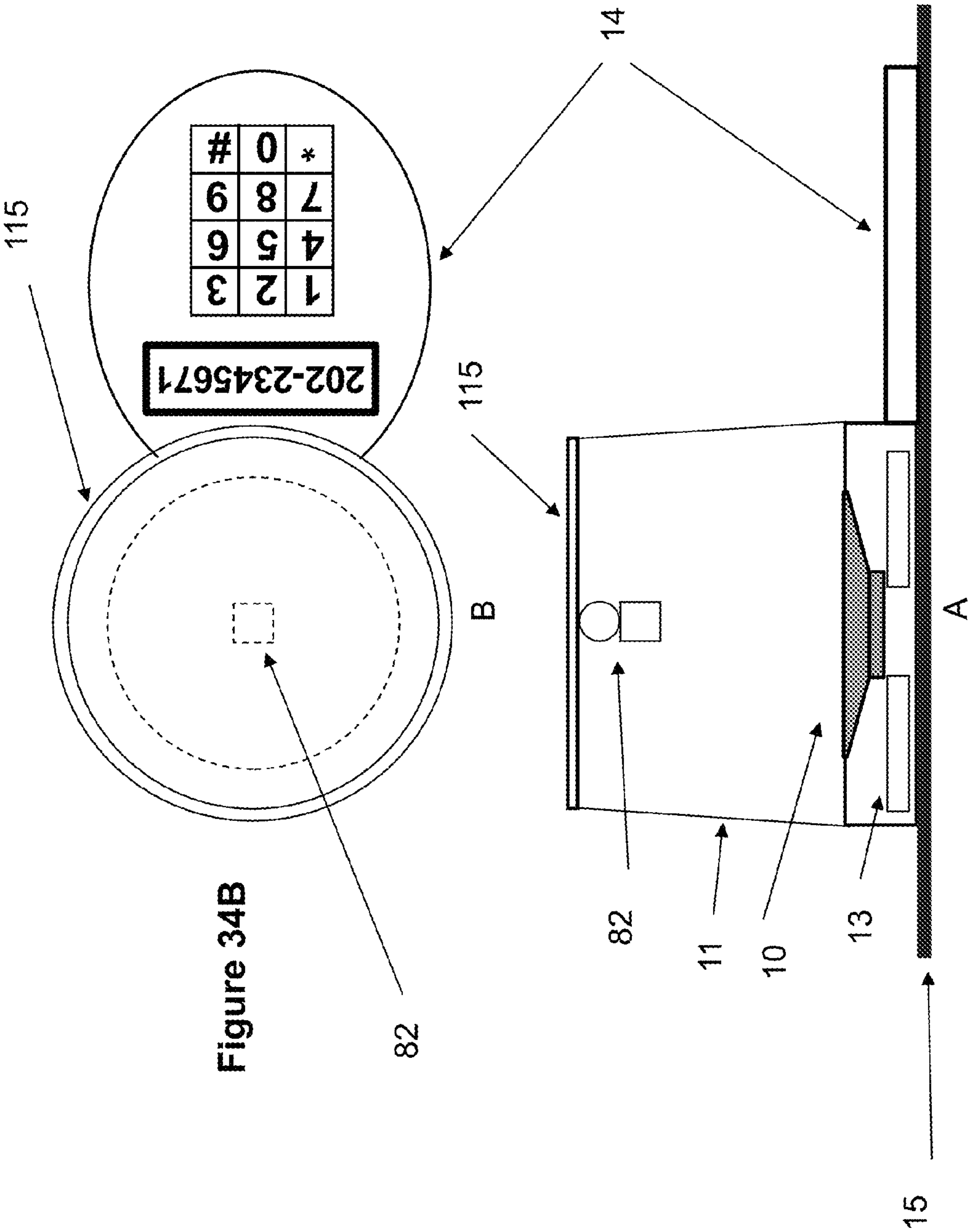
FIGS. 34(*a*) and (*b*) illustrate a schematic for speakerphone device in side view and top view in accordance with certain embodiments.

FIG. 34 shows another variation of the configuration of the speakerphone device 115 using bi-directional microphone elements in accordance with certain embodiments. Here the microphone elements 82 are place located below the upper surface of the device and above the speaker 10.

Figures 35A, 35B:
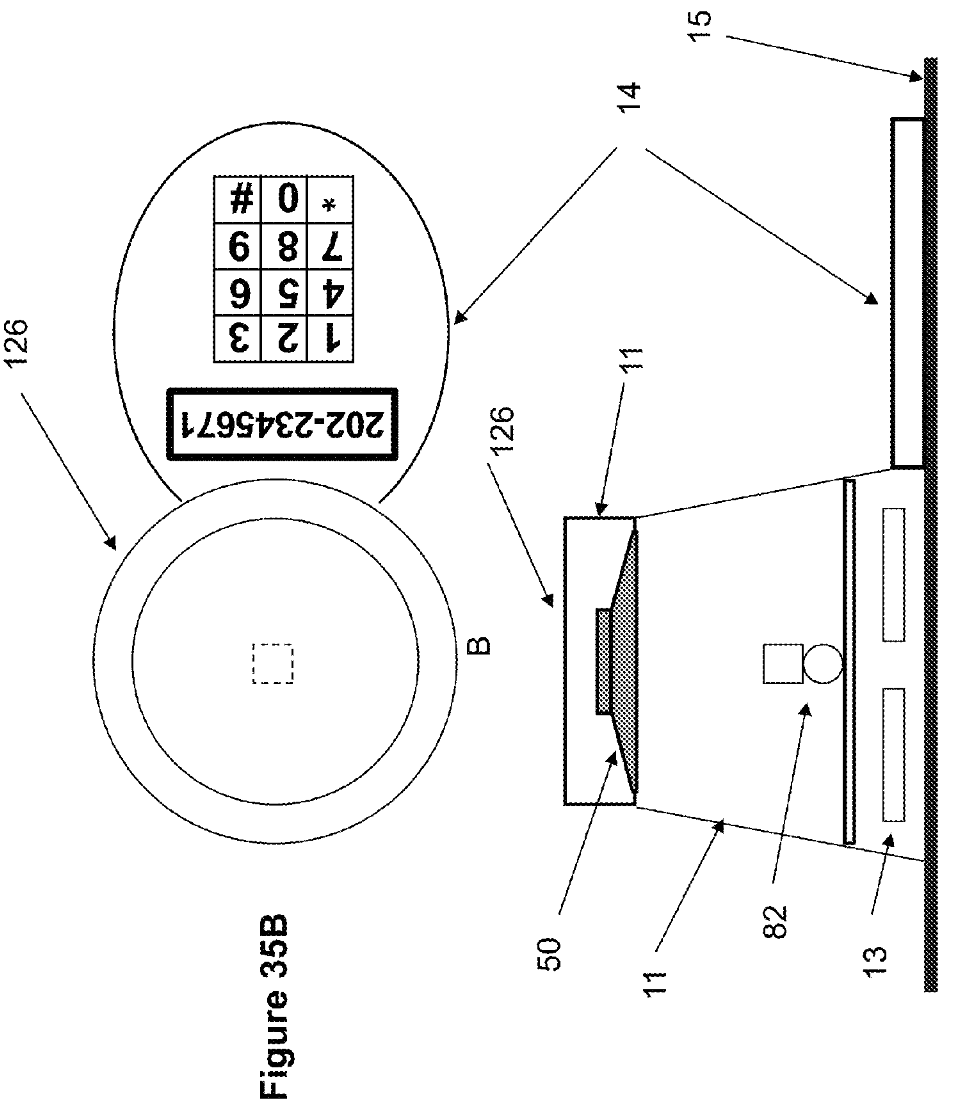
FIGS. 35(*a*) and (*b*) illustrate a schematic for speakerphone device in side view and top view in accordance with certain embodiments.

FIG. 35 shows another variation of the configuration of the speakerphone device 126 using bi-directional microphone elements in accordance with certain embodiments. Here the microphone elements 82 are located at in the lower portion of the device below a down-firing loudspeaker which is located in the upper portion of the device.

Figures 36A, 36B:
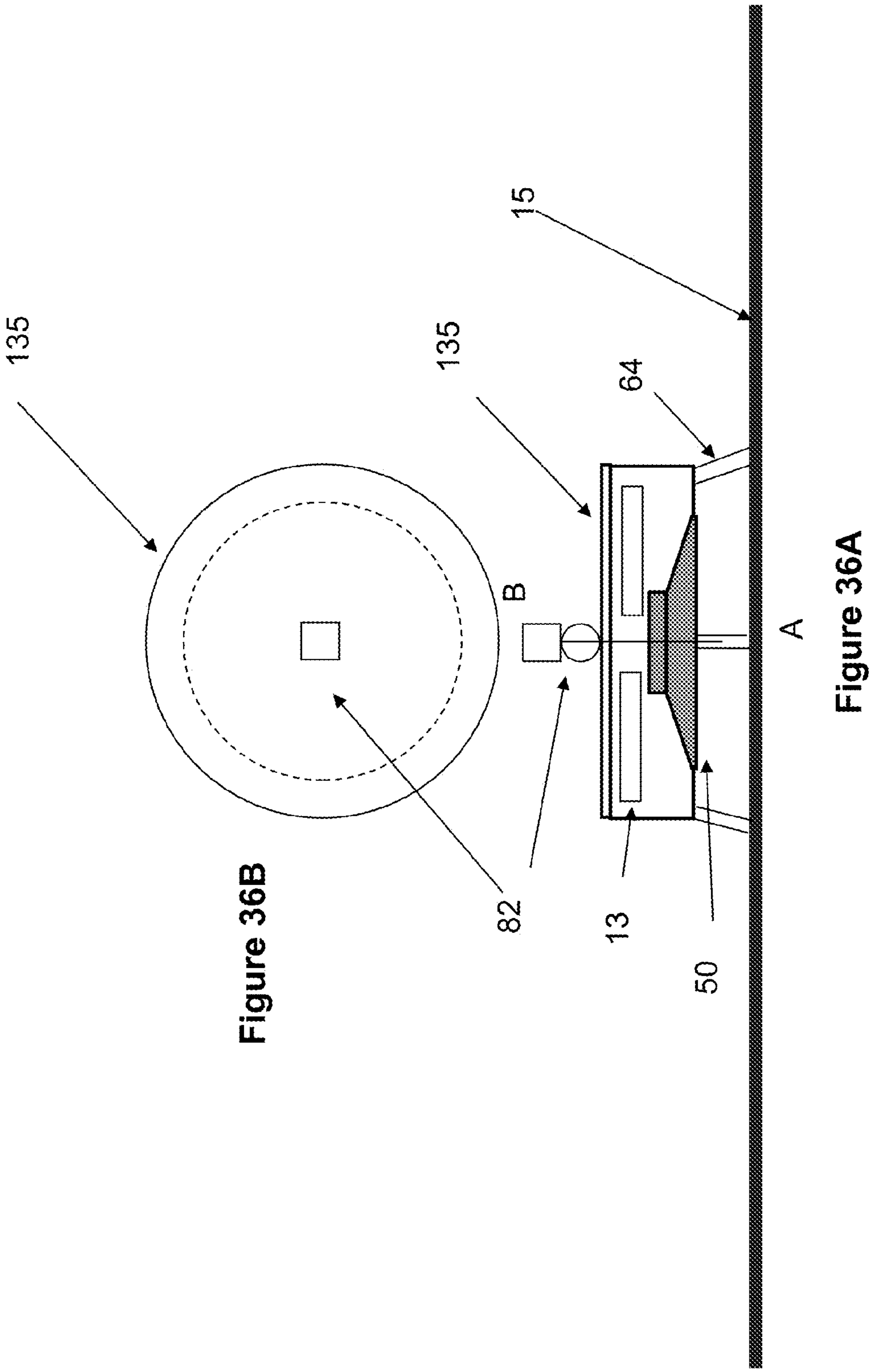
FIGS. 36(*a*) and (*b*) illustrate a schematic for speakerphone device in side view and top view in accordance with certain embodiments.

FIG. 36 illustrates another configuration of the speakerphone device 135 using bi-directional microphone elements in accordance with certain embodiments. Here the microphone elements 82 are stacked near to and above the loudspeaker 10. The down-firing loudspeaker is located in the lower portion of the device. The device is elevated of the surface 15 by the support structure 64.

Figures 37A, 37B:
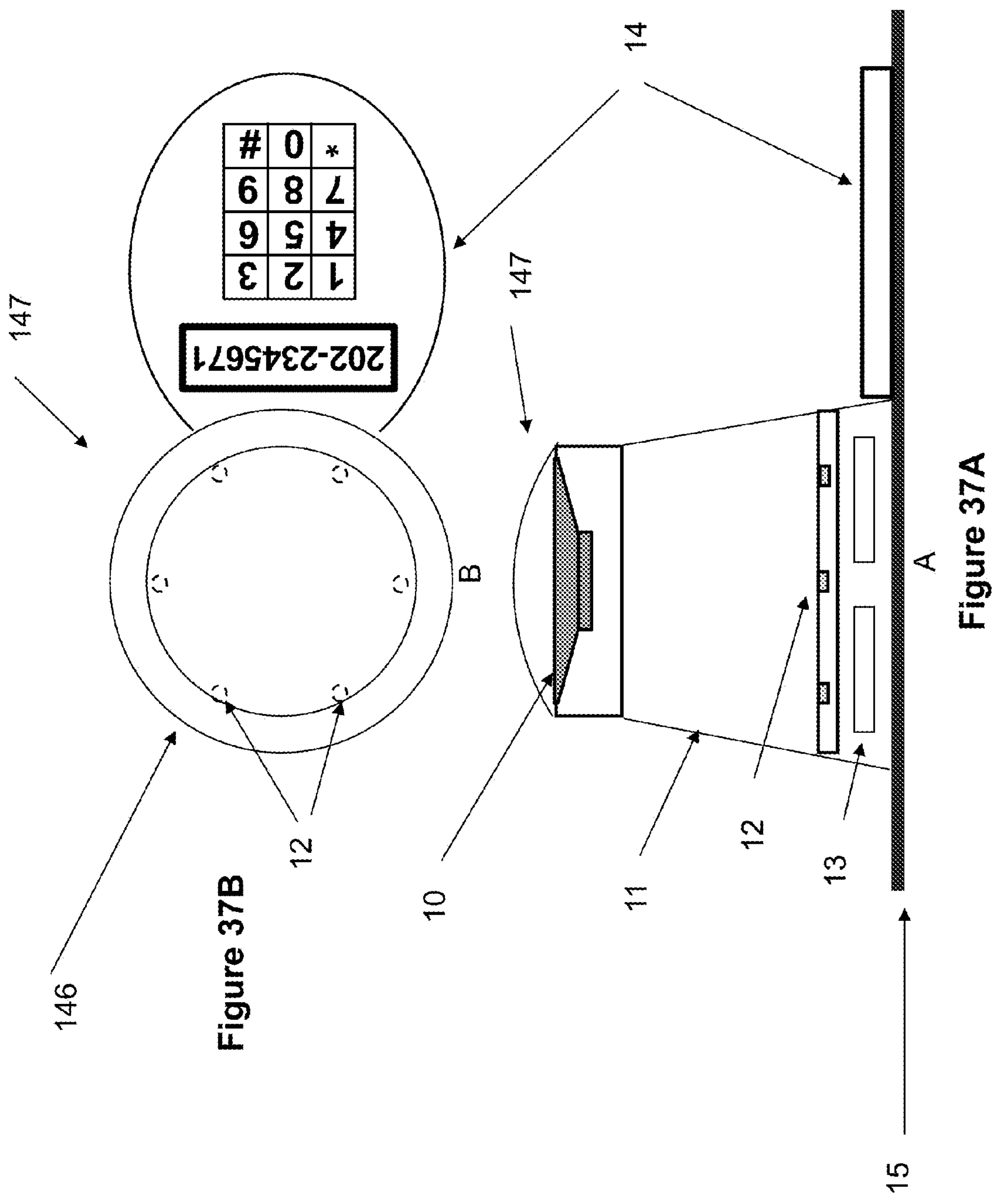
FIGS. 37(*a*) and (*b*) illustrate a schematic for speakerphone device in side view and top view in accordance with certain embodiments.

A speakerphone device 147 is illustrated in FIG. 37 in accordance with certain embodiments. FIG. 37 illustrates six microphone elements 12 that are evenly spaced, or substantially evenly spaced, around a concentric, or substantially concentric, configuration. The phasing of the microphone elements is such that signals arriving from a source with equal path lengths are cancelled, or substantially cancelled. FIG. 37(*a*) show the device in side view and FIG. 37(*b*) shows the device in top view with the out circumference 146 of the device being illustrated. This speakerphone has an up-firing loudspeaker 10 locate above the six microphones 12 in the upper portion of the device and the loudspeaker is covered by a dome 146 that is sufficiently acoustically transparent.

Figures 38A, 38B:
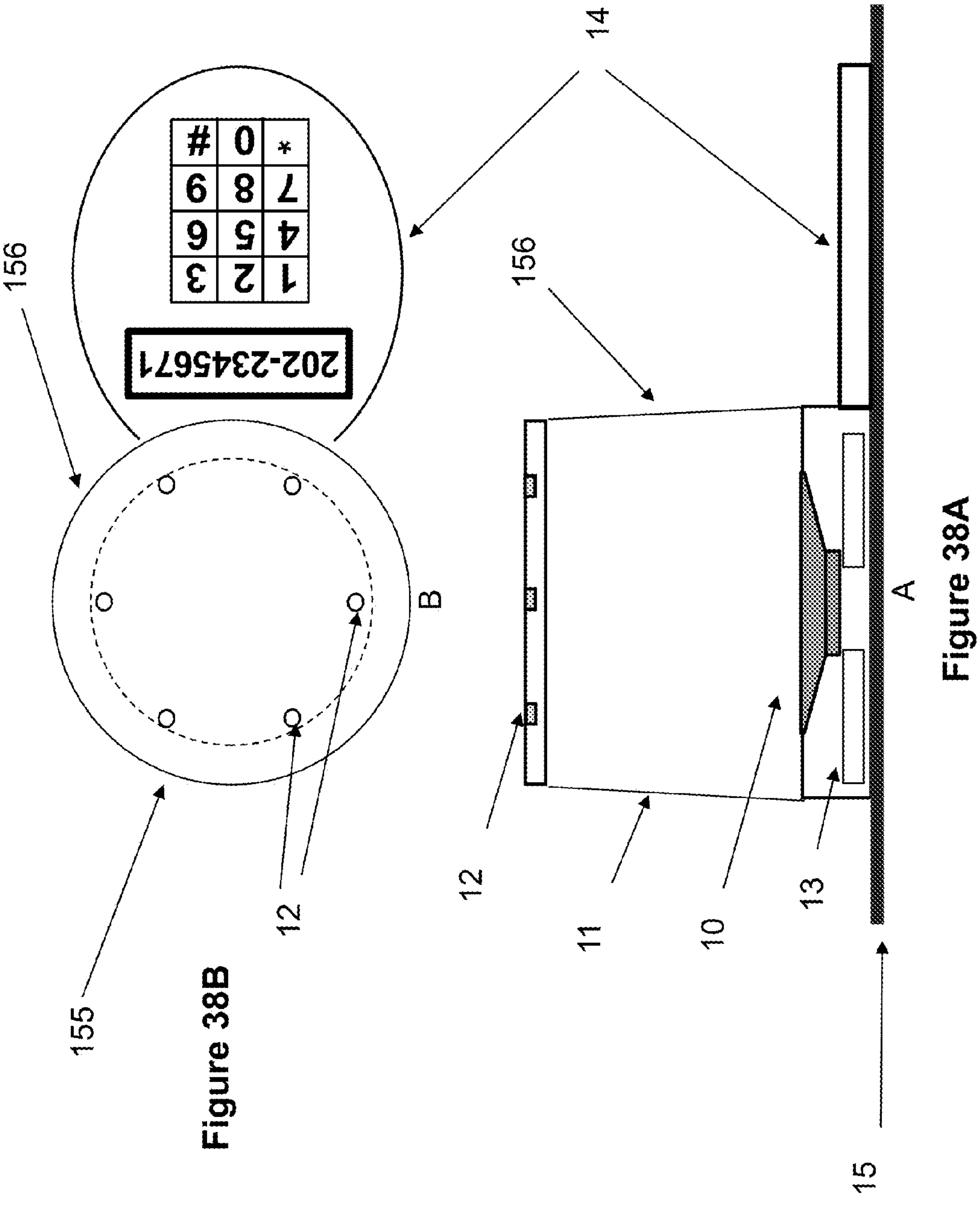
FIGS. 38(*a*) and (*b*) illustrate a schematic for speakerphone device in side view and top view in accordance with certain embodiments.

A speakerphone device 156 is illustrated in FIG. 38 in accordance with certain embodiments. FIG. 38 illustrates six microphone elements 12 that are evenly spaced, or substantially evenly spaced, around a concentric, or substantially concentric, configuration that has a diameter of 120 mm in the upper portion of the device. The phasing of the microphone elements is such that signals arriving from a source with equal path lengths are cancelled, or substantially cancelled. FIG. 38(*a*) show the device in side view and FIG. 38(*b*) shows the device in top view with the outer circumference 155 of the device being illustrated. Here the device has an up-firing loudspeaker 10 locate below the six microphone elements 12 in the upper portion of the device and on the surface of that upper portion.

Figures 39A, 39B:
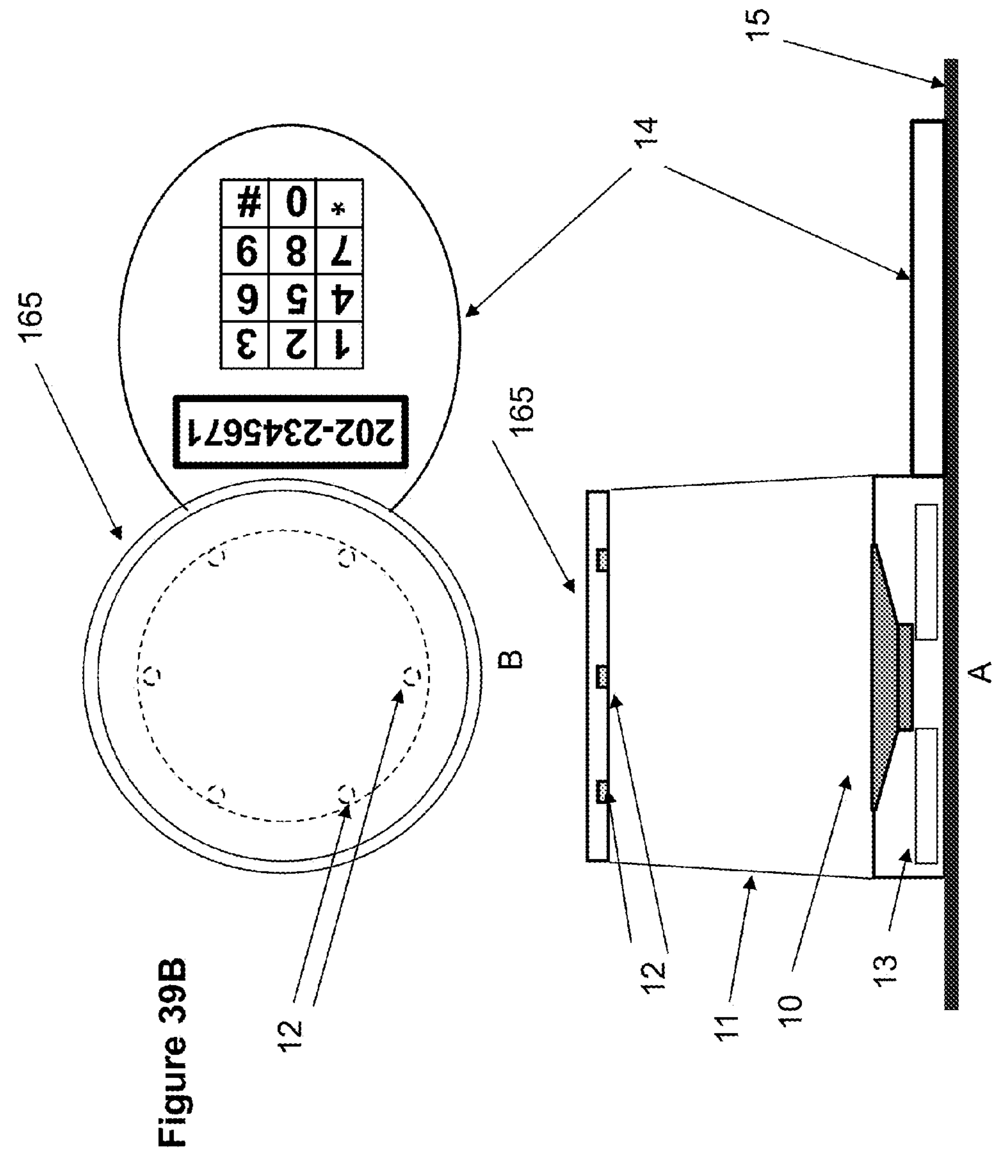
FIGS. 39(*a*) and (*b*) illustrate a schematic for speakerphone device in side view and top view in accordance with certain embodiments.

FIG. 39 illustrates a speakerphone device 165 similar to that shown in FIG. 38. Except here the six microphone elements 12. Here the device has an up-firing loudspeaker 10 locate below the six microphone elements 12 and the microphone elements are located in the upper portion of the device but below the upper surface of the device.

Figures 40A, 40B:
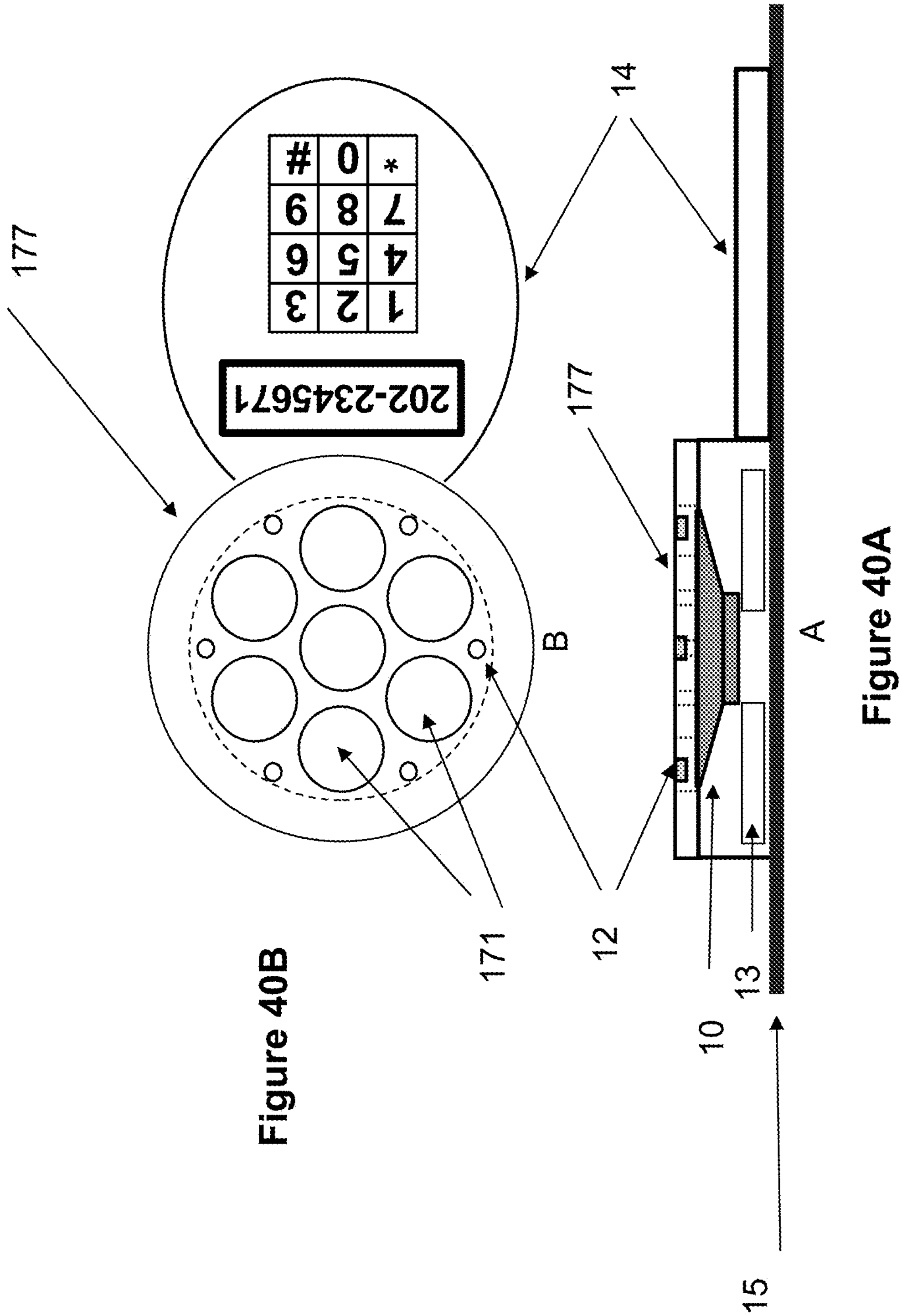
FIGS. 40(*a*) and (*b*) illustrate a schematic for speakerphone device in side view and top view in accordance with certain embodiments.

FIG. 40 illustrates another speakerphone device 177 in accordance with certain embodiments. FIG. 40 illustrates six microphone elements 12 that are evenly spaced around a circumference that is approximately 120 mm in diameter and are exposed at the upper surface of the device. FIG. 40*a* show the device in side view and FIG. 40(*b*) shows the device in top view. This device has an up-firing loudspeaker 10 locate below the six microphones 12. The loudspeaker 10 is disposed in a housing. As can be seen in FIG. 40(*b*), the upper surface of the device has circular holes 171 in the baffle to allow the sound to flow from the loudspeaker. These holes in the baffle provide an alternate equal, or substantially equal pathway from the loudspeaker to each of the microphone elements.

Figures 45A, 45B:
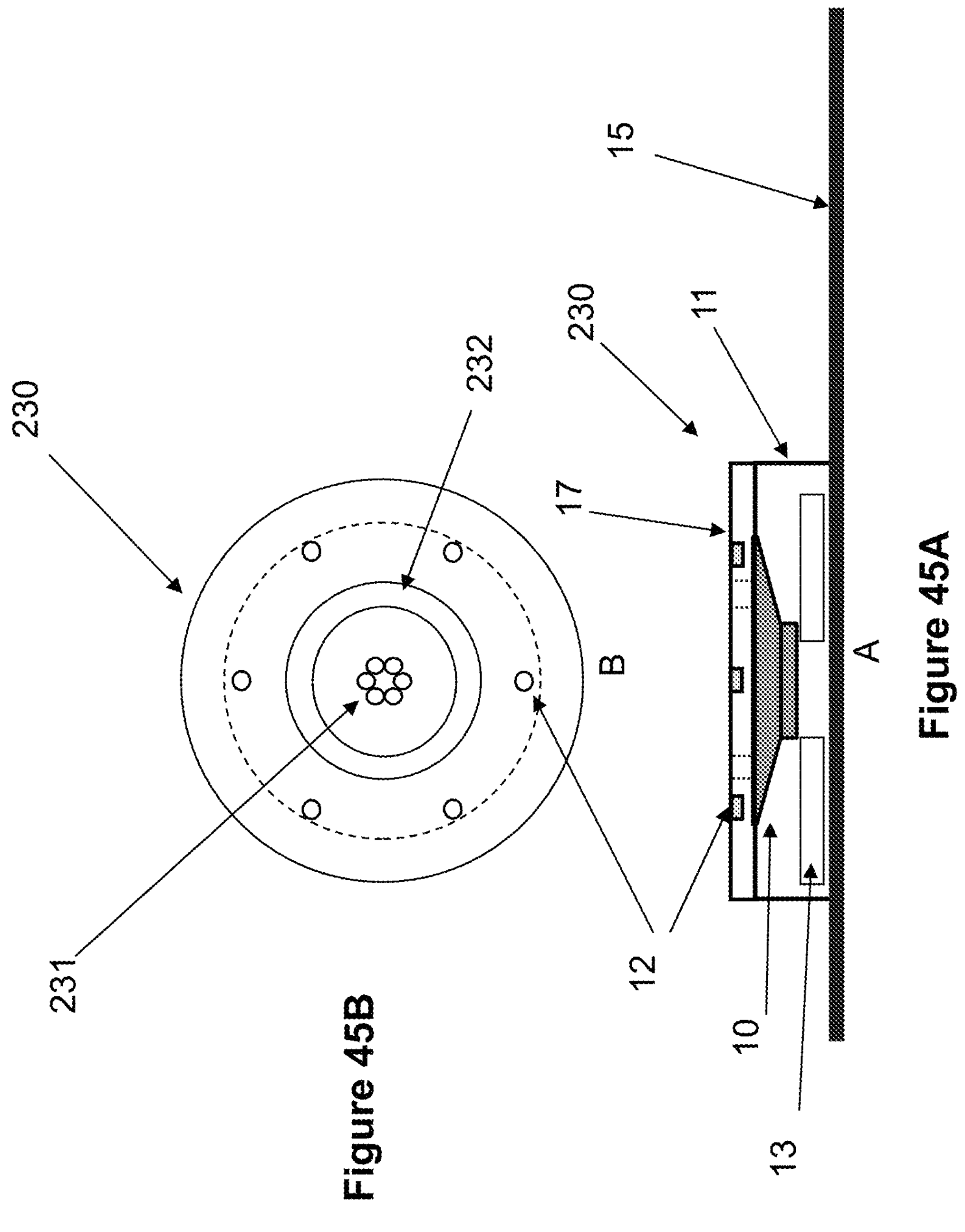
FIGS. 45(*a*) and (*b*) illustrate a schematic for speakerphone device in side view and top view in accordance with certain embodiments.

FIG. 45 illustrates another speakerphone device 230 in accordance with certain embodiments. FIG. 45 illustrates six microphone elements 12 that are evenly spaced around a circumference that is approximately 120 mm in diameter and are exposed at the upper surface of the device. FIG. 45 also illustrated a second cluster of six microphone elements 231 cluster near the center of the device for a total of twelve microphone elements. It is of course possible to vary the number of microphone elements. The microphone elements 231 are shown in FIG. 45(*b*) in plan view but are not shown in FIG. 45(*a*) in side view. This device has an up-firing loudspeaker 10 locate below the 12 microphone elements. The loudspeaker 10 is disposed in a housing 11. As can be seen in FIG. 45(*b*), the upper surface of the device has a circular slot 232 in the baffle to provided and equal, or substantially equal, path length from the loudspeaker to each of the microphone elements.

Figures 41A, 41B:
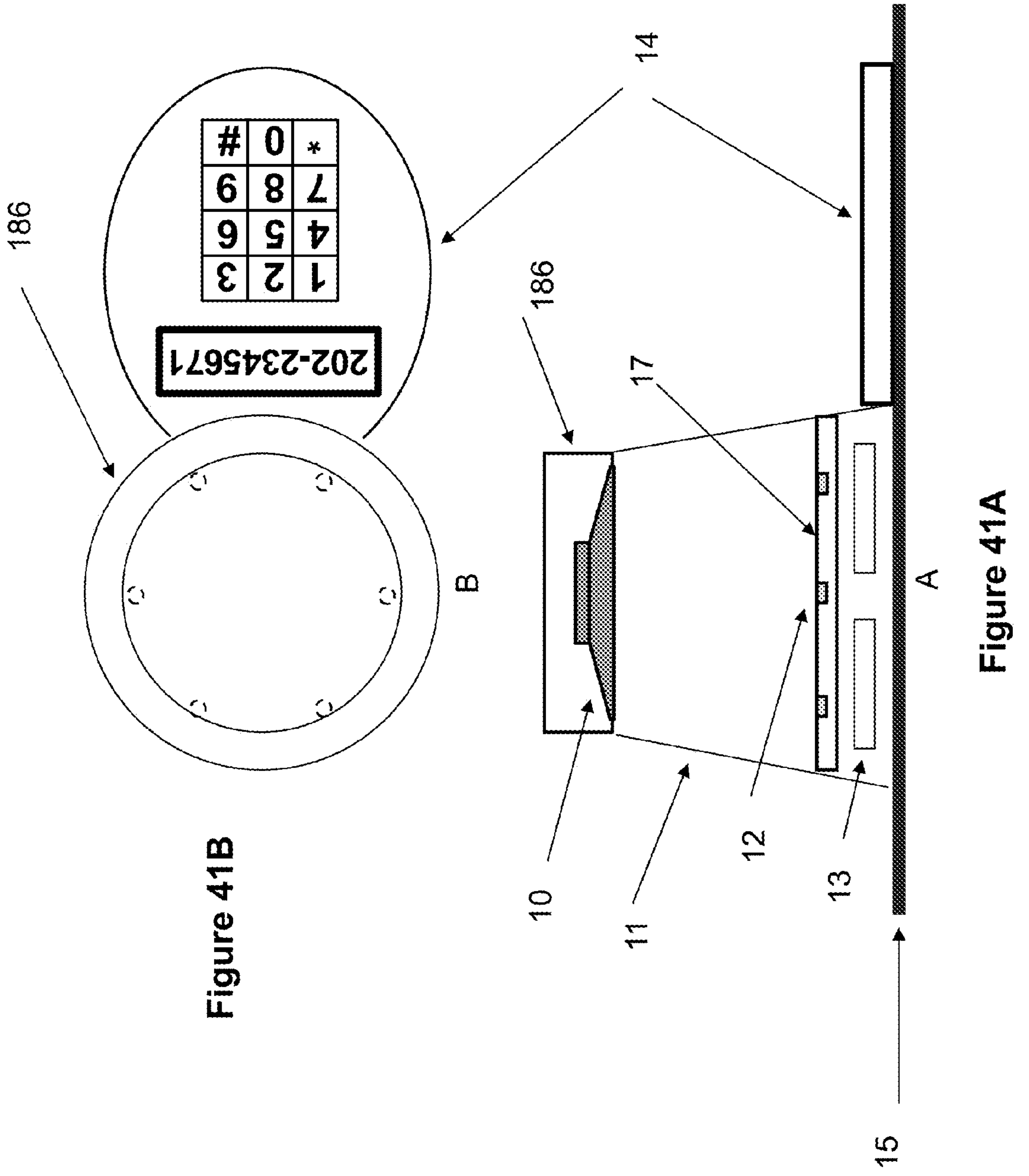
FIGS. 41(*a*) and (*b*) illustrate a schematic for speakerphone device in side view and top view in accordance with certain embodiments.

FIG. 41 illustrates another speakerphone device 186 in accordance with certain embodiments. FIG. 41 illustrates six microphone elements 12 that are evenly, or substantially evening, spaced around a circle. The phasing of the microphone elements is such that signals arriving from a source with equal path lengths, or substantially equal path lengths are cancelled, or substantially cancelled. FIG. 41(*a*) show the device in side view and FIG. 41(*b*) shows the device in top view. This speakerphone has an down-firing loudspeaker 10 locate above the six microphones. The speakerphones loudspeaker 10 is disposed in the housing 11 that is sufficiently acoustically transparent to radiate sound. The microphone elements 12 are equally spaced, or substantially equally spaced, on a circle of about 120 mm and are shown to be mounted in the lower portion of the housing 11 in support structure 17 that is situated at the lower end of the support structure 11.

Figures 42A, 42B:
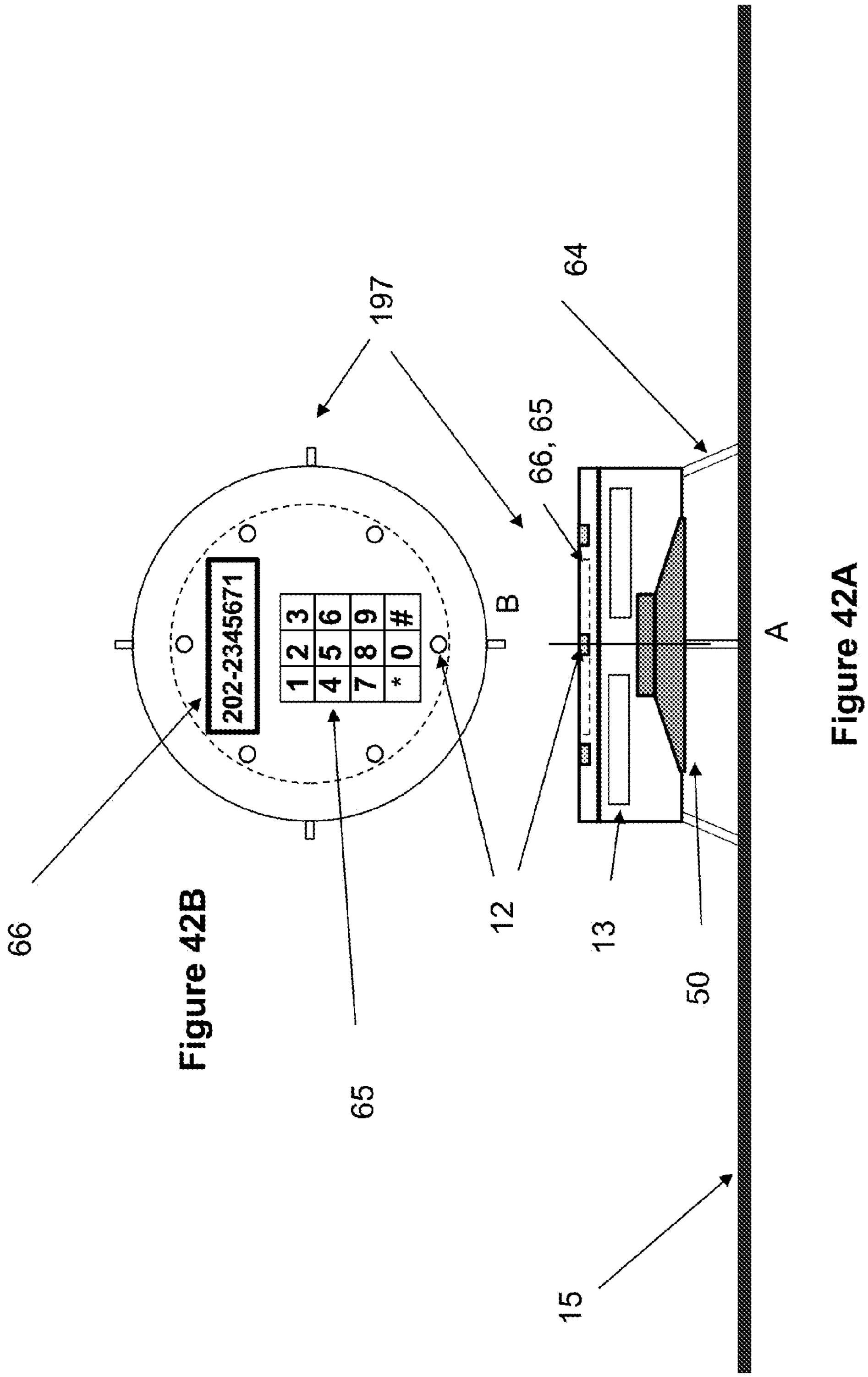
FIGS. 42(*a*) and (*b*) illustrate a schematic for speakerphone device in side view and top view in accordance with certain embodiments.

FIG. 42 illustrates another speakerphone device 197 in accordance with certain embodiments. FIG. 42 illustrates six microphone elements 12 that are evenly spaced, or substantially evenly spaced, around a circumference. Here the microphones 12 are located above the down firing speaker 50. FIG. 42(*a*) show the device in side view and FIG. 42(*b*) shows the device in top view. Here the down-firing loudspeaker 50 is disposed in a housing. In addition, the device is support by four legs 64 that rest on surface 15.

Figure 43B:
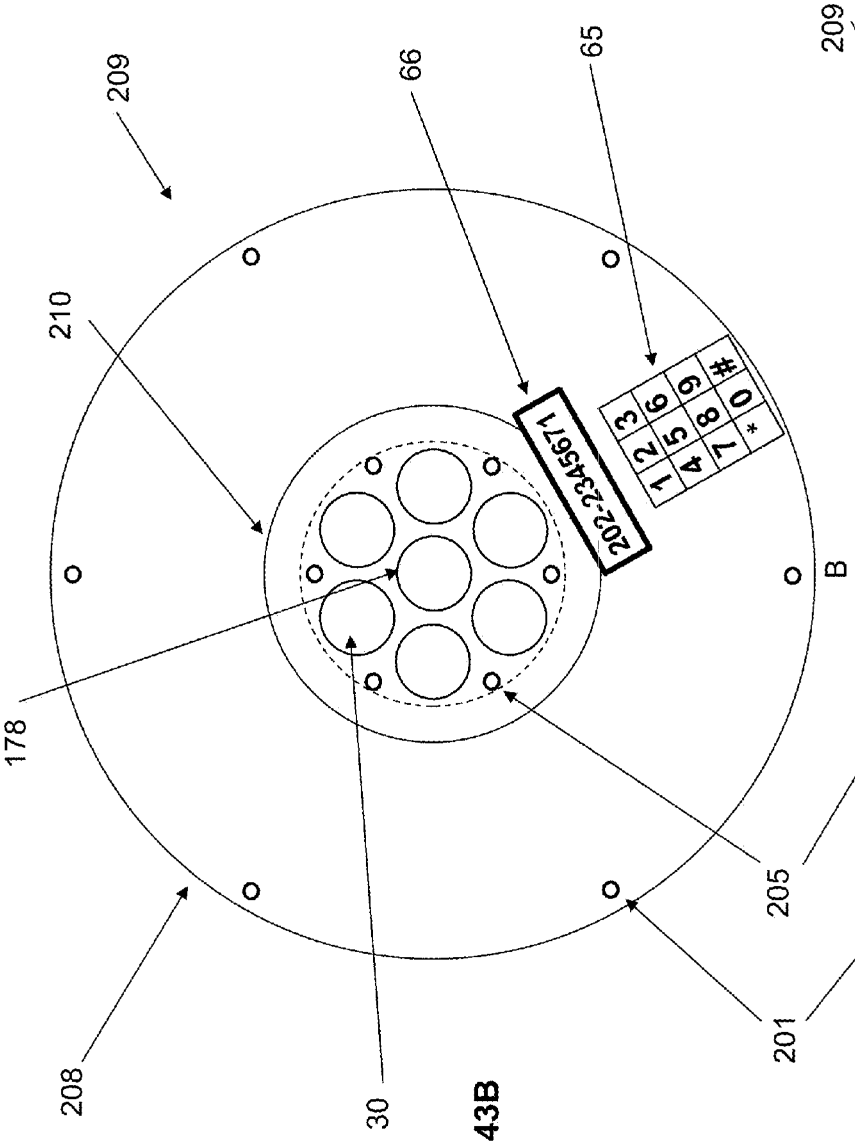
FIGS. 43(*a*) and (*b*) illustrate a schematic for speakerphone device in side view and top view in accordance with certain embodiments.
Figure 43A:
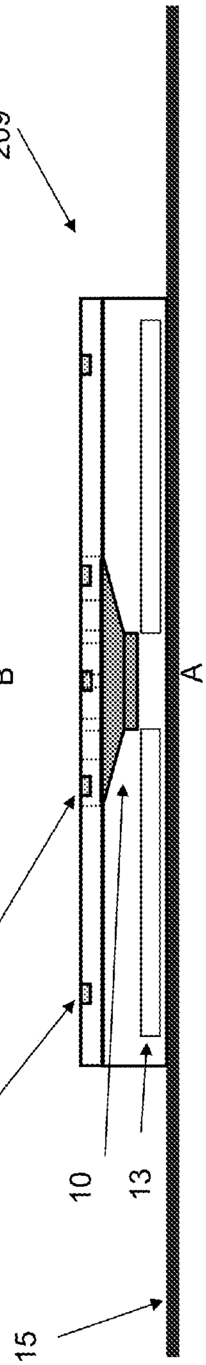

FIG. 43 illustrates another speakerphone device 209 in accordance with certain embodiments. FIG. 43 illustrates an inner grouping of six microphone elements 205 that are evenly spaced, or substantially evenly spaced, around a circumference that is approximately 120 mm in diameter and are exposed at the upper surface of the device. FIG. 43 also illustrates an outer grouping of six microphone elements 201 that are evenly spaced, or substantially evenly spaced, around a circumference that is approximately 300 mm in diameter and are exposed at the upper surface of the device. FIG. 43(*a*) show the device in side view and FIG. 43(*b*) shows the device in top view. This device has an up-firing loudspeaker 10 locate below the microphone elements. The loudspeaker 10 is disposed in a housing. As can be seen in FIG. 43(*b*), the upper surface of the device has circular holes 171 in the baffle to allow the sound to flow from the loudspeaker. These holes in the baffle provide an alternate equal, or substantially equal pathway from the loudspeaker to each of the microphone elements.

Figure 46:
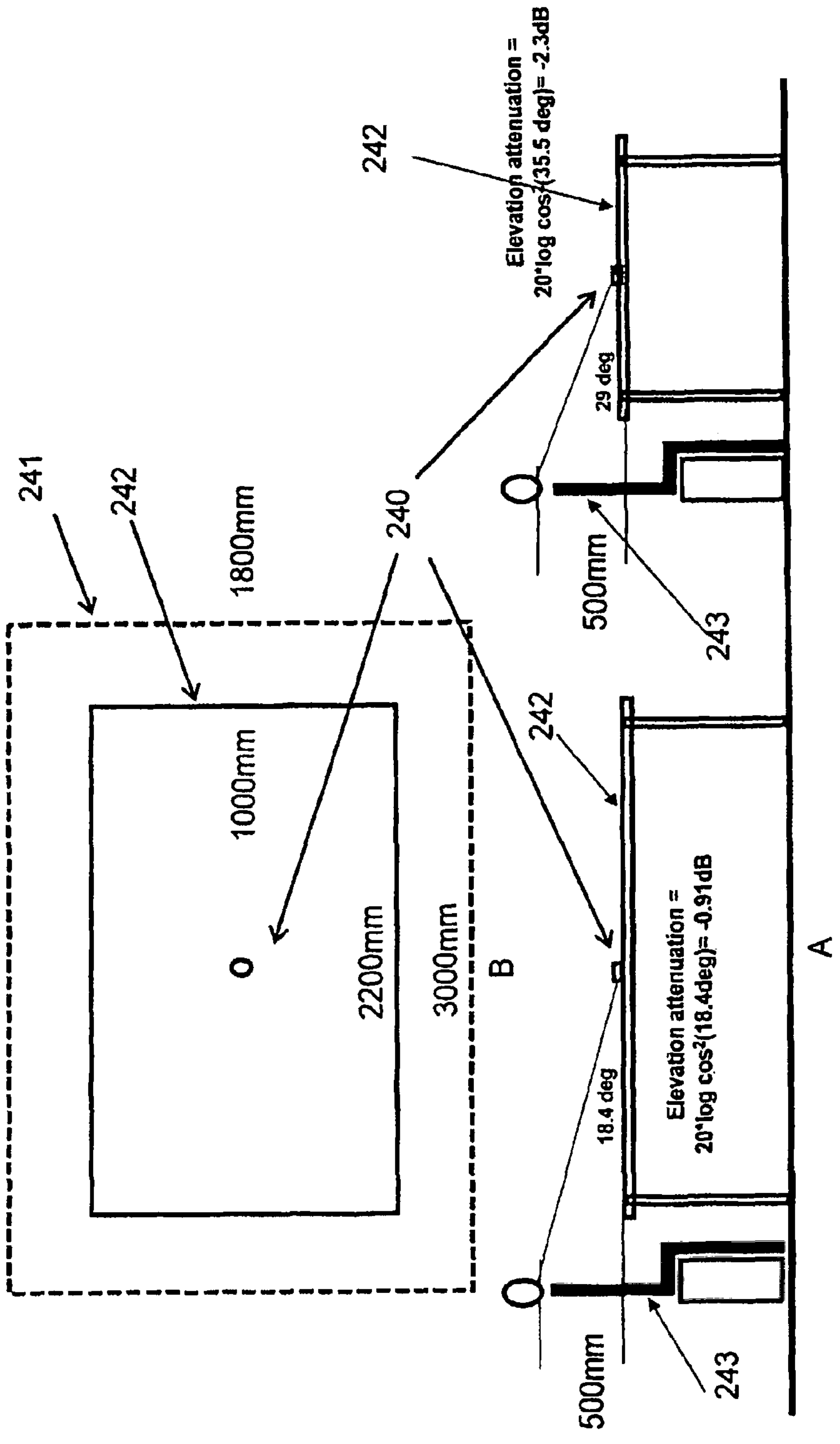
FIG. 46 illustrates the use of certain embodiments in a conference room setting.

FIG. 46 illustrates a small conference table example of how the embodiments disclosed herein may be used. FIG. 43(*a*) show the configuration in side view and FIG. 43(*b*) shows the configuration in top view. In this configuration the speakerphone 240 is located near the center of the table 242 and a person or people 243 are situated around the table. The seating line 241 is about 400 mm from the table 242. Here the attenuation difference due to distance is about 4.2 db and the attenuation difference due to elevation is about −1.4 db.

Figure 47:
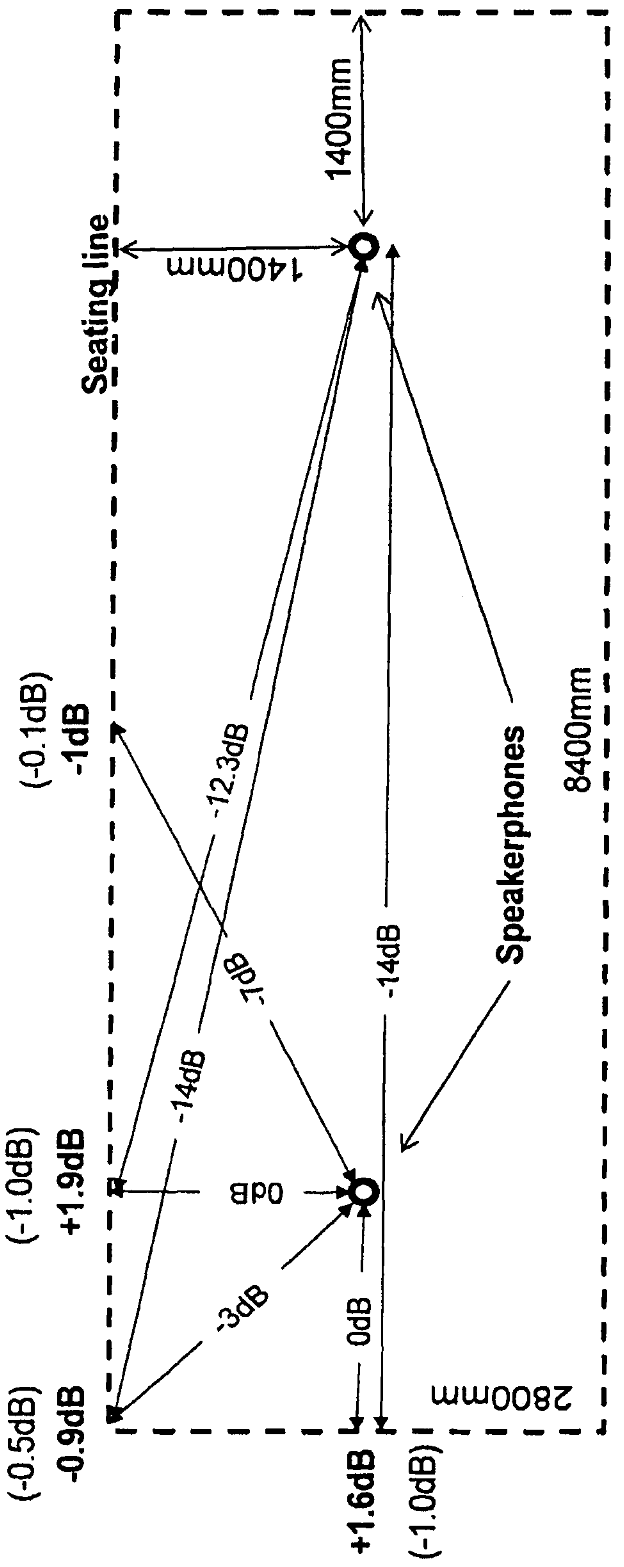
FIG. 47 illustrates the use of the embodiments disclosed in larger conference room setting.

FIG. 47 illustrates another conference room type setting in which two speakerphones are used. On larger conference tables, it may be useful to deploy two or more speakerphones to achieve the necessary coverage with good signal to noise ratio. FIG. 47 shows an example with two speakerphones used on a large conference table where appropriate placement allows the sensitivity variation be under 3 dB or even under 2 dB. This shows the use of two speakerphones on a large conference table where they are each placed equidistant, or substantially equidistant, from the sides and at that same distance, or substantially the same distance, from one end. The arrowed lines show the relative attenuation of the signal at each of the speakerphones for a person speaking from various positions on the seating line. The attenuation figures shown outside the seating line are based on the addition of the signal power received by each speakerphone. The bracketed attenuation is the correction for a second order system used in this way. Such a system used at each end of a conference link would provide a stereophonic arrangement which would help in distinguishing the different contributors.

The speakerphone(s) embodiments disclosed herein may be connected directly by wiring or to a master station by Bluetooth or by a Wi-Fi connection or infrared. The master station will be the connection means to the telephone network or Skype or other means. Communication between multiple speakerphones in the one system may be via direct wiring, or the Wi-Fi or Bluetooth system or by infrared transmission between the individual speakerphones.

While the microphone and/or speakerphones devices have been described in several embodiments, it is to be understood that these embodiments are merely illustrative of the technology. Further variations can be made without departing with the spirit and scope of the technology.

What is claimed is:

1. A device, comprising:

at least three microphone elements;

at least one additional microphone element;

at least one loudspeaker;

at least one housing, wherein the at least one housing is configured to support the at least three microphone elements and the at least one additional microphone element in a first orientation and the at least one loudspeaker in a second orientation; and the at least three microphones are substantially equispaced in a horizontal plane around a circle with a predetermined diameter approximately equal to the wavelength of a predetermined highest frequency of operation of the device and the at least one additional microphone element is positioned at the approximate center of the circle; the at least three microphone elements having substantially equal gain and substantially equal phase and the at least one additional microphone element having a gain substantially equal to the sum of the gains of the at least three microphone elements and a phase shift of about 180 degrees relative to the phase of the at least three microphone elements such that when the signals from the array of microphones are appropriately phased, weighted and summed, the resultant signal in a three-dimensional space is substantially zero in the vertical direction and substantially additive in the horizontal plane direction to achieve a substantial null response in positions having a substantially equal sound path from the at least three microphone elements over a desired audible range of frequencies; and the device is able to provide a response to sounds over a range of second oriented elevations away from the first orientation containing the at least three microphone elements.

2. A device as in claim 1, wherein the at least one loudspeaker is placed substantially below the at least three microphone elements in a position having substantially equal sound paths to each of the at least three microphone elements.

3. A device as in claim 2, wherein the at least three microphone elements are substantially equispaced in a circular arrangement in a substantially horizontal planar configuration.

4. A device as in claim 3, wherein a Hilbert network is used to provide the relative phasing for the microphone elements over the desired bandwidth.

5. A device as in claim 4, wherein the at least three microphone elements comprise four microphone elements.

6. A device as in claim 1 where the at least one loudspeaker is arranged such that the loudspeaker is disposed in a zone of insensitivity of the at least three microphone elements and radiates sound away from the at least three microphone elements and towards a surface upon or against which the housing is abutted, such as a desktop or a vertical wall surface and the at least one loudspeaker has a sound radiation axis that is disposed generally perpendicularly to the abutting surface.

7. A device as in claim 1, wherein the at least three microphone elements are arranged to achieve at least one axis of sensitivity defining a zone of microphone sensitivity, and at least one axis of insensitivity defining a zone of insensitivity of the at least three microphone elements over the 300 Hz to 3.3 KHz frequency range.

8. A device as in claim 1, wherein the at least three microphone elements are arranged to achieve at least one axis of sensitivity defining a zone of microphone sensitivity, and at least one axis of insensitivity defining a zone of insensitivity of the at least three microphone elements over the 300 Hz to 3.3 KHz frequency range; and wherein the at least one loudspeaker is arranged relative to the at least three microphone elements so that the audio from the at least one loudspeaker is also substantially cancelled by the at least three microphone elements and the at least one additional microphone element in the at least one axis of insensitivity defining a zone of insensitivity of the at least one loudspeaker over the 300 Hz to 3.3 KHz frequency range.

* * * * *